US012747431B2

(12) United States Patent
Wherry et al.

(10) Patent No.: US 12,747,431 B2
(45) Date of Patent: Sep. 29, 2026

(54) MODULATION OF EXPRESSION OF GENES RELATED TO T CELL EXHAUSTION

(71) Applicant: THE TRUSTEES OF THE UNIVERSITY OF PENNSYLVANIA, Philadelphia, PA (US)

(72) Inventors: E. John Wherry, Havertown, PA (US); Omar Khan, San Francisco, CA (US); Josephine Giles, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1050 days.

(21) Appl. No.: 17/607,612

(22) PCT Filed: May 1, 2020

(86) PCT No.: PCT/US2020/031064
§ 371 (c)(1),
(2) Date: Oct. 29, 2021

(87) PCT Pub. No.: WO2020/223647
PCT Pub. Date: Nov. 5, 2020

(65) Prior Publication Data

US 2022/0211759 A1 Jul. 7, 2022

Related U.S. Application Data

(60) Provisional application No. 62/841,692, filed on May 1, 2019.

(51) Int. Cl.

| | |
|---|---|
| ***C12N 9/22*** | (2006.01) |
| ***A61K 40/11*** | (2025.01) |
| ***A61K 40/32*** | (2025.01) |
| ***A61K 40/42*** | (2025.01) |
| ***A61K 40/46*** | (2025.01) |
| ***A61P 31/04*** | (2006.01) |
| ***C12N 5/0783*** | (2010.01) |
| ***C12N 15/11*** | (2006.01) |

(52) U.S. Cl.
CPC ................ *C12N 9/22* (2013.01); *A61K 40/11* (2025.01); *A61K 40/32* (2025.01); *A61K 40/4271* (2025.01); *A61K 40/46* (2025.01); *A61P 31/04* (2018.01); *C12N 5/0638* (2013.01); *C12N 15/111* (2013.01); *A61K 2239/57* (2023.05)

(58) Field of Classification Search
CPC .......................... A61K 39/4611; C12N 5/0636
See application file for complete search history.

(56) References Cited

U.S. PATENT DOCUMENTS

2018/0320163 A1 11/2018 Koonin
2021/0071139 A1* 3/2021 Wherry ................ C12Q 1/6883

FOREIGN PATENT DOCUMENTS

CN 109055372 A 12/2018
WO 2017165412 A2 9/2017
WO WO-2019084495 A1 * 5/2019 ............. A61K 38/00
WO WO-2019104245 A1 * 5/2019 ............. A61K 35/17

OTHER PUBLICATIONS

Chen et al. NR4A transcription factors limit CAR T cell function in solid tumours. Nature 2019, 567:530-534. (Year: 2019).*
Sen et al. The epigenetic landscape of T cell exhaustion. Science 2016, 354;6316:1165-1169. (Year: 2016).*
Blattman, Joseph N., et al., "Impact of Epitope Escape on PD-1 Expression and CD8 T-Cell Exhaustion during Chronic Infection", Journal of Virology, 83(9): p. 4386-4394 (2009).
Day, Cheryl L. et al., "PD-1 expression on HIV- specific T cells is associated with T-cell exhaustion and disease procession", 443:350-354 (2006).
Frebel, Helge, et al., "Programmed death 1 protects from fatal circulatory failure during systemic virus infection of mice", J. Exp. Med., vol. 209 , No. 13 2485-2499 (2012).
Giles, J. R. et al., "Characterizing tumor-induced exhaustion in melanoma patients treated with neoadjuvant pembrolizumab", Cancer Immunology Research, Abstract B012, (Feb. 2019).
International Search Report and Written Opinion issued in App. No. PCT/US20/31064, mailing date Aug. 20, 2020, 13 pages.
Odorizzi, Pamela M., et al., "Genetic absence of PD-1 promotes accumulation of terminally differentiated exhausted CD8+ T cells", J. Exp. Med. , vol. 212 , No. 7:1125-1137 (2015).
Paley, Michael A., et al., "Progenitor and Terminal Subsets of CD8+ T Cells Cooperate to Contain Chronic Viral Infection", Science. , 338(6111): 1220-1225 (2012).
Trautmann, Lydie, et al., "Upregulation of PD-1 expression on HIV-specific CD8+ T cells leads to reversible immune dysfunction", Nat Med. , 12(10):1198-1202 (2006).
Urbani, Simona et al., "PD-1 Expression in Acute Hepatitis C Virus (HCV) Infection Is Associated with HCV-Specific CD8 Exhaustion", Journal of Virology, 80(22):11398-11403 (2006).
Wherry, E. John, et al., "Memory CD8 T-Cell Differentiation during Viral Infection", Journal of Virology, 78(11):5535-5545 (2004).
Wherry, E. John, et al., "Molecular and cellular insights into T cell exhaustion", Nat Rev Immunol. , 15(8): 486-499 (2015).
Yi, John S., et al., "T-cell exhaustion: characteristics, causes and conversion", Immunology, 129:474-481 (2010).
Youngblood, Ben et al., "Chronic Virus Infection Enforces Demethylation of the Locus that Encodes PD-1 in Antigen-Specific CD8+ T Cells", Immunity, 35:400-412 (2011).
Youngblood, Ben et al., "Cutting Edge: Prolonged Exposure to HIV Reinforces a Poised Epigenetic Program for PD-1 Expression in Virus-Specific CD8 T Cells", J Immunol, 191:540-544 (2013).

(Continued)

*Primary Examiner* — Christopher M Babic
*Assistant Examiner* — Jennifer S Spence
(74) *Attorney, Agent, or Firm* — Saul Ewing LLP; Kathryn Doyle; Justin Crotty

(57) ABSTRACT

The present invention provides methods of preventing, reducing or reversing T cell exhaustion in a patient having a disease. The present invention also provides methods for treating a disease in a patient having the disease. The present invention also provides an engineered T cell, and uses thereof.

29 Claims, 9 Drawing Sheets

(56) References Cited

OTHER PUBLICATIONS

European Partial Search Report issued Dec. 8, 2022 in European Patent Application No. 20799379.1.
Extended European Search Report issued Mar. 28, 2023 in European Patent Application No. 20799379.1.
Li, H., et al., "Dysfunctional CD8 T Cells Form a Proliferative, Dynamically Regulated Compartment within Human Melanoma", Cell, 176:775-789, 2019.
Rupp, L.J., et al., "CRISPR/Cas9-mediated PD-1 disruption enhances anti-tumor efficacy of human chimeric antigen receptor T cells", vol. 7, No. 37, 10 pages, 2017.

* cited by examiner

MODULATION OF EXPRESSION OF GENES RELATED TO T CELL EXHAUSTION

CROSS-REFERENCE TO RELATED APPLICATION

The present application is a 35 U.S.C. § 371 national phase application from, and claims priority to, International Application No. PCT/US2020/031064, filed May 1, 2020, and published under PCT Article 21 (2) in English, and is entitled to priority under 35 U.S.C. § 119 (e) to U.S. Provisional Patent Application No. 62/841,692 filed May 1, 2019, all of which are incorporated herein by reference in their entireties.

STATEMENT REGARDING FEDERALLY SPONSORED RESEARCH OR DEVELOPMENT

This invention was made with government support under Grant No. A1082630 awarded by the National Institutes of Health (NIH). The government has certain rights in the invention.

BACKGROUND

T cell exhaustion is a common feature of many chronic infections as well as a variety of cancers. T cell exhaustion is characterized by a progressive decline in effector function, manifesting typically as a loss in T cell polyfunctionality. There remains a need for methods of reinvigorating exhausted T cells such as, for example, by modulating the expression of genes related to T cell exhaustion. The present invention addresses this need.

SUMMARY OF THE INVENTION

As described herein, the present invention relates to compositions and methods for preventing, reducing or reversing T cell exhaustion in a patient having a disease.

In one aspect, the invention provides a method of making an improved cell therapy composition for use in treating a disease. The method comprises the steps of: (a) obtaining a sample comprising T cells from a subject, (b) altering a non-coding DNA sequence comprising a regulatory domain present in an open chromatin region (OCR) associated with expression of one or more exhaustion-specific genes in the T cells, and (c) engineering the T cells to target a therapeutically relevant antigen. The altered non-coding DNA sequence reduces or reverses exhaustion of the T cells.

In various embodiments of the above aspects or any other aspect of the invention delineated herein, the sample comprising T cells from the subject comprises CD8+ T cells.

In certain embodiments, the altering comprises knocking-out a regulatory domain present in an OCR associated with expression of one or more exhaustion-specific genes.

In certain embodiments, the method further comprises knocking out a coding DNA sequence of one or more exhaustion-specific genes in the T cells.

In certain embodiments, the exhaustion-specific gene is TOX and the knocking out a coding DNA sequence of one or more exhaustion-specific genes comprises knocking out a single allele of a protein-encoding open reading frame (ORF) encoding the TOX gene in a diploid cell.

In certain embodiments, the exhaustion-specific gene is ZC3H12C and the knocking out a coding DNA sequence of one or more exhaustion-specific genes comprises knocking out part of a protein-encoding ORF encoding one or more exhaustion-specific genes.

In certain embodiments, the part of a protein-encoding ORF comprises an exon.

In certain embodiments, the knocking-out is conducted by a method selected from the group consisting of a clustered interspersed short palindromic repeat (CRISPR)/CRISPR-associated protein (Cas) system, a meganuclease, transcription activator-like effector nucleases (TALEN) and a Zinc-finger nuclease (ZFN).

In certain embodiments, the one or more exhaustion-specific genes is selected from the group consisting of thymocyte selection-associated high mobility group box protein (TOX) and Zinc-finger CCCH-type containing 12C protein (ZC3H12C).

In certain embodiments, the one or more exhaustion-specific genes is ZC3H12C, the altered non-coding DNA sequence comprising a regulatory domain is an enhancer element located 15,358 bp upstream of its transcription start site and the subject is human.

In certain embodiments, the one or more exhaustion-specific genes is ZC3H12C, the altered non-coding DNA sequence comprising a regulatory domain is an enhancer element located on chromosome 11: 109948191-109949139, and the subject is human.

In certain embodiments, the one or more exhaustion-specific genes is ZC3H12C, and the method further comprises knocking out part of the coding sequence for ZC3H12C.

In certain embodiments, the knocking out part of the coding sequence for ZC3H12C comprises knocking out a single exon of the ZC3H12C gene.

In certain embodiments, the single exon of the ZC3H12C gene is exon 2.

In certain embodiments, the one or more exhaustion-specific genes is thymocyte selection-associated high mobility group box protein (TOX), the altering comprises knocking out a single allele of the DNA sequence encoding TOX in a diploid cell, and the subject is human.

In another aspect, the invention provides a method of making an improved cell therapy composition for use in treating a disease. The method comprises the steps of: (a) obtaining a sample comprising T cells from a subject, (b) altering a coding DNA sequence of one or more exhaustion-specific genes; and (c) engineering the T cells to target a therapeutically-relevant antigen. The altered coding DNA sequence reduces or reverses exhaustion of the T cells.

In certain embodiments, the sample comprising T cells from the subject comprises CD8+ T cells.

In certain embodiments, the one or more exhaustion-specific genes is selected from the group consisting of TOX and ZC3H12C.

In certain embodiments, the exhaustion-specific gene is TOX and the altering comprises knocking-out a protein-encoding ORF encoding the TOX gene in a single allele of a diploid cell.

In certain embodiments, the exhaustion-specific gene is ZC3H12C and the altering comprises knocking-out part of a protein-encoding ORF encoding one or more exhaustion-specific genes.

In certain embodiments, the knocking-out is conducted by a method selected from the group consisting of a clustered interspersed short palindromic repeat (CRISPR)/CRISPR-associated protein (Cas) system, a meganuclease, taranscription activator-like effector nucleases (TALEN) and a Zinc-finger nuclease (ZFN).

In certain embodiments, the part of a protein-encoding ORF comprises an exon.

In another aspect, the invention provides an improved cell therapy composition comprising engineered T cells made by any of the processes contemplated herein.

In another aspect, the invention provides a method of treating a disease characterized by increased numbers of exhausted CD8+ effector T cells ($T_{EX}$). The method comprises administering the improved cell therapy composition contemplated herein.

In certain embodiments, the disease is selected from cancer and infection. In certain embodiments, the disease is a viral infection. In certain embodiments, the viral infection is an acute viral infection or a chronic viral infection. In certain embodiments, the disease is an acute viral infection. In certain embodiments, the acute viral infection comprises infection with a virus selected from the group consisting of hepatitis viruses, herpesviruses, polyoma viruses, anelloviruses, adenoviruses, retroviruses, and influenza viruses.

In certain embodiments, the virus is a hepatitis virus selected from the group consisting of Hepatitis A Virus (HAV), Hepatitis B Virus (HBV), Hepatitis C Virus (HCV), Hepatitis D Virus (HDV), Hepatitis E Virus (HEV), GB Hepatitis Virus A (GBV-A), GB Hepatitis Virus B (GBV-B), and GB Hepatitis Virus C (GBV-C).

In certain embodiments, the virus is a herpesvirus selected from the group consisting of alpha-herpesviruses, herpes simplex virus type 1 (HSV1), herpes simplex virus type 2 (HSV2), varicella zoster virus (VZV), beta-herpesviruses, cytomegalovirus (CMV), human herpes virus 6, human herpes virus 7, gamma-herpesviruses, Epstein-Barr virus (EBV), and human herpes virus 8.

In certain embodiments, the virus is a polyoma virus selected from the group consisting of BK virus (BKV), JC virus (JCV), KI polyoma virus (KIPyV), WU virus (WUPyV), Merkel cell polyomavirus (MCPyV), human polyoma virus 6 (HPyV6), human polyoma virus 7 (HPyV7), trichodysplasia spinulosa virus (TSPyV), human polyoma virus 9 (HPyV9), and MW virus (MWPyV).

In certain embodiments, wherein the virus is an adenovirus selected from the group consisting of adenovirus serotype A, adenovirus serotype B, adenovirus serotype C, adenovirus serotype D, adenovirus serotype E, adenovirus serotype F, and adenovirus serotype G.

In certain embodiments, the virus is an influenza virus selected from group consisting of influenza virus A, influenza virus B, influenza virus C, and influenza virus D.

In certain embodiments, the disease is a chronic viral infection. In certain embodiments, the chronic viral infection comprises infection with HIV, HCV or HBV. In certain embodiments, the chronic viral infection is an HIV infection and the subject is being treated with antiretroviral therapy (ART). In certain embodiments, chronic viral infection is a retrovirus infection wherein the retrovirus is selected from the group consisting of alpha-retroviruses, beta-retroviruses, gamma-retroviruses, delta-retroviruses, epsilon-retroviruses, lentiviruses, and spumaviruses. In certain embodiments, the retrovirus is a lentivirus selected from the group consisting of human immunodeficiency virus (HIV) and equine infectious anemia virus (EIAV).

In certain embodiments, the infection is a bacterial infection or a parasite infection.

In certain embodiments, the disease is cancer.

In certain embodiments, the engineering the T cells to target a therapeutically relevant antigen comprises introduction of a recombinant T cell receptor capable of binding a desired antigen/MHC or neo-antigen/MHC combination or introduction of a chimeric antigen receptor capable of binding a desired antigen.

In certain embodiments, the therapeutically relevant antigen is selected from the group consisting of CD19, PSMA, CAIX, HER2, CD30zeta, Folate receptor alpha, Mucin1 (MUC1), Hepatitis C virus E2 glycoprotein, HIV envelope glycoprotein gp120, CMV pp65, GPC3, CEA, Mesothelin, GD2, EGFR, PSMA, EpCAM, BCMA, IL-13R, FAP and CD20.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A is a scheme of identification of open chromatin regions (OCRs) in human CD8 T cells including $T_{EX}$ from human melanoma tumor infiltrating lymphocytes (TILs) and cross-species mapping to identify evolutionarily conserved non-coding elements. This approach identified many exhaustion-specific OCRs in human TILs including a gene, ZC3H12C with 5 exhaustion-specific open chromatin changes. Human TIL-specific OCRs in the ZC3H12C locus and surrounding region were identified by ATAC-seq by comparing CD8 T cells in melanoma tumors to CD8 T cells in PBMCs. FIG. 2B shows the identification of TIL-specific OCRs in ZC3H12C by ATAC-seq and mapping of those (grey with asterisks) that map to mouse $T_{EX}$.

FIG. 3A shows a comparison of changes in RNA expression and chromatin opening for human TIL from FIGS. 2A-2B. Chromatin regions that are increasingly less accessible (designated 'closing' on the left side of the figure) in $T_{EX}$ are shown on the left, with a few specific examples highlighted, while chromatin regions that are increasingly more accessible (designated 'opening' on the right side of the figure) in $T_{EX}$ are shown on the right, with a few specific examples highlighted, including ZC3H12C. FDR=False Discovery Rate. The RNA expression between CD8 T cells in melanoma tumors was compared to CD8 T cells in PBMCs. Genes were considered statistically significant if the FDR was below 0.05. The boxed genes were highlighted because they have a large change in RNA expression (as measured by RNA-seq) and/or a a large number of altered associated peaks (as measured by ATAC-seq). FIG. 3B shows an expression pattern of ZC3H12C in different T cell types from PBMC pre and 3 weeks post (C1) anti-PD-1 treatment or in tumor at 3 weeks post (C1) anti-PD-1 treatment.

FIG. 6A shows mouse design and experimental schematic. FIG. 6B shows reduced $T_{EX}$ responses during chronic infection for cells lacking the enhancer element (circles on right) compared to WT control T cells (circles on left).

DETAILED DESCRIPTION

Definitions

Figure 1:
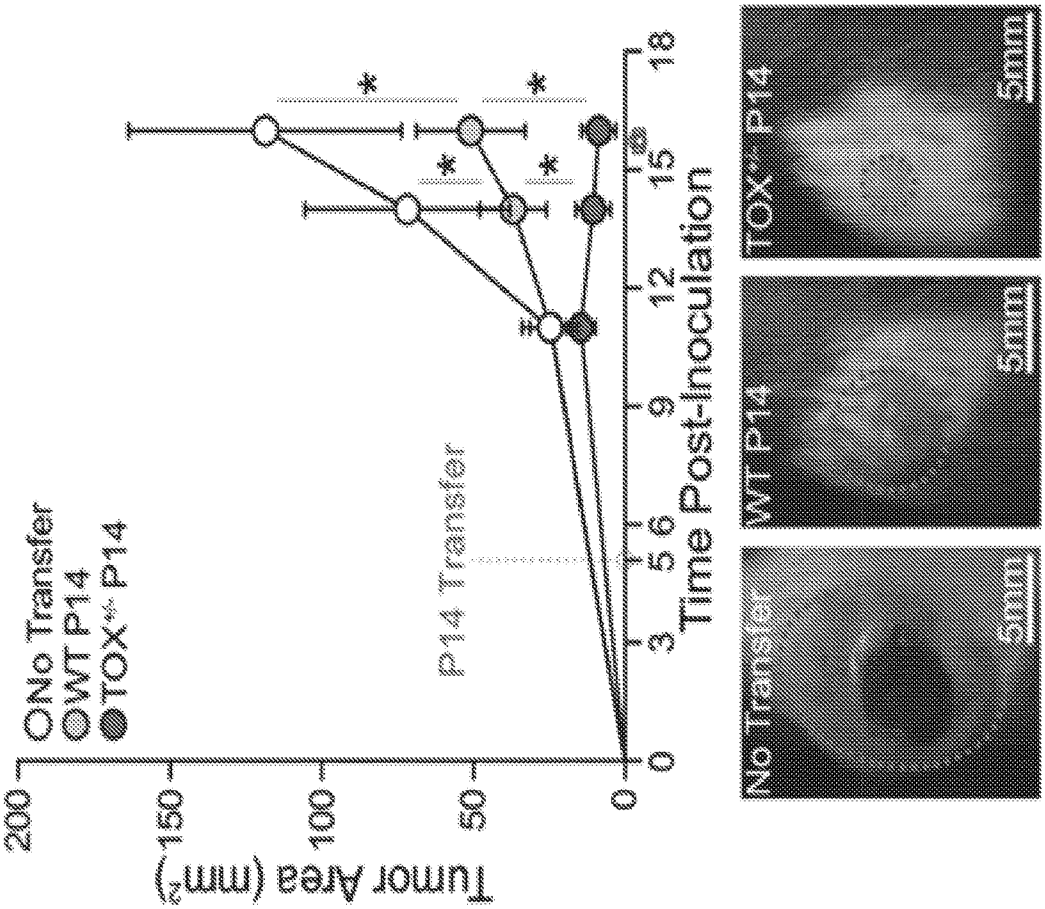
FIG. 1 is a graph plotting tumor area in square millimeters versus time post-inoculation with wild type P14 cells (WT P14, circles filled in light grey), P14 cells in which one of two copies of the Tox gene was knocked out ($TOX^{+/-}$ P14, circles filled in dark grey), or with no transfer. Below it are three images showing an exemplary tumor from an animal from each group included on the graph. The images were taken at 17 days after tumor inoculation. WT or Tox P14 cells were preactivated in vitro and then adoptively transferred into mice containing B16-GP33 tumors on the flank. Serial tumor area measurements were then made and tumors visualized on the flanks.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instances ±0.1% from the specified value, as such variations are appropriate to perform the disclosed methods.

The term "activated" or "activation," as used herein, refers to the state of a T cell that has been sufficiently stimulated to induce detectable cellular proliferation, cytokine production, effector functions, and other measurable indicia of T cell activity. The term "activated T cells" refers to, among other things, T cells that are undergoing cell division.

"Activators" or "agonists" of are used herein to refer to molecules of agents capable of activating or increasing the levels of the soluble factor. Activators are compounds that increase, promote, induce activation, activate, or upregulate the activity or expression of soluble factor, e.g., agonists. Assays for detecting activators include, e.g., expressing the soluble factor in vitro, in cells, or cell membranes, applying putative agonist compounds, and then determining the functional effects on activity of the soluble factor, as described elsewhere herein.

As used herein, a "blocking" agent, an "inhibitor" or an "antagonist" is one which inhibits or reduces at least one biological activity of the factor(s) it binds. In certain embodiments, the blocking agent is a biologic and the biologic is a blocking antibody. A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s). For example, an anti-PD-1 antibody binds PD-1 and inhibits the ability of PD-1 to bind one or more ligands, for example, PD-L1 and/or PD-L2. In certain embodiments, the blocking antibodies or antagonist antibodies or fragments thereof described herein substantially or completely inhibit a given biological activity of the antigen(s). In certain embodiments, the term "inverse agonist" is used to refer to an agent that binds to the same target or receptor as an agonist but induces a pharmacological response opposite to that agonist. For example, a PD-1 inverse agonist can promote co-stimulation as opposed to co-inhibition of immune responses. In some embodiments, the "blocking" agent is a nucleic acid inhibitor such as siRNA or antisense RNA, genetically modified versions of the factor, e.g., versions with altered activity, as well as naturally occurring and synthetic factor antagonists, small chemical molecules and the like. As used herein, an agent that can reverse or prevent cell exhaustion can be, without limitation, any existing or novel epigenetic drug currently in the clinic or in development. Many of these agents are have not been used to target immune cells. They are used herein for their effects on tumor cells and infectious diseases. As used herein, an agent that can reverse or prevent T cell exhaustion can be, without limitation, any immunotherapy drug or agent including any checkpoint blockades or others agents that instigate a change in immune function.

The term "ATAC-seq" (Assay for Transposase-Accessible Chromatin using sequencing) is a technique used in molecular biology to study chromatin accessibility. ATAC-seq is a rapid and sensitive method for epigenomic analysis. ATAC-seq identifies open chromatin sites and can reveal the interplay between genomic locations of open chromatin, DNA-binding proteins, individual nucleosomes and chromatin compaction at nucleotide resolution. Chromatin undergoes various structural changes during a cell cycle. Histone proteins are the basic packer and arranger of chromatin and can be modified by various post-translational modifications to alter chromatin packing (histone modification). Most of the modifications occur on the histone tail. The consequences in terms of chromatin accessibility and compaction depend on, e.g., the amino-acid that is modified and the type of modification. For example, histone acetylation generally results in loosening and increased accessibility of chromatin for replication and transcription.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

As used herein, to "alleviate" a disease means reducing the severity of one or more symptoms of the disease.

The term "biomarker" or "marker" refers to a measurable entity of the present invention that has been determined to be indicative of T cell exhaustion. For example, biomarkers described herein can be genomic regulatory regions that modulate the expression of at least one gene in a T cell. In some embodiments, biomarkers described herein can be open chromatin regions (OCRs) or combinations of OCRs associated with a particular sub-type of T cell. In some embodiments, biomarkers described herein can be effector genes or products thereof expressed by T cells and related to T cell activity and/or T cell exhaustion (e.g., high sustained PD-1 expression and/or activity in exhausted T cells. Biomarkers can also include, without limitation, cell types (e.g., engineered T cells), cell ratios (e.g., engineered T cells to exhausted T cell ratio), nucleic acids (e.g., genomic nucleic acids and/or transcribed nucleic acids) and proteins, particularly those provided in Pauken et al. Table S1 (Pauken et al. Science 2016, 354(6316):1160-1165), Biomarkers can further include immunological targets or agents that downregulate unwanted immune reactions in order to treat the immune disorder of interest as described further herein. The modulation (e.g., increase or decrease) in biomarker activity can be measured in any number of ways (e.g., according to measures described herein, including using controls, ratios, comparisons to baselines, and the like). For example, a genomic regulatory region selectively chromatin accessible in exhausted CD8+ T cells that is engineered can decrease enhancer activity on at least one gene as measured by a reduction in gene expression (e.g., gene transcription and/or translation) of the at least one gene as compared to the transcription and/or translation of the at least one gene in the same T cell type from the same organism without the engineered genomic regulatory region. The modulation in gene expression can be assessed over time. A modulation can mean a change of at least 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 450%, 500%, 550%, 600%, 650%, 700%, 750%, 800%, 850%, 900%, 950%, 1000%, or more, or any range in between inclusive (e.g., 5% to 100%).

It is to be noted that the biomarkers described herein can be used to refer to any combination of features described herein regarding any individual or combination of such biomarkers. For example, any combination of ortholog across organisms, sequence composition, percentage identity, sequence length, domain structure, functional activity, mutation status, etc. can be used to describe a biomarker molecule of the present invention.

The term "bispecific antibody" or "multispecific antibody" refers to an antibody that recognized more than one epitope. Such antibodies are useful for targeting different proteins using the same agent. Methods of making such antibodies are well-known in art (see, at least U.S. Pat. Nos. 5,798,229; 5,989,830; and Holliger et al. (2005) *Nat. Biotech.* 23:1126-1136).

As used herein, the term "immune checkpoints" means a group of molecules on the cell surface of CD4+ and CD8+ T cells. These molecules fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, BTLA, SIRPalpha (CD47). CD48. 2B4 (CD244), B7.1, B7.2, ILT-2, ILT-4, TIGIT, and A2aR (see, for example, WO 2012/177624). Immunotherapeutic agents that can act as immune checkpoint inhibitors useful in the methods of the present invention, include, but are not limited to, Fc fusion proteins having effector function, such as certain classes of antibodies well-known in the art.

The terms "anti-immune checkpoint therapy". "immune checkpoint blockade", "immune checkpoint inhibition therapy" and the like refer to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can bind to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "influenza virus," as used herein, refers to an RNA virus that is a member of the Orthomyxoviruses family. In some embodiments, the influenza virus is selected from the genera consisting of Influenza virus A, Influenza virus B, Influenza virus C and Influenza virus D. In further embodiments, the influenza A virus is of the subtype H1N1, H1N2, H2N2 or H3N2. In further embodiments, the influenza B virus of the B/Yamagata/16/88-like lineage or the B/Victoria/2/87-like lineage.

The term "polyoma virus," as used herein, refers to an unenveloped DNA virus that is a member of the Polyomaviridae family. A polyomavirus is a DNA virus with a circular genome. Some members of the family are oncoviruses, and may cause tumors. In some embodiments, the polyoma virus is BK virus (BKV), JC virus (JCV), KI polyoma virus (KIPyV), WU virus (WUPyV), Merkel cell polyomavirus (MCPyV), human polyoma virus 6 (HPyV6), human polyoma virus 7 (HPyV7), trichodysplasia spinulosa virus (TSPyV), human polyoma virus 9 (HPyV9), or MW virus (MWPyV).

The term "immune disorders" refers to conditions characterized by an unwanted immune response. Immune disorders may be acute or chronic. In some embodiments, the immune disorder is such that a desired anti-immune disorder response suppresses immune responses. Such conditions in which downregulation of an immune response is desired are well-known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, a disorder requiring improved vaccination efficiency, and a disorder requiring increased regulatory T cell production or function, as described further herein. In other embodiments, the immune disorder is such that a desired response is an increased immune response. Such conditions in which upregulation of an immune response is desired are well-known in the art and include, without limitation, disorders requiring increased CD4+ effector T cell production or function such as combating cancer, infections (e.g., parasitic, bacterial, helminthic, or viral infections), and the like. In some embodiments, the immune disorder is an autoimmune disorder. Importantly, exhaustion occurs in autoimmunity (McKinney et al. Nature. 2015, 523:612-616).

The term "acute immune disorder" refers to conditions that can be resolved by an appropriate immune response that eradicates a targeted antigen and host comprising such a targeted antigen, such as a cancer or an infection agent like a virus, bacteria, parasite, mycoplasma, fungus, and the like. Such conditions are relatively brief and last on the order of a few days to a few weeks.

By contrast, the term "chronic immune disorders" refers to those conditions that are not effectively cleared or eliminated by the induction of a host immune response. In chronic immune disorders, a targeted antigen (and/or host comprising the targeted antigen), such as an infectious agent or cancer cell, and the immune response reach equilibrium such that the subject maintains the targeted antigen or host comprising the targeted antigen (e.g., remains infectious or afflicted with cancer) over a long period of time (i.e., a time period of months to years or even a lifetime) without necessarily expressing symptoms. Chronic immune disorders can involve stages of both silent and productive targeted antigen maintenance without rapidly killing or even producing excessive damage of the host cells. Detection of the targeted antigen or host comprising the targeted antigen can be made according to any one of many well-known methods in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 200201067.

In some embodiments, chronic immune disorders are the result of infection, such as an infection with a virus including, but not limited to, human immunodeficiency viruses HIV), hepatitis C viruses (HCV), T-cell leukemia viruses, Epstein-Barr virus, cytomegalovirus, herpesviruses, varicella-zoster virus, measles, papovaviruses, prions, hepatitis viruses, adenoviruses, parvoviruses, papillomaviruses, prions, and the like. In some embodiments, chronic immune disorders are the result of infection, such as an infection with a virus including, but not limited to hepatitis B virus, noroviruses, and/or anelloviruses. In some embodiments, chronic immune disorders are the result of infection with non-viral chronic infections including, but not limited to malaria, *Mycobacterium tuberculosis*, trypanasoma cruzi, *Toxoplasma gondii*, and/or *Leishmania major*. Chronic immune disorders include, for example, chronic conditions and latent conditions. As used herein, chronic immune disorders can be limited to chronic conditions, latent conditions, or both.

In a "chronic condition," the targeted antigen can be detected in the subject at all times regardless of whether the signs and symptoms of the disease are present or absent, even for an extended period of time. Non-limiting examples of chronic conditions resulting from infection include hepatitis B (caused by hepatitis B virus (HBV)) and hepatitis (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human immunodeficiency virus (HIV), human T cell leukemia virus I, and human I cell leukemia virus II. Parasitic persistent infections can arise as a result of infection by, for example. Leishmania Toxoplasma, Trypanosoma, Plasmodium, Schistosoma, Encephalitozoon, norovirus, anellovirus, mycobacterium species, malaria species, malaria, *Mycobacterium tuberculosis*, trypanasoma cruzi, *Toxoplasma gondii*, and/or *Leishmania major.*

A particular type of chronic condition involving infections is known as a "latent condition," where the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Infection latency is the ability of a pathogenic infection agent, such as a virus, to lie dormant within a cell. For example, a latent viral infection is a phase in the life cycle of certain viruses in which after initial infection, virus production ceases. However, the virus genome is not fully eradicated. The result of this is that the virus can reactivate and begin producing large amounts of viral progeny (the lytic part of the viral life cycle) without the host being infected by a new virus. The virus may stay within the host indefinitely. In one embodiment, virus latency is not identical to clinical latency, in which the virus is undergoing an incubation period but is not dormant. Non-limiting examples of latent infections include infections caused by herpes simplex virus (HSV)-1 (fever blisters), HSV-2 (genital herpes), and varicella zoster virus VZV (chickenpox-shingles).

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

The terms "inhibit" or "reverse" include the decrease, limitation, or blockage, of, for example a particular action, function, or interaction. In some embodiments, an immune disorder is "inhibited" or "reversed" if at least one symptom of the immune disorder is alleviated, terminated, slowed, or prevented. As used herein, an immune disorder is also "inhibited" or "reversed" if recurrence or spread of the immune disorder is reduced, slowed, delayed, or prevented.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

The terms "cancer" or "tumor" or "hyperproliferative disorder" and the like refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancer cells can spread locally or through the bloodstream and lymphatic system to other parts of the body. The term "cancer" includes premalignant, as well as malignant, cancers. The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal," as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "epigenetics" is defined as heritable changes in gene activity and expression that occur without alteration in DNA sequence. These non-genetic alternations are tightly regulated by two major epigenetic modifications: chemical modifications to the cytosine residues of DNA (DNA methylation) and histone proteins associated with DNA (histone modifications). Epigenetics refers to the changes of single genes or sets of genes.

The term "epigenome" reflects the overall epigenetic state of a cell, and refers to global analyses of epigenetic markers across the entire genome. Mapping epigenetic modification patterns or profiling the epigenome in a given cell can be used as epigenetic biomarkers for clinical prediction, diagnosis, and therapeutic development.

The term "epigenetic pathway" comprises any component that contributes to the "epigenome" or epigenomic state of a cell.

As used herein "endogenous" refers to any material from or produced inside an organism, cell, tissue or system.

As used herein, the term "exogenous" refers to any material introduced to an organism, cell, tissue or system that was produced outside the organism, cell, tissue or system.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like. As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Immune cell," as used herein includes any cell that is involved in the generation, regulation or effect of the acquired or innate immune system. Immune cells include T cells such as CD4+ cells, CD8+ cells and various other T cell subsets, B cells, natural killer cells, macrophages, monocytes and dendritic cells, and neutrophils.

A "T cell", also known as T-lymphocyte, or thymocyte is known in the art. It is a type of white blood cell which is primarily produced in the thymus. T cells are part of the immune system and develop from stem cells in the bone marrow. They help protect the body from infection and may help fight cancer. T cells can be distinguished from other lymphocytes, such as B cells and natural killer cells, by the presence of a T-cell receptor on the cell surface.

There are several subsets of T cells, of which each have a distinct function. In some embodiments, the T cell is a CD8+ T cell. The term CD8+ T cell is used interchangeably with the term CD8 T cell, herein.

The category of effector T cell is a broad one that includes various T cell types that actively respond to a stimulus, such as co-stimulation. This includes helper, killer, regulatory, and potentially other T cell types.

Antigen-naïve T cells (naïve T cells, $T_N$) expand and differentiate into memory T cells ($T_{MEM}$) and effector T cells ($T_{EFF}$) after they encounter their cognate antigen within the context of an MHC molecule on the surface of a professional antigen presenting cell (e.g. a dendritic cell).

Memory T cells are a subset of infection—as well as potentially cancer-fighting T cells (also known as a T lymphocyte) that have previously encountered and responded to their cognate antigen; thus, the term antigen-experienced T cell is often applied. Such T cells can recognize foreign invaders, such as bacteria or viruses, as well as cancer cells. Memory T cells have become "experienced" by having encountered antigen during a prior infection, encounter with cancer, or previous vaccination. At a second encounter with the invader, memory T cells can reproduce to mount a faster and stronger immune response than the first time the immune system responded to the invader. This behavior is utilized in T lymphocyte proliferation assays, which can reveal exposure to specific antigens.

Effector T cells describes a broad group of cells that includes several T cell types that actively respond to a stimulus, such as co-stimulation. This includes CD4+, CD8+, cytotoxic, helper, killer, regulatory, and potentially other T cell types.

An "exhausted T cell" ($T_{EX}$) is a T cell that instead of clearing an infection, tumor, or cancer becomes "exhausted" and unable to clear, alleviate, or reduce the infection, tumor, or cancer. An exhausted T cell can be a CD8+ T cell. An exhausted T cell can be a CD4+ T cell. Exhausted T cells have progressively lost T-cell function. "Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

"T-cell exhaustion", a type of immunosuppression, is characterized by deprived effector function, sustained expression of inhibitory receptors, and a distinct transcriptional state (Wherry. Nat Immunol. 2011, 12(6):492-9). T cell exhaustion comprises a state of impaired effector functions, high inhibitory receptor expression including Programmed Death-1 (PD-1, or CD279), transcriptional reprogramming, and defective immune memory (Pauken et al. Science 2016, 354(6316):1160-1165).

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

The term "infectious disease" refers to a disorder caused by pathogenic (micro)organisms such as bacteria, viruses, fungi, or parasites. Infectious diseases of the present disclosure include, but are not limited to a bacterium, virus, protozoan, mycoplasma, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, and *Trypanosoma cruzi.*

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The phrase "level of a soluble factor" in a biological sample as used herein typically refers to the amount of protein, protein fragment or peptide levels of the soluble factor that is present in a biological sample. A "level of a soluble factor" need not be quantified, but can simply be detected, e.g., a subjective, visual detection by a human, with or without comparison to a level from a control sample or a level expected of a control sample.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human, dog, cat, mouse, rat or transgenic species thereof.

The term "retrovirus," as used herein, is a member of the Retroviridae. A retrovirus is a single-stranded positive-sense RNA virus. In some embodiments, the retrovirus is an alpha-retrovirus, a beta-retrovirus, a gamma-retrovirus, a delta-retrovirus, an epsilon-retrovirus, a lentivirus or a spumavirus. In some embodiments, the retrovirus is a lentivirus selected from the group consisting of human immunodeficiency virus (HIV) and equine infectious anemia virus (EIAV).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "control T cell" refers to a T cell that is not an exhausted T cell. A control T cell can be, e.g., a $T_N$, $T_{EFF}$, and/or $T_{MEM}$. A population of control T cells refers to any combination of control T cells.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The terms "transfected" or "transformed" or "transduced" and the like as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "transplant," as used herein, refers to cells, tissue, or an organ that is introduced into an individual. The source of the transplanted material can be cultured cells, cells from another individual, or cells from the same individual (e.g., after the cells are cultured in vitro). Exemplary organ transplants are kidney, liver, heart, lung, and pancreas.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure provides improved cell therapy compositions for treating a disease in a patient, methods of making such compositions, and methods of treating patients having a disease with such compositions. In one aspect, disclosed herein are methods of making improved cell therapy compositions for treating a disease in a patient.

In certain embodiments, the methods of making improved cell therapy compositions comprise the steps of: (a) obtaining a sample comprising T cells from a subject; (b) altering a non-coding DNA sequence comprising a regulatory domain present in an open chromatin region (OCR) associated with expression of one or more exhaustion-specific genes in the T cells; and (c) engineering the T cells to target a therapeutically-relevant antigen, wherein the altered non-coding DNA sequence reduces or reverses exhaustion of the T cells. In certain embodiments, the sample comprising T cells comprises CD8+ T cells. In certain embodiments, the altering comprises knocking-out a regulatory domain present in an OCR associated with expression of one or more exhaustion-specific genes. In certain embodiments, the one or more exhaustion-specific genes is selected from the group consisting of t hymocyte selection-associated high mobility group box protein (TOX) and Zinc-finger type CCCH -containing 12C protein (ZC3H12C). In certain embodiments, the one or more exhaustion-specific genes is ZC3H12C, and the altered non-coding DNA sequence comprising a regulatory domain is an enhancer element located 15,358 bp (~15 KB) upstream of its transcription start site.

In some embodiments, the enhancer element is located on chromosome 11: 109948191-109949139, and the subject is human.

In certain embodiments, the methods of making improved cell therapy compositions comprise the steps of: (a) obtaining a sample comprising T cells from a subject; (b) altering a coding DNA sequence of one or more exhaustion-specific genes; and (c) engineering the T cells to target a therapeutically-relevant antigen. In certain embodiments, the sample comprising cells comprises CD8+ T cells. In certain embodiments, the one or more exhaustion-specific genes is selected from the group consisting of thymocyte selection-associated high mobility group box protein (TOX) and Zinc-finger CCCH -tvpe containing 12C protein (ZC3H12C). In certain embodiments, the exhaustion-specific gene is TOX and the altering comprises knocking out a single allele of a single allele of a protein-encoding ORF encoding the TOX gene in a diploid cell. In certain embodiments, the exhaustion-specific gene is ZC3H12C and the altering comprises knocking out part of a protein-encoding ORF encoding one or more exhaustion-specific genes. In certain embodiments, the part of a protein-encoding ORF comprises an exon.

Provided is an improved cell therapy composition comprising engineered T cells made by the process of any one of the previous embodiments. Also provided is a method of treating a disease characterized by increased numbers of exhausted CD8+ effector T cells ($T_{EX}$), comprising administering the improved cell therapy composition.

In some embodiments, the disease is selected from cancer and infection.

In some embodiments, the disease is a viral infection. In further embodiments, the viral infection is an acute viral infection or a chronic viral infection.

In some embodiments, the disease is an acute viral infection. In further embodiments, the acute viral infection comprises infection with a virus selected from the group consisting of hepatitis viruses, herpesviruses, polyoma viruses, anelloviruses, adenoviruses, retroviruses, and influenza viruses.

In some embodiments, the virus is a hepatitis virus selected from the group consisting of Hepatitis A Virus (HAV), Hepatitis B Virus (HBV), Hepatitis C Virus (HCV), Hepatitis D Virus (HDV), Hepatitis E Virus (HEV), GB Hepatitis Virus A (GBV-A), GB Hepatitis Virus B (GBV-B), and GB Hepatitis Virus C (GBV-C).

In some embodiments, the virus is a herpesvirus selected from the group consisting of alpha-herpesviruses, herpes simplex virus type 1 (HSV1), herpes simplex virus type 2 (HSV2), varicella zoster virus (VZV), beta-herpesviruses, cytomegalovirus (CMV), human herpes virus 6, human herpes virus 7, gamma-herpesviruses, Epstein-Barr virus (EBV), and human herpes virus 8.

In some embodiments, the virus is a polyoma virus selected from the group consisting of BK virus (BKV), JC virus (JCV), KI polyoma virus (KIPyV), WU virus (WUPyV), Merkel cell polyomavirus (MCPyV), human polyoma virus 6 (HPyV6), human polyoma virus 7 (HPy7), trichodysplasia spinulosa virus (TSPyV), human polyoma virus 9 (HPyV9), and MW virus (MWPyV).

In some embodiments, the virus is an adenovirus selected from the group consisting of adenovirus serotype A, adenovirus serotype B, adenovirus serotype C, adenovirus serotype D, adenovirus serotype E, adenovirus serotype F, and adenovirus serotype G.

In some embodiments, the virus is an influenza virus selected from group consisting of influenza virus A, influenza virus B, influenza virus C, and influenza virus D.

In some embodiments, the disease is a chronic viral infection. In further embodiments, the chronic viral infection comprises infection with HIV, HCV or HBV.

In some embodiments, the chronic viral infection is an HIV infection and the subject is being treated with antiretroviral therapy (ART).

In some embodiments, the chronic viral infection is a retrovirus infection wherein the retrovirus is selected from the group consisting of alpha-retroviruses, beta-retroviruses, gamma-retroviruses, delta-retroviruses, epsilon-retroviruses, lentiviruses, and Spumaviruses.

In some embodiments, the retrovirus is a lentivirus selected from the group consisting of human immunodeficiency virus (HIV) and equine infectious anemia virus (EIAV).

In some embodiments, the infection is a bacterial infection or a parasite infection.

In some embodiments, the disease is cancer.

In some embodiments, engineering the T cells to target a therapeutically relevant antigen comprises introduction of a recombinant T cell receptor capable of binding a desired antigen/MHC or neo-antigen/MHC combination or introduction of a chimeric antigen receptor capable of binding a desired antigen.

In some embodiments, the therapeutically relevant antigen is selected from the group consisting of CD19, PSMA, CAIX, HER2, CD30zeta, Folate receptor alpha, Mucin1 (MUC1), Hepatitis C virus E2 glycoprotein, HIV envelope glycoprotein gp120, CMV pp65, GPC3, CEA, Mesothelin, GD2, EGFR, PSMA, EpCAM, BCMA, IL-13R, FAP and CD20. In some embodiments, administration of the engineered T cell stimulates an antigen-specific immune response in the patient. In some embodiments, the patient is treated concurrently with another treatment, e.g., immune checkpoint blockade. In some embodiments, the immune checkpoint blockade comprises treatment with at least one immune checkpoint inhibitor. In some embodiments, the at least one immune checkpoint inhibitor is an anti-PD-1, PD-L1, CTLA-4, TIM3, B7-H3, BTLA, VISTA, CD40, CEACAM1/CD66a, CD80/B7-1, CD86/B7-2, OX40/CD134, CD40 Ligand, ICOS Ligand/B7-H2, 4-1BBL/CD137L, B7-DC/PD-L2/CD273, CD39/CD73, CD200/CD200R, LAG-3, TNFR2, KIRs, IDO, IL-10, IL-27, or TIGIT/CD226/CD112/CD122R/CD94 antibody. In some embodiments, targeting a high priority epigenetic pathway changes the epigenome of the engineered T cell. In some embodiments, targeting the high priority epigenetic pathway comprises epigenetic changes in at least one of Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. Targeting a high priority epigenetic pathway comprises knocking out transcription factors or other genes encoding proteins involved in creating, modifying or otherwise maintaining the epigenome. Targeting a high priority epigenetic pathway also comprises knocking out regulatory sequences in the OCR domains associated with T cell exhaustion.

$T_{EX}$ are epigenetically committed. Current immunotherapies such as PD-1 blockade provoke transient improvement in effector functions from these cells, but do not reprogram their epigenetics. As a result, the effect of PD-1 blockade is transient and these cells return to the "ground state" of exhaustion. A major problem that this invention solves is the identification of epigenetic pathways that are involved in establishing the epigenetic ground state of exhaustion and locking these cells into an inflexible differentiation state. This invention also solves the problem of identifying genomic locations that are epigenetically modified as part of the commitment to exhaustion. Targeting such pathways and/or genomic locations, alone or in combination with other immunotherapies, would prevent or reverse the $T_{EX}$ epigenetic commitment that limits current therapies. Drugs targeting epigenetic pathways are feasible and could be applied in many therapeutic settings. For cellular therapies, some epigenetic pathways identified could be targeted genetically. Proof of concept for at least one of these major pathways is provided. Tox is a member of the High Mobility Group of chromatin associated proteins. Demonstrated herein is a key role for Tox in the early programming and continued maintenance of T cell exhaustion. Tox interacts with other key epigenetic modulators, including the SET, RuvBl1/2 and DPY30 proteins, suggesting that Tox regulates a diverse array of epigenetic mechanisms. In addition to TOX, analysis herein also identifies Tox2, Stat1l, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39h2, Csprs, Sfmbt1, Hmgn3, Chd9, Rnf2, Ikzf3, Kmt2e, Satb1, Tet1, 2, and 3, Kdm5b, Sfmbt2, Actr6, Prmt7, genes encoding inhibitory receptors and/or T cell transcription factors, and other relevant T cell genes including PD-1, CTLA-4, LAG-3, Tim3, CD200/CD200R, Ptger2, Ptger4, T-bet, Eomes, Tox, Blimp1, BATF, AP-1 family members, IRF4, and other genes described in Wherry et al, Doering et al., and/or Crawford et al. (Wherry et at. Immunity 2007, 27:670-684, incorporated herein by reference in its entirety; Doering et al. Immunity 2012, 37:1130-1144, incorporated herein by reference in its entirety; Crawford et al. Immunity 2014, 40(2):289-302, incorporated herein by reference in its entirety) as potential targets. Other potential targets include, but are not limited to, at least one of SERTADI, XPA, HINT3, HIST1H1C, ZFP69, NR4A3, TNFAIP3, SAP30L, SPRY2, RYBP, TIPARP, YAf2, GCHI, GTF2B, PCGFS, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, HSPA1A, SP140, SPAG7, MYCBP, TRAPPC2, TCF4, RBL2, ALS2, IKZF3, IRF7, ELL2, MXD1, IRAK2, MX11, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. Indeed, additional work on Tet2 shows a key role for this enzyme involved in DNA methylation in T cell exhaustion identifying another high priority, druggable, epigenetic pathway for modulating T cell exhaustion.

Epigenetic Pathway

As described herein, an epigenetic pathway comprises any component that contributes to the "epigenome" or epigenomic state of a cell.

The term "epigenetic pathway" refers to a combination of signals or biological components that transmit such signals that together establish and maintain a stably heritable epigenetic state. In certain embodiments, an epigenetic pathway comprises a signal originating from the environment that triggers the start of the epigenetic pathway, an epigenetic initator that receives this signal and is capable of determining the precise chromatin location and or DNA environment for establishing a particular epigenomic state, and an epigenetic maintainer that sustains that particular epigenetic state in the initial and succeeding generations.

High Priority Epigenetic Pathway

The disclosure provides methods of treating a disease in a patient, the method comprising administering an engineered T cell to the patient, the engineered T cell comprising one or more alterations in one or more high priority epigenetic pathways. In some embodiments, the alterations comprise genetic modifications introduced via genome engineering approaches or epigenetic modifications using inhibitors or activators of epigenetic regulators. In some embodiments, the high priority epigenetic pathway is or has been targeted to reverse or prevent exhaustion of the T cell. In further embodiments, the high priority epigenetic pathway is or has been targeted to reverse or prevent exhaustion of the T cell. In some embodiments, the high priority epigenetic pathway has been targeted by genome engineering, e.g. by knocking out genes in the epigenetic pathway, or by modifying the function of protein encoding genes in epigenetic pathways. In some embodiments, the high priority epigenetic pathway is targeted by genetic engineering of the non-coding genome in locations that control expression of exhaustion-specific genes For example, there are exhaustion specific enhancers that are present in OCRs accessible only in exhausted T cells that are bound by a transcription factor that stimulates expression of one or more exhaustion-specific genes. Those exhaustion-specific genes may encode regulatory proteins (e.g., other transcription factors and the like), components of the epigenetic regulatory apparatus involved in the opening or closing of various chromatin regions (e.g., histone acetyltransferase (HAT) and histone deacetylase (HDAC)), or other genes essential to establish or maintain the exhaustion phenotype (e.g., PD1, TIM3, LAG3, TIGIT, CD39 and the like). See Wherry et al. *Immunity* 2007, 27(4):670-684; Doering et al. *Immunity* 2012, 37(6):1130-1144; Crawford et al. *Immunity* 2014, 40(2):289-302; Pauken et al. *Science* 2016, 354(6316):1160-1165, each of which is hereby incorporated by reference in its entirety. In some embodiments, the exhaustion specific enhancer(s) are deleted or modified, thereby changing the expression pattern of the exhaustion-specific gene(s). High priority epigenetic pathways are genes, loci, or proteins that fulfill one of the following criteria: a) are genes/proteins with a known or potential role in generating or changing epigenetic marks; or b) genes with known roles in T cell exhaustion based on transcriptional profiling studies that also have distinct epigenetic modifications in exhausted T cells. In some embodiments, the high priority epigenetic pathway comprises epigenetic changes in at least one of Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, Prmt7, genes encoding inhibitory receptors and/or T cell transcription factors, and other relevant T cell genes including PD-1, CTLA-4, LAG-3, Tim3, CD200/CD200R, Ptger2, Ptger4, T-bet, Eomes, Tox, Blimp1, BATF, AP-1 family members, IRF4, and other genes described in Wherry et al., Doering et al., and/or Crawford et al. (Wherry et al. Immunity 2007, 27:670-684, incorporated herein by reference in its entirety; Doering et al. Immunity 2012, 37:1130-1144, incorporated herein by reference in its entirety; Crawford et al. Immunity 2014, 40(2):289-302, incorporated herein by reference in its entirety).

Epigenetic Targets

In some embodiments, a target associated with an epigenetic pathway, or as used herein an "epigenetic target", is targeted within a cell. In some embodiments, the epigenetic target is at least one of Tet enzyme (e.g., Tet1, Tet2), an HDAC, Tox, Tox2, Csprs, Drud1, Sfmbt1, Chd9, Suv39h2, Sap30L, Hmgn3, BAZ2b, Prmt6, SET, Ruvbl1/2, DPY30, MLL proteins, Ezh1/2, PRC complex, CBP, BET, and/or p300. In some embodiments, the epigenetic target is at least one of any histone acetyl transferase, deacetylase, methylase, or demethylase, or any other epigenetic modifying enzyme or chromatin modifying enzyme. In some embodiments, the epigenetic target is an enzyme or intracellular protein capable of regulating epigenetic patterns. In some embodiments, the epigenetic target is a transcription factor. In some embodiments, the epigenetic target is a cell surface protein that regulates a downstream epigenetic pathway. In some embodiments, the epigenetic target is a cell surface protein that regulates a downstream epigenetic pathway. In some embodiments, the epigenetic target is at least one of SERTADI, XPA, HINT3, HIST1H1C, ZFP69, NR4A3, TNFAIP3, SAP30L, SPRY2, RYBP, TIPARP, YAf2, GCHI, GTF2B, PCGFS, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, TOX, HSPA1A, SP140, SPAG7, MYCBP, TRAPPC2, TCF4, RBL2, ALS2, IKZF3, IRF7, ELL2, MXD1, IRAK2, MXI1, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. In some embodiments, the cell is a T cell. In some embodiments, the cell is an exhausted T cell.

Transcriptional Targets

The epigenome provides the context in which transcription factors function. Although global epigenetic landscape information was not previously fully characterized for exhausted T cells, studies of the Pdcd1 locus (which encodes PD1) have been informative. Analysis of the Pdcd1 promoter region in acutely resolved LCMV infection demonstrated that these regions were largely demethylated in the effector phase and then became remethylated as infection resolved and CD8+ T cell memory formed. By contrast, the Pdcd1 locus became completely demethylated in chronic LCMV infection and no remethylation was observed, even when viral titers and PD1 protein expression by exhausted CD8+ T cells decreased (Youngblood et al. Immunity. 2011, 35(3):400-12). Similar data were obtained in studies examining well-controlled HIV infection (Youngblood et al. J Immunol. 2013, 191(2):540-4133). The present disclosure teaches that T cell exhaustion is associated with an epigenetic and transcriptional profile that is separate and distinct from that seen in non-exhausted T cells.

In some embodiments, a transcriptional target associated with an epigenetic pathway, or as used herein a "transcriptional target", is targeted within a cell. In some embodiments, the transcriptional target is an exhaustion-specific gene. In some embodiments the exhaustion-specific gene is a transcription factor. In some embodiments, the transcriptional target is a promoter or enhancer sequence that is bound by an exhaustion-specific transcription factor. In some embodiments, the transcriptional target is Tox, SET, RuvBl1, RuvB12, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, and/or Prmt7 In some embodiments, the transcriptional target is at least one of SERTADI, XPA, HINT3, HIST1H1C, ZFP69, NR4A3, TNFAIP3, SAP30L, SPRY2, RYBP, TIPARP, YAf 2, GCHI, GTF2B, PCGFS, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, HSPA1A, SP140, SPAG7, MYCBP, TRAPPC2, TCF4, RBL2, ALS2, IKZF3, IRF7, ELL2, MXD1, IRAK2, MXI1, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. In some embodiments, the transcriptional target is at least one of Pdcd1, Ccr7, Gzmb, Lef1, Itgam, Itgax, Itgad, Cd44, Kcnj8, Lac9/Rtn1, Ifng, Tbx21, Cxcr5, I110, Nlrc3, Cd200r, and/or Atp8b4. In some embodiments, the transcriptional target is A330093E20Rik, Rnf19a, 2010010A06Rik, Cdh23, Abtb2, Dync2li1, Lrrc1, Scn1b, Manla, Gimap3, Lef1, Co126a1, Gpr180, Fam126a, Wdyhv1, Mir6395, Gpr34, Fcgr1, Rpia, A430107P09Rik, Hbsl1, Slc35b3, Tmem248, Cox7a21, BB019430, Pde5a, Sept7, Lrrc3b, Cd101, Znrf3, Znrf1, Gm6260, Prpf40a, Ets1, Scn3a, Kremen1, Fam210a, Trpm1, Pip4k2a, Trnp1, Sel1, Nfia, Lipa, Zc3hc1, Msgn1, Yeats4, Abcd2, Tbcld1, Kcnh8, Zfp407, Capg, Gm7538, Rgcc, Sh3bp5, Slpr1, Zfp957, Mcur1, D16Ertd472e, Trat1, Fam107b, Mbtps1, Egr3, Palm3, 9030624G23Rik, Ppp6r1, Ckap4, Rngtt, Crtc3, Peak1, Lhx2, Btg1, Serbp1, Cd2, Acox1, Hormad2, Gm10684, Smo, A630075F10Rik, Ndst1, E030018B13Rik, Skpla, Kcnh8, Nck2, Frmd7, Cldn10, Peli1, 2010300C02Rik, Ins15, Supt20, Slc4a4, Rph3a1, Dip2c, Pm20d2, Nsg2, Rbm26, Tpk1, Stambpl1, AF357399, Car2, Mir145b, Zfp592, Galnt4, Gm5083, Thnsl1, Dhx40, Gm20098, Ly6i, Sugt1, Ywhaz, Rad23b, Bcor, Gm12159, Vegfa, Cacna1b, Arhgef11, 2210408F21Rik, Mett18, Wdr73, Usp12, Art4, Clvs1, Mir6388, Diap2, Gm10532, Msi2, 4930546C10Rik, Mbnl1, Tm6sf1, Ppp2r5a, Mageb16-ps1, Neurl1b, Sspn, Suv420h1, 2410088K16Rik, Rg12, Timm8a2, Aebp2, Mam12, Ldhal6b, Peak1, Parp2, Apbb2, Tctexld1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efcc1, Malat1, 4931403G20Rik, Tox, Arpc3, Atg10, Gpbp1, Gm5148, AI317395, Abhd2, Celsr1, Tsen2, Pfkfb3, Cyc1, Mir378c, Slamf6, Btg1, Phf2, Cxcr4, Gm10789, At12, 6030407003Rik, Ggnbp1, Angpt1, 9530077C05Rik, Basp1, Rapgef6, H2-Ea-ps, Fam214a, Ppfia4, Lta4h, Ets2, Slc29a1, Xpo4, Gramd3, Itfg3, Fli1, Frmd6, Rbp1, Olfm13, Peli1, Srpk1, Hmgcs1, Irf2bp2, Cxxc5, Ccdc171, Cntnap2, Fance, Cb1b, Cubn, Sfmbt2, Srsf3, Pepd, Dgkd, Osbp16, Trib2, Zfand3, Dchs1, 5430421F17Rik, Fpr3, Dap11, Trat1, 0610040J01Rik, Gm14005, BC051019, Tank, Tnfsf11, Rara, Pik3c2a, Elmo1, Nck2, Bcl2l11, Fam78a, Gm10638, Prkcq, Gpr126, Bach2, Ttc30b, Nlk, Ube2e2, Usp3, 4932441J04Rik, Larp4b, Serbp1, Dbn1, Vav3, Derl1, H2-T23, C130021I20Rik, Fbx114, Ets1, Fgf8, Ab12, Acvr1b, Upk1b, Efcab10, Uch13, Cd302, Cdc40, Nsg2, Tmem222, P2ry10, Klrb1b, Mc1r, Car8, BC048403, Taf8, Atplb1, Mir30c-2, Luc712, Erbb4, Arhgdib, Ube2h, Itpr2, Vav3, Ptgfrn, D630010B17Rik, Eif2s3x, Vav3, Nfe213, Ccdc171, Fignl1, 4930519F09Rik, 1700123O12Rik, Acsf2, Ndufb9, Atp7a, Upp2, Ptpla, Man1a, Rgs3, Zbtb2, Trib2, Npr1, Fez2, Tle4, Fuca1, Cmip, Bcap29, Syne1, Dmbt1, Ell, Blnk, Sepw1, Gltscr1, Erdr1, Med131, Moxd1, Btg1, Akap6, 1810053B23Rik, Rsu1, Gprasp2, Art4, Gpd2, Tmlhe, A430107P09Rik, Kcnj9, Atp8a1, Adam6b, 2010109I03Rik, Spred2, Raver2, Ap1m2, Dclre1a, Rbp7, Gcc1, Traf4, Satb1, Gm5538, Il12a, Fam60a, Thrb, Elk3, Vps45, Tle4, Akap13, Gprin3, Sox21, Emp1, Wfdc2, Slc45a1, Lnpep, Rapgef6, Txn2, Frmd4b, Myoz3, Zfp870, Bc16, Mvb12b, Ntrk3, Spaca1, Mir701, Cdca7, Gm5083, Slpr1, Spry4, Cck, Il6st, Hebp2, Slc43a2, Tdrd5, Gm5833, Mir7-2, Mir1931, Pdgfb, 1700052N19Rik, Nfkbiz, Gm20753, Hapin1, Rras2, Diap2, Manba, Cers6, Rasgrp1, Lnpep, Apin, Ephb2, Arpp21, Mica13, Chic2, E130114P18Rik, Ipcef1, Dyrk2, Bach2, Mir122a, B230206H07Rik, Ceacam9, A730006G06Rik, 4930542C21Rik, A430107P09Rik, Trat1, Ccr2, H2-Ob, Adm, Yeats4, Ccne1, Gpc5, Spsb1, Jrk1, Orc4, Camkmt, Nfia, Celf2, Gadd45a, Gtf2a1, Nrde2, Nipa2, Rmi2, Lcor, Btg1, Atg10, D6Ertd527e, Ccm2, Dpys12, Dirc2, Cpm, Arhgap15, A730043L09Rik, Raph1, Cst10, Slc7a13, Ramp1, Atplb1, Zfp120, Slc39a13, Zfp706, Agr2, Tagap, Mir3110, Ubash3b, Dnmt3aos, H2-B1, Agbl1, Smc6, 1700060C20Rik, Trib2, A930005H10Rik, Btg1, Scm14, Mir196b, Efna5, Tmeml4a, Kcnj15, Snrpd3, Nnmt, Ryr1, Ptk2, P2rx4, 5830428M24Rik, Commd3, Cd28, Hspb11, BCO21785, Tcf7, Cstb, Art4, Tet3, Map3k13, Camkv, Ralbp1, 9330175M20Rik, Tgtp1, Selt, Irgc1, Tcf7, Tet1, Bnip31, Nrbf2, Nimlk, Rfx8, Th6, Grik1, Tox, 1700061G19Rik, Dhrs3, 4930519G04Rik, Mid1, Aplar, Basp1, Aqp4, 4930415F15Rik, Aif1, Rnf125, Fam134b, Atp13a3, Dmbt1, Mbnl1, Nfam1, Lmo4, Znrf1, Ambp, 4930523C07Rik, Bfsp2, Zfp592, Gm2447, Gm16157, Gjd3, Tgtp1, Ston2, Lypd6b, Rnf7, Zbtb2, BC051537, 4930417O13Rik, Arnt1, Ttc9b, Foxp1, Mir7219, Mrgprb5, Tnik, Dhrsx, Foxp1, Tubb2a, Cyb5r2, Itga4, Snx9, Fam65b, C78339, Mir7212, Ldlrap1, H2-Oa, Snx12, Tdrp, Mndl-ps, Foxp1, Gucy2c, Creb1, Scn4b, Irf4, Rftn2, Gpr125, Dpf1, Fam134b, Akap13, Tmem108, Suclg1, Mn1, Sema4b, Gm6682, Slc46a2, Dennd3, Bach2, Syt12, Grh13, Smad3, 1600014C10Rik, 4930455C13Rik, 3200001D21Rik, Nup153, Grk6, Zfhx3, Fhit, Hmg20b, 4930564D02Rik, Bach2, Slc39a3, Urad, Smcla, Maml1, Zadh2, 8030462N17Rik, Fsbp, Tmem243, Srp14, Lix1, Tmc1, Tspanl1, Tns1, Serpinb5, 1810026B05Rik, Smad7, Mir3108, Phxr4, Tmem131, O1fr1507, Kidins220, Mir378c, Afap1, Rere, Sin3b, Efemp2, Neto2, Mir7669, Tgtp1, Gramd3, Map7d2, Chst2, Sp110, Ccdc162, Igflr, Mir3110, Dcdc2b, Dse, Dlgap2, Armc9, E230029C05Rik, Gm11944, Tnik, Kat6b, Nkiras1, Tbce1, B4galt1, Cd2ap, Tnks, Icos, Tanc1, Sik1, Tor1aip2, 4930453N24Rik, Bnip1, Gm6313, 4930415F15Rik, Inpp5a, Atoh7, 2210417A02Rik, Pdss2, Lamtor3, Ptbp2, Ostm1, Nrarp, Fry1, Mir1907, Gm10638, Sumo1, Zfp60, 1600014C10Rik, Haao, Syde2, Ep300, Ndrg3, Tex2, Cdx2, Eefsec, Tmem131, Mir6959, Fyn, Prkcq, Mica13, Snhg7, Ambra1, Rag2, Vdac1, Ptp1a, Tram1, Aak1, Pebp4, Sgpp1, 2410007B07Rik, Itpr2, Tulp2, Mir6395, Elovl6, Ppplr3b, Zc3h4, Sptbn4, Rap1b, Vg114, Kcna2, Cnot6, Tbcld1, Pde4d, Rapgef4, Fbxo47, Proca1, Aim, 2310001H17Rik, Tmem131, Sh2d3c, Gtpbp8, 1700030C10Rik, Polr3b, Fam69a, Bcan, 4930465M20Rik, Sbp1, Emg1, Aaed1, LOC102633315, 5930430L01Rik, Ads1, Foxp1, Gm20337, Trdmt1, Gm9920, Foxo1, Olfm13, Fyb, Pgpepl1, Nsg2, Tex26, Fancc, Cngb1, Rapgef2, 2010010A06Rik, 2410007B07Rik, Lbh, Pnrc1, Lad1, Mycn, Abhd15, Cd1d2, 4930428G15Rik, Hnrnpl1, Dnaja2, Ccr7, Mmp15, Neto2, Bach2os, Efr3a, Rnf41, Mir7656, Znrf3, Rtkn2, Sesn1, Zp3r, Glrp1, Kdm7a, 3200001D21Rik, Pdss1, 5730403I07Rik, Mmp15, Thrb, Zbtb16, Vkorc1, E330009J07Rik, Dntt, 4933406J10Rik, Sim2, Lgals9, Gm12216, Grb10, Ednra, Fam3c, Birc6, Bace1, Sfrp2, 2010107G12Rik, Zfp184, Ctso, Zfp462, Abcb1a, Gm6639, Mir1258, Dyrk1b, Ra1b, Thrb, S100a6, Gm590, Dnajc1, Zfand3, Blm, Ikzf2, Lrrc32, Nsg2, Foxp1, Tnpo1, Zfat, Specc1, Snora75, Vps45, Acp6, Syde1, Ext13, Fbx114, Cdh26, Celf2, Cd2, Tshz2, Cntln, Fam65c, Dad1, Akap6, Gm15880, E330011O21Rik, Kdf1, Gstt1, 2700046G09Rik, Sort1, Nyap2, 1700063O14Rik, Cog6, Extl1, Vmn2r96, I112b, Lclat1, A430107P09Rik, Zkscan16, Chl1, Nck2, Cdy1, St6gal1, Mir21c, 2810428I15Rik, Cnr2, Rab44, 1700064J06Rik, Zfp191, Peli1, Als2c1, Gnas, 2300005B03Rik, BC033916, Cd226, 1700049E22Rik, Nipal1, Gimap6, Gm5086, 8430436N08Rik, Ift80, Zfp697, Svs1, 4930459C07Rik, Epcam, Zfp706, Pde11a, S1c43a1, S1c9a9, Tshz2, Fbxwl1, Mir7046, Zpbp, 1700123O12Rik, Slcl6a1, Gm7457, Tcf4, Fbx112, I19r, Galnt6, Gm5868, Panx1, Hs3st5, Jarid2, Phxr4, Dock2, Nrip1, Lasp1, 1700066B19Rik, Marcks, Plekha7, Wdr41, Pdss2, Gpr83, Rapgef4, Gm15910, Colq, O1fr1507, Vg114, Fgfr1op, Fanc1, Capn1, Lonp2, Rnf38, Gpaa1, 1700016G22Rik, Vmn2r98, Gm7325, Gm826, Rp131, Klrc1, Ikzf1, Crlf3, Cd44, Gypc, AU019990, Fbx113, Tsc22d3, Tgm2, Ptpn14, Fancc, Arhgap26, Tgfbr2, Klf2, Sept7, Ptprc, Btn2a2, 4921511I17Rik, Ppp2r5a, C78339, Arhgap39, Ism1, Mpz12, 2810459M11Rik, Dyrk2, Tspan13, Fbx114, Plat, Celf5, Susd3, Rps6ka2, Gtf2ird1, Naif1, Rsph3a, Tssc1, Ext1, Snora7a, Bc12111, Pip4k2a, Np1, Tmem236, Cox7a21, A530013C23Rik, Rgl1, Pgk1, Ift80, Emid1, Inpp4b, Cldn10, Gls, Tnni1, Folr4, Gm5766, O1fr1507, Hpcal1, Cyth4, St8sia6, 5430434I15Rik, Ropnl1, Serinc1, Mad211, 4921525009Rik, A430107P09Rik, Gm11127, Tra2a, Urb2, Pgpepl1, Cacnald, 5730403I07Rik, Fam49a, 1700025F24Rik, Stat1, Calm1, Kcna7, Eif1, Mir669m-2, Kdr, 1700123O12Rik, Mir8099-2, Hspa8, 2010010A06Rik, Zfp53, 4930524O05Rik, Abl1, Uvrag, Slc16a1, Dnah7b, Golph3, Ipcef1, Usp3, Jun, Snord89, Tcf7, Rbpms, Folr4, Papss2, Spred2, Stpg1, Mgat5, Lpin1, D8Ertd82e, Dhx40, Slit3, 4933405E24Rik, Nsun6, A430107P09Rik, Apo17e, Raly, Celf2, Ndufs7, Mir6921, Kbtbd11, Gc, Haao, Gm9054, Slc44a3, Tnfrsf19, Lef1, Ankrdl1, Plxdc1, A430107P09Rik, Zcchc2, Zmat4, Jun, Adamts14, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stk17b, Ceacam9, Ttc1, E130006D01Rik, Camkmt, Ankrd63, Agtr1b, Khdrbs1, Zfp706, Cux1, 4922502D21Rik, Btbd1, Timm8a2, Itga4, Reep2, Uvrag, Cyfip2, Elovl6, Tfeb, Spag16, Tbce1, Lmo2, Rasgrp1, Fam86, Ktn1, Fbxo32, Gata3, Ly86, Ptgs2os2, Fam111a, Lac16a, B430306NO3Rik, Tff3, Kcnn4, Mtif3, Ldlrap1, Tmem260, Pla2r1, Basp1, Ncoa3, Ngly1, Ccdc162, Nhs12, Cdc123, Hnrnpu, Arhgap18, Zf12, Gm6498, Bex6, B630005N14Rik, Dynit1b, Lypd6b, Clec2e, Rbm17, Pst-pip1, Lrp12, Akap2, Camk2d, Igflr, Atpla1, Gsn, Rragd, Actn1, Odf3b, Nudt4, Vmn2r99, Parpl1, Adipoq, Fam221a, I16ra, Kif23, Fabp5, Srpk2, Ikzf1, Fbxw7, Slamf9, St6ga11, Vav1, Serbp1, Reep1, Agr3, P1c12, Kcnj15, Aebp2, Gm20139, Mtx2, Sell', Mbn12, A430078G23Rik, Krr1, Lclat1, Zfp438, 4930487H11Rik, B4galt1, Ifngr2, Olfr221, Asb4, Gm6793, Aplm1, Pdlim5, Gltscr1, 1110032F04Rik, Ankrd13a, Abcd2, Iqsec1, Inpp5a, Pdzrn3, Akirin2, Pip4k2a, Dyrk2, Jun, 4930465M20Rik, Osbp19, Ttc30a1, Ctnnbl1, Tmem243, Olig3, Ubtd2, 4930540M03Rik, Dnajc5b, Denndla, Gadd45a, Rp18, Dap11, Cd2ap, 6430710C18Rik, Slc16a5, Rcbtb2, Hmgxb3, A630075F10Rik, Ankrd2, St8sia1, Ptk2b, Paqr8, Tox, Wdr37, Stat4, Rplp1, Ccnj, Hspbp1, Mthfdl1, Zcchc9, Gm13293, Camk4, Htt, Usp10, Plekha6, Gm5617, Cnksr3, Mir7218, Lcp2, Cd28, Lbp, Ncoa3, Ski1, Hey1, Mir6368, Akap6, Spin1, Ccdc174, Stambpl1, Ggta1, Pifo, Stim2, Rras2, Tomm201, Gm5538, Skap2, H2-Ob, Zfp3612, Clec2d, Erdr1, Dapl1, Vasp, Cytip, B4galnt3, Hamp, Mex3b, Tcf712, Vps13d, Alox5ap, Mtss1, Gm7457, Fam46a, Taf3, 2810408111Rik, Ms4a7, Mad211, Selt, Snrpf, Hcn2, Frmd4b, Hivep1, Tspan13, Nfia, Asap1, Nt5e, Misp, Mam12, Sh3pxd2a, Ccdc162, Setd7, Etohi1, Acvr11, Fntb, Shank3, Rhoh, Prok2, Marcks, A830010M20Rik, Ywhaz, Mtss1, Gm8369, Fam188b, Atp2a2, 4933405E24Rik, 4932443I19Rik, Notch2, Zc3h12b, Numb, Neb, Ramp1, Zfp831, Impdh2, Grk1, 4930459C07Rik, Mir7035, Setd3, Cdc42se2, Spol1, Fam166b, Mir6419, Atp10d, C2cd5, 4933412E24Rik, Bol1, Calr4, I122ra2, Slc22a16, Syde2, Fyn, Slc27a6, Stx3, Gm6313, Rbm18, Gm13293, Tbc1d8, Fabp5, 4930546C10Rik, Slc16a1, Cnr2, Kcnip2, Trim69, Agbl1, Plvap, Ms4a6c, Usp38, At12, Sh3kbp1, Ppfibp2, Pim1, Pmis2, Sh3pxd2a, Ms4a4c, Klf3, Cb1b, Mir701, Dmwd, Mtss1, Cdk13, Cabp2, Chdh, Pde4b, Ston2, Cmah, Fbx114, Syk, Trio, Btg1, Ski, Cnot2, Stk38, Tm9sf3, 4930482G09Rik, Parpl1, Jarid2, Mam13, 6430710C18Rik, Commd9, Fhit, Scampi, Tcf7, Ncf1, Ric8b, Gm3716, Scm12, Nr2f2, Ssr1, Il6st, Ankrd50, Pnma12, Foxp1, Raver2, Ccdc64, 8430436N08Rik, K1f13, Itga5, Commd3, Mro, Ms4a7, Rock2, Enc1, Rab3gap1, Nav2, Tlr1, Gm7457, Elfn1, Rp134, Agfg1, 1700020N01Rik, Irf4, Gm8369, O1fr1507, Grik4, Akap6, Mir6387, Thrb, Gm20110, Mir7670, Bag4, Gm15441, LOC101055769, Pak1, Mbd2, Ralgps2, Lipg, Gpnmb, Ubash3b, Kntc1, Aqp9, Znrf2, Cmah, Peli1, Chd7, Tmsb4x, Copb1, Gimap1, Bcaslos2, Ppapdc1b, Cdcl4a, Ier5, Susd3, Birc2, Sun2, Itga5, Rlbp1, St8sia1, Hectd1, Chn2, Bcaslos2, Slc39a11, Cdc7, Me3, Stk17b, Ccr4, Peli1, Cd226, 2510009E07Rik, Sh2d1a, Zfp2, Mei4, Chst2, Nipal1, Tbce1, Itgb6, Tmed10, Gm4489, Tmcc1, A430107P09Rik, Abtb2, Tgfbr3, Zfp704, Reep5, Apcdd1, Pik3r1, Ms12, Gm20098, Eif4e3, 5430402O13Rik, Tssc1, Lphn2, Kcnh8, 4921525009Rik, Fam46c, Pum2, Itsn2, Slc11a2, Usp6n1, Gimap6, A430107P09Rik, Nipb1, Nrxn3, 1700042O10Rik, Capn3, 4930526115Rik, Plat, Gm15850, Dock10, Shisa2, Wbscrl6, Egfl7, Zfp957, Gm20110, Slc4a8, Ago2, Pnp2, Tgfbr3, Hmga2, Pdlim7, Dip2c, Atplb1, Pxk, Snora26, Gm6498, Sema3d, 3300002I08Rik, 9330175E14Rik, BB123696, Fibcd1, Slc6a19, S100a6, Commd9, Lpar4, Cntn5, Nr1i2, Panx1, Dock2, Ptov1, 5330411J11Rik, Sec24d, Ms4a4b, Eif3g, Rsbnl1, Plxnc1, Jarid2, 1810041L15Rik, Diap2, A630075F10Rik, Klf13, Tlk1, Lef1, Slc4a4, 2610020H08Rik, Tbce, 9430014N10Rik, S1c16a10, 2310042E22Rik, Lrrc3b, St6gal1, Tnfrsfla, U90926, Fam134b, Grxcr2, Dok5, Aldh8a1, Cybrd1, Smarcb1, Jmy, Zfp608, Cdkn2aipn1, Aire, Prps2, Gm839, 4933412E24Rik, St6gal1, Ube2d2b, Mab21l1, Slc23a2, Keap1, Brdt, Piwi12, A930005H10Rik, Fyb, Ncald, Lgals9, Zfp704, Dguok, Gm15706, Nr3c1, Med13, Rictor, Paxbp1, Mir1903, Sv2a, Slx1b, Tbc1d24, Wnt5b, Ccr7, Ptk2, Mir21c, Aox4, Slc35b4, Mgat5, Zfp281, Mycn, 1700016G22Rik, Odc1, Prkcb, Ate1, Ncbp1, 3300002108Rik, Ly6d, Spag16, Clk1, Atg10, 1700030L20Rik, Nsg2, Agps, Golt1a, Cntn5, Cadm4, Malsu1, Frmd4b, Gm6607, Cdh23, Gramd4, Slc44a2, Limd2, Lphn2, 1700010K23Rik, Lrrc66, Akap7, Peal5b, D030024E09Rik, Zscanl0, Lsm2, Kcnj13, Cdhr3, Fbx117, Lhx2, Olfm2, Cyp2r1, Wisp3, BB123696, Nlrc4, 2010010A06Rik, Elov16, Eea1, Mir1907, Gls, B4galnt3, Epb4.1, Tshz1, Gpr126, Rgmb, Ncs1, Tet1, Hoxa1, 4930515G16Rik, Usp33, Stk10, K1h16, Ccdc109b, Manba, Gm5111, Chst15, Runx1, Rgs3, Gm4759, Ldlrad4, 4933400F21Rik, 4933406C10Rik, Diap2, Mir6403, Plin2, Zmiz1, Mam13, Fam86, Hbsl1, Inpp4b, Gm14405, Mgat5, Cntn5, Ramp3, Ifnk, Pgm1, Mfsd6, Armcx1, Mir5127, Gimap6, Mir6387, Slc38a2, Gsdmcl-ps, Cd24a, Kmt2e, Csrp1, 9530052E02Rik, Stk17b, Fyb, Lhfp15, Atp8a2, Amn1, Sertad2, Epb4.112, Stk24, Cdk17, Camk4, Rpa1, Zmyndl1, Efcab11, Mir491, Zc3hc1, Vps45, Rgs3, Ube2m, Tspan5, Insr, Snapc1, Btg1, Cox10, Znrf1, Camk4, Ddr1, Gm11981, Sesn1, Commd8, Nrip1, Polr3k, Eya3, Ppplr1b, Pcdh7, A430107P09Rik, Efcc1, Mtss1, Hpn, Armcx1, Gm20139, Alg14, Sec1la, Cyb5d1, Trpm1, Fam65b, 5730508B09Rik, Frmd4b, Gm10584, Gm5069, Pmepal, Sell, Mir6413, Klf12, Rhoq, Plc12, Prrc1, Emp1, D030024E09Rik, Rnf145, Bach2, Prkcq, Hic1, Msmo1, Map3k7c1, AI854517, 4922502D21Rik, Vti1a, Zcchc9, Spats2, Mir7681, Wdr89, Bc16, Cytip, Gm13293, Creb314, Peli1, Pak1, Efcab11, Usp7, 4931403G20Rik, 1700030A11Rik, Mvb12b, Ampd3, Cubn, Baiap3, Med30, Actb12, Kat6b, Peli1, Tmevpg1, Nsf, Hpcal1, Ube4b, Fam110b, C330011F03Rik, Inad1, Sesn3, Tmem30c, Itgb6, Dlg1, Srp14, 3300005D01Rik, Ggact, Mir21c, Cyp2s1, Mir7061, Bach1, Insr, 2410114N07Rik, H2-Eb1, Tasp1, Tusc3, Irf2bp2, 1700056E22Rik, Ppp6c, Slain2, Cnn3, 6030407003Rik, Acbd6, Hmgb1, P2rx4, Cdk19, 1700061G19Rik, Tesk2, Plxnc1, Ercc3, 2010010A06Rik, Stk17b, Tspan9, Kcnj16, Ddx10, Wnt16, Sp4, Hilpda, Slc38a6, Tgfbr2, Fggy, Sugct, Begain, Mnd1-ps, Ksr2, Eif2d, Ms4a4d, Stim1, Cst10, Nfatc1, Ppifos, Gng7, Mir211, Txk, 4930415F15Rik, Tmem64, Stim1, Pip5k1b, Kcnj15, Commd8, Mir3108, Atp11b, Stk17b, Emc3, Cldn10, Akap13, Abcb1a, Mthfdl1, Foxk1, Rgs3, Gdnf, Micu1, I17r, Arhgap35, Olfr1364, Ms4a4b, Rgs10, Flt3, Sfrp2, I19r, Sf1, Gm1604b, Galnt4, Dtnb, Supt20, Fntb, Zmyndl1, Tulp3, 2410007B07Rik, Tsen15, Abhd2, Dgcr6, Filip11, Ift81, 4933401D09Rik, Gtdc1, Ano6, Mir1928, Peli1, Jak1, Cdk19, Syne1, I123r, Tpm2, Fam65b, Kidins220, Vav1, 9030617003Rik, C1q13, Ceacam9, Ehd2, Vtcn1, Dusp7, Pik3ip1, Ostm1, Ppard, Olfr372, Mir7032, Npy, Phxr4, Grap2, Thrb, Wipi1, Dock4, Mfsd6, Zmynd8, Mylip, Setx, Ccdc146, Il12a, Sal13, Mir7048, Hapin1, Casp3, Bbs9, Syne1, Tdrd3, 4930565D16Rik, Gm20098, Tcf4, Haao, Snd1, Zfp706, Agfg1, Gm8709, Syne1, 4933406J10Rik, Pik3c2b, Manba, Olfr1033, Aurkb, 9330175E14Rik, Foxo1, Sfmbt2, Bach2, Pogz, 4930459C07Rik, Phxr4, Map7d2, Gm20750, Il12b, Sesn3, Psen2, Suco, Mad211, E030030I06Rik, Gadd45a, Abca1, Boll, 4930430F21Rik, Cstad, Lyst, Rasgrp4, 4833427F10Rik, Ehd2, 4930445N18Rik, Ppm1h, Gltscr1, Irf8, Lgi1, Gm10432, H2-M101, Crtc3, 4930453N24Rik, Irs2, 1700042O10Rik, Rabgapl1, Rnf144a, Csk, Rpia, A430090L17Rik, Mir8097, Serbp1, Mir684-1, Tcf4, Commd8, Tet3, Nr1i2, Gm10190, Prkcq, Orai2, Dpy30, Sbk2, Tssc1, Cd5, Sipal12, Dcpla, 1810006J02Rik, Itgae, D030025E07Rik, Wibg, Bach2, Irf4, Ctnnd1, Usp7, Rftn1, Themis, 4930440I19Rik, Thrb, Nr1d2, Tgtp1, Ccdc162, Atp8b2, Speer4f, Stra8, Gm4906, Fam46c, Pag1, Etv3, Erdr1, Dhrsx, Fam65b, Gosr1, Trem2, Fbln1, Sp3, Mef2a, Bcor, Map4k4, Magi2, Pak2, Rph3a1, Lgi4, Pja2, Tceal3, Efcab11, Arhgap5, Ext1, Smyd3, Prim2, Satb1, Stag2, Themis2, Pim1, Apol8, Lrrc6, Shb, Magi2, Commd8, Zfp879, Trp53il1, Rgl1, Abcd3, Diap2, Zbtb2, C030016D13Rik, Arhgdib, A630075F10Rik, C730036E19Rik, Phc2, Adamts10, Inpp4b, Cd200, Itpr2, Fgfr1, Gm5434, Scn2b, D8Ertd82e, Gm2a, Ube2v1, Bend4, Lpp, Mir181a-2, Gm13293, P2ry1, Klf7, E030018B13Rik, Rhobtb2, Ddr1, Ggnbp1, Gimap7, Mamstr, Cmip, Setbp1, Fcgr4, Slc1a3, Zfp608, 2810403A07Rik, Gm7538, Mir378a, Hoxa13, 2610301B20Rik, Ngly1, Sergef, Tpp2, Slc35b3, Mam13, Nav1, Txk, Fam195a, Scm14, T1r12, Gpr125, Zfp3612, Suclg2, Tec, Akap2, Rab38, C030018K13Rik, 4933433H22Rik, Osbp111, Capn13, Ankrd50, Mir1928, Mir3108, Slc39a10, Dock2, Dip2c, Aebp2, A530046M15Rik, Gm6251, Mtx2, Exoc4, Olig3, Dph6, Emb, Xpc, Gm7538, Tnfsf8, Afap112, Cenpv, Gsn, Rbms2, E2f3, Smarce1, Foxp1, Slc37a3, Apbblip, Tex10, Bend4, Pcgf5, Trio, Klf5, Gja8, E130006D01Rik, Ncor2, Acbd6, Alg14, Scmh1, D830013O20Rik, Galnt4, Ndufa6, Timm8a2, 2210010C04Rik, 4931403E22Rik, Gys2, G630090E17Rik, Dap11, Nup160, Fxyd7, Zscan18, Bid, Serh1, Cdk17, Lrtm2, 3930402G23Rik, Tm2d1, Snora7a, C8g, Nkap, 2410007B07Rik, Ilf3, Mir7017, Gpr83, Thada, Ambra1, Fancc, B3galt4, Thnsl1, Etv5, Aox2, Tgm2, Manla, Edem1, Hnrnph1, Atp6v0e2, Clec4f, Hey1, Fam3c, Stat4, Slc46a1, Rps15a-ps6, Kdm4c, Upb1, Sik1, Nceh1, Prkcq, Btg1, Galnt2, 2010010A06Rik, Neu3, Cubn, Mir1928, Rapgef2, Nedd41, Egfl7, B3gnt2, Tgtp2, Gm13546, Ext1, Pold4, Ggact, B3gnt7, Gm5868, Tlr7, Lefty2, Npff, Tcf712, D130058E03, Pag1, 4930578N18Rik, 6430710C18Rik, Fam43a, Snora81, Cyp20a1, 4922502D21Rik, Lsm1, Gm10791, Kcnh2, 1700109K24Rik, No16, 4922502D21Rik, Trib2, Nrf1, Rgag4, 4930426L09Rik, Ppi13, Vmn2r96, Ngly1, 1810046K07Rik, Hid1, Olfr1510, Nrip1, Dhtkd1, Ms4a6b, 4930583K01Rik, Atp1b3, Mir7046, St8sia1, Pcdh7, Micalc1, D030024E09Rik, Pold4, Coro2b, Adamtsl4, Auh, Fus, Hclsl Prkcq, Nimlk, Zdhhc14, Kcnh2, Cd37, Ttc27, Olfm2, Ubac2, Mir6387, Zfp619, Zbtb9, Gpr125, Ppp2r5a, Adgb, Pard3, Ctr1, Ddr1, Ckmt2, Lpar6, Sspn, Gm4792, 9430008CO3Rik, Ngly1, Tbx19, Heatr1, Cdc14a, Nabp1, 8430436N08Rik, Cd247, Llph, Pex10, Eea1, Lef1, Ly75, Dock11, Haao, Rgs3, Mndl-ps, Maml1, Stxbp1, Parpl1, G530011006Rik, Mgrn1, Ift57, Mef2a, AI427809, Ldhb, Cdk19, Lrrc3b, Osm, Dnajcl5, Mirlet7i, Stk38, Cep170, Rcn3, Gramd1a, Mfng, Vgll4, 1700017N19Rik, Atp1a3, Ptpla, Mir6962, Jun, Cdk19, Gm10638, Zfp3612, S1c39a10, Tpd52, Mthfdl1, Agbl1, 4922502D21Rik, Ceacam2, Drosha, Fut8, Cox10, Dnajb12, Thns12, Eefsec, Pgpepl1, 4932441J04Rik, Fndc7, Clip1, 2700046G09Rik, Itpkb, Kremen1, Mpp6, Ccr9, Tbcb, Rictor, Gm3716, Icos1, Cpeb4, Mir7681, Kmt2c, Mak16, Gli1, Act19, Gpatch2, Sept14, Aebp2, Phlpp1, Zfp957, Ap3m2, Zcchc2, C030018K13Rik, Cdk17, Tmem217, Cog6, Dock2, Il7r, Crybb2, Slc16a10, Ppplr1b, E430016F16Rik, Fbxo17, Akrld1, D10Jhu81e, Irgc1, Klf7, Pcdh7, Nipb1, Rrn3, Mir7681, Arhgef33, Rhoq, Dusp5, Itga4, Palm2, Map10, Tigd2, Mfge8, Zfp580, Peli1, Trim59, F730035M05Rik, Gpr110, Lyst, Slc10a4, C230029M16, Gpnmb, Rgs3, Rab3ip, Vps54, Cox7a21, Slc7a15, Serbp1, Slc22a16, Prkch, 4933433H22Rik, Arap2, Mk11, Slc22a16, Fli1, Stk24, Stard8, Arhgap29, Pcca, Trem12, Tssc1, Pgpepl1, Syde2, A430107P09Rik, Foxo1, 8430436N08Rik, D030024E09Rik, Tcf7, Ifitm6, Ctso, Capzb, Lypd3, Lix1, Ccdc170, Tasp1, Dnah7a, Sugt1, Pde7a, Pcnp, K1f5, Olfr1357, Ldhal6b, Kctd12b, Cxxc5, Pkn2, Mboat2, Angpt1, N6amt2, Gm839, Bach1, I12ra, Ankrd12, Ccdc64, Pptc7, Ikzf2, Svi1, Tlr1, Rell1, Tma16, Mbnl1, Cyfip2, Rps6ka2, Elov16, Dap11, Zfand3, Unc5c1, Zfp619, Syt13, BC031361, Fam26e, Gm2799, Chst15, LOC101055769, Sepp1, a, Ccdc171, Hemgn, Pik3c3, Lrp12, Capnl1, Pvr, Prkcq, 4932702P03Rik, 2300002M23Rik, Tef, Foxp1, Lypd6b, 4933412E24Rik, Wnt4, Marco, Elfn2, Smim9, Dip2b, March2, Frs2, O1fr1507, Mir7219, Fbx122, Vim, 4933432G23Rik, L3mbt11, Madil1, Calr4, Lrrc3b, Strada, Mir363, Tspan9, Esrp1, Panx1, Tgfbr2, Emb, Spata3, Ext1, Ca1m2, AY512915, C530008M17Rik, Mitf, Wdr11, Mir5127, Selt, Gm6623, Gm684, Gm3716, Tgtp2, Sptb, Hamp2, Itgb6, Cd2ap, Pmp, Ift80, Slamf6, Pou2af1, Snx29, G530011O06Rik, Wipf2, Fam134b, 4930428G15Rik, Ig111, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, Tecta, Mir7687, Mir6367, Itga4, Tns4, Ccm2, Wipf1, Cerk, Znrf1, Elov15, Phtf2, 1300002E11Rik, 2210417A02Rik, Mir7061, Grhpr, Mark4, 4930564CO3Rik, Svop1, Pja2, Tfdp2, Rbm11, Usp6n1, Mir6368, A430107P09Rik, Bc12, Cdc42se2, 4933433H22Rik, Apo18, Xpnpep2, Dach2, Mir205, Stard5, Fsbp, Rph3a1, Vav3, Gm10125, Lpcat1, Cd2ap, Bank1, Smurf1, Aox2, C230029M16, Sgms1, Eci3, Xpnpep2, Pfkfb2, Utrn, Ldlrad3, Gabrr1, Kcna2, Ywhaz, Stard13, Atp1Oa, Slc39a10, Whsc111, Gm12522, Trio, Manlc1, Hmha1, Gm10791, Kidins220, Lad1, Mir1928, Gm13710, Mir1963, Lama4, Pard3, Susd3, Taok3, Skor2, Matn2, Tet2, Mir7674, Ccdc64b, Fam49b, 4933412E24Rik, Thsd1, Sa113, Papss2, Tcea13, Rreb1, Klrd1, Rgs3, Cst10, Itga4, Gm20098, Smarca4, Cyp2d22, Kdm6b, Cntn5, Dyrk2, Dusp10, Srpk2, Etv5, Slc25a25, Cfl2, Micu1, Ets1, Gm6559, Zfr, Mrp152, Cerk, D630010B17Rik, Ext1, Cb1b, Gnai2, Apo17e, Manba, Dusp10, Smim8, Mir6907, Pard3, Tmem35, Ric8b, Gm14124, Pik3r1, Gm11981, Dip2c, Plin2, Fam228a, Tlr1, Lypd6b, Zc3h12b, Abcg1, Ext1, Camk2g, Ptgr2, Mndl-ps, Rftn1, Sox8, Sdc3, Mab2113, Arid1b, Tdrp, 4921525009Rik, Arid4b, Micu2, Ly86, Afp, Grap2, Ist1, Sh2d4b, Rad52, Mir1668, Rpgripl1, Gramdla, Sgk1, Fos, Smad4, Hdac4, B3gnt3, Nr4a3, St8sia1, Psg-ps1, Act19, Pdk1, I12ra, Irf2, Fas1, Hsdl1, Galnt5, Itk, Mam12, Erdr1, Ndufa6, Tbc1d23, Slc43a2, Iqgap1, Klf7, Bend5, Klf4, Lif, Calr4, Cnst, Ifnk, G3bp2, Tbc1d2, C030034L19Rik, Zfhx3, Bc111a, Retn1b, Ap3m1, Hlcs, Serpinf1, Gm16390, Wdr37, St8sia1, Cenpu, Gm10638, Tfpi, Fabp7, Wisp3, Psma1, Tet2, AI854703, Lmo4, Ppplr1b, Mgat5, Foxp1, Gm3716, Mir6349, Tle4, Itgb8, Rab11lfip4, Tbce1, Npepps, 1300002E11Rik, Celf2, 4933412E24Rik, 4930415F15Rik, Olfr1507, Itgb3, Bace1, 2010015L04Rik, Mir7656, Esrp1, Spred2, Myo10, A930001A20Rik, BC048403, Lincpint, Mtum, Shisa2, Mef2d, Rac2, Dusp6, Lef1, Tmem64, Lrig1, Atp6v1g1, 1700017N19Rik, Dfna5, Zfp286, Gimap9, Gbe1, Cdc37, Pard6g, Serp2, Pid1, 4930465M20Rik, P2rx4, Opalin, Mir684-1, Ngly1, Ndufa4, Mir16-2, Trib2, Slc17a9, Itpripl1, Uri1, Rnf32, Pr1r, Lyrm7, Fbln1, Nenf, At12, Slfn1, Supt20, Ski, Pno1, Foxo1, Olig3, 5330411J11Rik, Eci3, Clic4, Naa30, Abca1, Mpp1, Adcy6, Ptprc, Fbxo27, Ahcyl2, 1700016K19Rik, Gm14405, Drosha, Lrrc1, Mir7014, Cdk19, Ldlrap1, Pgpepl1, Fg12, Nck2, $Am^{-2}a$, Myo10, Cb1b, Gm590, Kcnq5, Col6a1, 4930480M12Rik, Rad23b, Tram2, Pygo1, Mir6368, A430107P09Rik, Afap1, Pip4k2a, Slc46a2, Mgat5, Slc27a6, Ntper, Cuedc1, Ramp1, Enthd1, Mir6374, Stmnl-rs1, Gm684, Fbin1, Lef1, Chd7, Ppplr3fos, Abi1, Plau, Aifl1, Tesc, Edem3, Tbce1, Prdm5, Lnpep, Dyrk2, Gm6260, 4930428G15Rik, Carns1, 8430436N08Rik, Plekha5, Hexim2, Ccr7, Foxp1, Satb1, Rpgrip1, Dnm3os, Retn1b, Tram1, Tmppe, Car12, Snordl4c, Ets1, Crtc3, Kcnh8, Hey1, Slc44a2, Dip2c, Ankrd44, C230029M16, Nwd1, Mrpsl1, Cpb1, 4930567H12Rik, Mir378c, Dnaja2, Fnbpl1, Tab3, Zap70, Cenpk, Bcar3, Usp6n1, Ppp4r2, Has1, Tbc1d22a, Dync21i1, BC055111, Sepw1, Ap1s3, Ass1, Metrn1, Rsph3a, Dpys12, Rapgef6, Cxcr4, Mir8095, Sgsm3, Actn1, Grb10, Slpr1, Rasgrp1, Dnajc6, Agfg1, Map3k15, 4930465M20Rik, Csnk1g3, Trpv5, Klf3, Zfp3612, Mir181a-1, S1c30a9, Taf3, Em12, Tssc1, 1190002N15Rik, Cdh26, Sav1, Ghsr, Msra, Fam134b, Tusc3, Itpkb, Dtwd2, Frmd7, Gm20750, 4933440M02Rik, St8sia1, Mir8105, Mir7681, Sntg1, Hipk2, Cd8b1, Stk24, Zmat4, Pnoc, Creb1, Trps1, Gls, Gm15706, Ubtd2, Kif1b, Pex3, Ect21, 4732490B19Rik, Ca1m2, Syne1, Aplb1, Ldha, Mmp15, Tnks, Gm20098, Spred2, Igf2bp3, Atp1a3, Pdzrn3, Qser1, Ppml1, D930032P07Rik, Vmn2r98, G530011006Rik, Ikzf1, D630010B17Rik, Mett18, Gm590, Enthd1, Ccdc152, Ywhaq, Atp8a2, Thra, Ildr1, Rpap3, Ltb, Rev31, Med131, Dner, Ralgps2, 4930428G15Rik, Dnajc1, Arhgap6, Fam101b, Nfam1, Ccr7, Psma6, Gm1631, Hadh, 3425401B19Rik, Irf4, Zak, Brdt, Fam71f2, Slc25a12, Ippk, Fnbpl1, Rps16, 4930540M03Rik, Cd5, Ube2e1, A430107P09Rik, Rapgef4, Olfr1507, Rmdn2, Lhfp, Mir1893, Lga1s3, Gn131, Whsc111, Sh2d1a, BC061194, Mbn12, Zbtb38, Go1ph3, 4930430F21Rik, H2-Q1, Ntrk3, Ninj2, Cd3e, Stat5b, Lbx1, 4933412E24Rik, Pten, Gm2447, Mtx2, Tmcc3, Lin28a, CybSa, Znrf1, Fancc, 1500015O10Rik, Plekho1, Prss32, Gjd2, Gphb5, Ccr7, 4931403G20Rik, Mboat1, Dyrk2, I19r, Sos1, Etv2, Txnip, Fam110b, Rph3a1, Mboat4, Plekhh2, Irf6, Thoc7, Yeats4, A430107P09Rik, Ms4a7, 4930567H12Rik, Zfp930, Zap70, Uaca, Nsg2, Myo10, Ctf1, AU015836, Mir7681, 9830132P13Rik, 1700021F07Rik, Ipo4, Icos1, Smad5, Cyp26b1, Mgarp, A430078G23Rik, Kdm6a, I730028E13Rik, Hs2st1, Tox, Akrld1, 1810010D01Rik, Rp134, Ramp1, Hcls1, Rab3ip, 4930445N18Rik, Ext13, Sox4, Gjd3, Gm14305, 1700061F12Rik, Lnpep, Wnt5b, Mark4, Stmnd1, Olfr1507, A430107P09Rik, Commd8, AI427809, Mir6979, Cdc42se2, Gpr125, Tcf25, Taf8, Lclat1, Wdr89, Ptk2b, Pitpnb, Ttf2, St6gal1, Mam12, Lrch3, 5430427M07Rik, Bach1, Exoc4, Mef2d, Vps37b, Wdr37, Ccr7, Fam221a, Mif, Vmn1r157, Mpp6, Chd2, Sept6, She, Prg4, Snord83b, Gm7616, 2410114N07Rik, Wdr37, Gdpd4, Vdac1, Mir5104, Rsrc1, 4930523C07Rik, Akap2, Lyst, G6pc2, K1h14, Slc35b4, Setbp1, Akap2, 1700072005Rik, Gm1604b, Kcnal0, Stambpl1, Npas2, Dnajc1, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrod1, Tm2d1, 4930572013Rik, A130077B15Rik, Lck, Kdm2a, Rbbp8, Cd47, Gm6578, Klf2, Zfp536, Ube2e3, Aff3, Manla, 4930413G21Rik, Crtam, Rpa1, Kcnh3, 2900008C10Rik, Tbcld31, Snn, Malat1, Bambi-ps1, Wisp3, Mrgprb5, Gch1, Nabp1, Mett19, Zfp3612, Mir7669, 4933401H06Rik, Prkrir, Erdr1, Olfr630, Tmem168, Gbpl1, Mbnl1, Plin2, Scn2b, Car8, Ngly1, Kcna2, Dpp6, BCO27231, Gosr1, 1700016L21Rik, Ccdc170, Manba, Osbp19, Purb, Rftn2, Klf3, Cdca71, Supt71, Rgs3, Rbpms, Mir6349, 5830418P13Rik, Pkn2, Basp1, Btg2, Ifnk, 5730403I07Rik, Srsf1, Kif3a, Fbxo27, Gipr, Colq, 4930540M03Rik, Pard6g, Bclla, Ezh1, Cd2, Foxq1, Rybp, Pgap1, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhc18, Mroh2b, Gpr3, Tgfbr2, Reck, Atxn713b, Ngly1, Il12rb1, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4i1, Slc7a1, C9, Mir6374, Mdm1, 2310043L19Rik, Fbx117, Gm5468, Panx1, Sct, Racgap1, Ppm1b, Samd12, E330009J07Rik, Cd101, Zcchc2, Gad11, Rapgef6, Steap3, Fgfr1op, Setd7, 3110056K07Rik, Gm5538, Ino80e, St6gal1, Nsmce1, Ccdc64, Cxcr4, Gata3, Cerk, Chst15, Mir3089, Map4k4, Akap13, S1c30a9, Gm10790, Npffr1, Tdrp, Gm20098, Ddhd2, St8sia6, Lhx2, Syt6, Dt1, Themis, Mam12, Sh3bgr12, Sptbn1, Fam207a, Lmna, Nfatc2, Gm12185, Arhgap6, Atg14, Macrod2, Mir3110, Fam46c, Wdr63, Ppp2r1b, Prdm9, Lphn2, Mir574, 119, Elov16, Chd7, Pitpna, Atoh7, Mc2r, Celf2, Tdrd3, Rassf2, Gm10640, Ncoa3, Lyst, Fyb, Gm2447, Aplar, Stag2, Foxp1, Rock2, Pdlim1, Bin1, Gm10125, Bach2, Fbx122, 2900005J15Rik, Rgs2, Cldn10, Lrrc8d, Rad23b, Supt20, Dgkd, Atn1, Agtrla, Pias2, Gm10791, Tmem60, Prkag2, P4ha2, Trat1, March5, Tcf7, Wbscr27, Gm6498, Hist1h2bn, Zfp120, Trub1, Mir1936, Ms4a7, Nfatc4, Lrm3, Trat1, Sox4, Nhsl1, Lincenc1, Tmem243, St6gal1, Dpys12, Cntln, I17r, Olfr9, Erbb2ip, Rp1101, Mir211, Srbd1, Lphn2, Fam3c, Sorcs2, Thrb, Katnal1, Mir199a-1, Fbxo32, Rpap3, Arfip1, Rp119, Itm2a, Trim56, Ier51, Btg1, Plekhb1, Rp134, Pik3r1, Mir6349, Ikbkb, Cntn5, Sh3kbp1, Btg1, Cd101, 4930523C07Rik, Qsox2, Serh1, Rfc1, Cga, Bmyc, Sla, Rev31, Fam134b, Ggact, Mir466o, 28-Feb, Akrld1, Tnfsfl1, 2310040G24Rik, Gcic, Pde4b, Dgkz, Hsbp1, Eif3k, Gipc3, Mthfdl1, P2ry1, Ets1, Cxcr4, Pja1, Trem12, Ccr7, C230024C17Rik, Rps6ka5, K1f4, Cx3cr1, Echdc3, Hspa8, Lama4, Mg11, Ophn1, Thnsl1, Disci, Pdzrn3, Sms, Zfp704, Zfp3612, Fam105a, Mad211, Dazap2, Fbx114, Vapb, Ifnab, Zgrf1, Rtkn2, Ppp2r3c, Vmn2r96, Bbs9, Ifn1r1, 1700064J06Rik, Ppp1r37, Tgfbr2, S1c2a2, Lef1, Ccr7, Foxq1, Gan, D6Ertd527e, Snx9, Hes7, Fbxo47, Cox10, Bend3, Sgms1, S1c30a9, Gm3716, Foxo1, Rsbnl1, Tmc1, Fam120a, Gpr18, Efhc1, Ramp3, She, Akap7, Vezf1, Dnajc3, Tnpo1, Nudt1611, Gm19589, Ankrd60, Txk, Lix1, Dnajc6, Serinc5, Lef1, Tars, Gm3336, Bace1, Nedd41, Trib2, Gm6994, Bc111a, Mir5127, Klrb1b, Nfix, Tigd2, Map4k2, Uxs1, Bach2, 4930583K01Rik, Klhdc9, Eepd1, Als2c1, Pard3, Wdr27, Ikzf1, Btg1, Ly6e, Prm1, Taco1, Itpr2, Limk2, Bend4, Gtf3c3, Kcnh8, Cd96, Fam229b, Adamts14, Lyrm7, Fhit, Sqrd1, Fpr-rs4, Tmem260, Cd55, Mir214, Mir3093, Amigo2, Dapp1, C030018K13Rik, A230028005Rik, Shf, Lef1, Nrp1, Efr3a, Tmem30b, Mynn, Tgfbr2, Nfia, Ipcef1, At12, Thpo, Fam49a, Mir6387, Rtkn2, Gucy1a3, Chrna9, Rassf2, Clip4, Wnt10a, Opalin, Llph, Mir6995, Sorcs2, S1c2a2, Gm20110, Syne1, 2810001G20Rik, 5430434115Rik, Ppp1r37, Itgb6, Hspa8, I19r, Glrp1, 5430421F17Rik, Tstd2, Zswim2, Ext1, Slc16a10, Zfp957, Slfn5, Lrch1, Scin, Cardl1, Ext1, Tet1, Scm14, Diap2, 4933433H22Rik, Zfp629, Tspan13, Prkcq, Zcchc13, Cd74, E330017L17Rik, Tm2d1, Gpr126, Nm1, Fam124b, Tubb2a, Tdrp, Tnfrsfla, Foxp1, Fam107b, Epb4.115, Fam78a, Rasa12, Mapk9, Creb312, 4930539M17Rik, Kcmf1, Ctage5, Ankrd12, Manba, Tmc1, Lmanl1, Nacad, Agr3, 4933433H22Rik, Matk, H2bfm, Kcnh2, Pgr151, Inpp4b, Kcmf1, 4933430N04Rik, Vmn2r92, Stk17b, Foxp1, Cep5711, Lix1, Kcnal0, Vang12, Treh, Enthd1, Gm6559, Brf2, 4921525009Rik, Prkcq, Igsf3, Fut8, Limk2, 5730508B09Rik, Clasp2, Twsg1, Tmem126b, Hoxa7, Cd28, Sh3bp5, Furin, 1700001P01Rik, Diap2, Tecta, Icos1, F11r, Mir7023, Fes, Map3k5, Spry4, Cd44, Ralgps1, Gm16793, Alox5ap, Mir5098, Arid1b, Ugcg, Ctla4, Snx9, Mir8095, Is12, Osbp16, Dyrk1a, Cd300a, A930011G23Rik, Fam26e, Ikzf2, Enpp6, Mir181a-1, Lyst, Grh12, Aldhla7, Hmgbl-rs17, 2410004B18Rik, Dnm2, Nabp1, Foxp1, Tnfrsfl0b, Prkcq, Sgsm3, Agr3, 1700017N19Rik, T1e3, 4933406K04Rik, Insr, Whrn, Ets1, Lef1, Mir5618, Soat1, Ccr7, Cmss1, Ahcyl2, Mgat1, Hspa13, Znrf2, Kcnh8, Tdrp, Gm1604b, Vmn2r95, Akap6, Tbc1d22a, Lbp, Mk11, Rsu1, Sstr2, S1c37a3, Ube2d2a, Itpka, Rnf220, Hnrnph2, Gm2933, Akap2, Pdzklip1, Wwp1, Vapb, Dyrk1a, Dynit1b, Zfp365, Ssh2, R3hdm1, Nek10, Zswim2, Ccdc90b, Znrf1, Ms4a5, 4933406K04Rik, Actr2, Rgmb, Ston2, Gnas, Stkl7b, Pim1, Mtr, K1h12, Cdk15, H2-Ob, I123r, Slain2, Tssc1, Sbk1, Ube4a, H2-T3, Gtf2ird1, Tyw5, Hbsl1, Efhc1, Rpe, March6, Itga4, Fam13a, Lst1, Ankrd55, Nif311, Fam69b, Mir7674, 2810001G20Rik, Gpr19, 4930567H12Rik, Foxp1, Dgkz, Cenpf, Amigo2, Panx1, B4ga1t3, Pag1, Ub13, 1110059E24Rik, Hs1bp3, Slc6a19os, Mdm1, Limd2, S1c6a19, Bank1, A1g13, Wisp3, Suit5a1, Fam86, Dennd2d, Cacnb2, Tesc, Mdm1, Adipoq, 1810026B05Rik, Mir325, 1700096J18Rik, D030024E09Rik, G0s2, Mir7219, Slpr1, Cxcr1, Ext1, Chd1, Ly86, Dhx40, 4930564D02Rik, Dctn6, I17r, E230025N22Rik, Sgk3, Bach2, Ramp1, Syt6, Gsap, Ccdc152, Jakmip1, Atp8a1, Grap2, Dynitlf, 4921513I03Rik, Gpc6, Kcnal0, Ipcef1, Mir7061, Btg1, Stoml1, Zfand3, Aqp4, Zfp281, Ccr2, Nrip3, C230029M16, Tcf4, Hadh, Mthfdl1, Lhfp, Gpr114, Plbd1, 1110034G24Rik, Cd79a, Gse1, Churc1, Map3k7c1, Filipl1, Galnt7, App12, March5, Zswim6, Skap1, Tgfbr3, S1c16a2, Pal1d, Atg10, Cap2, Dfna5, T1r7, S1c24a1, Hivep2, Dock4, Cd300a, Igf2bp2, A430107P09Rik, Lrrn3, March2, Gm21057, Apbblip, Piga, Zbp1, A430107P09Rik, Trappc8, Zdhhc14, Stkl7b, Sh3pxd2a, Ppifos, Chd1, Socs1, Kdr, Gramd3, Urad, Sipa111, Gm20098, P2ry2, Gas8, Sox5os3, Ccdc117, A130077B15Rik, Basp1, Zfp365, Syde2, Laptm4b, Sik1, 4933433H22Rik, Npff, Amt1, A1b, Zmyndl1, Gm20098, 119, Hadh, Sstr2, Emp1, Lef1, Galnt10, 5430434I15Rik, Cmah, 4631405J19Rik, Hesx1, Gm16793, Rp1p0, Sa113, Xdh, St8sia1, Folr4, Sp3, Rassf3, Aox2, Emp1, Rragc, Proser2, Gm8817, D030028A08Rik, Btg1, Mad211, Upb1, 1810006J02Rik, 4932702P03Rik, Rhoh, Gm10790, Dock10, Fam166b, Pcdh1, Zbtb24, Camklg, 4933407L21Rik, Pde7a, A430093F15Rik, Pmepa1, Ropnl1, Grap2, Rims3, Rps6ka1, Eps15, 4930445N18Rik, 6430710C18Rik, Ppplrl3b, 1121r, Mtmr2, Prex2, Atp6v0d2, Ablim1, Hnmpd, Syde1, Slc16a1, Mbnl1, Sgms1, H2-DMb1, Ly6a, Tlr1, Gm20098, Galnt5, Edem1, Fam173b, Gpr126, Nbeal1, Pr1r, Tmc1, Csmp1, Atp1Oa, Dusp4, Lpar6, Pitpnb, Actr2, Ago2, Lphn2, Gm2447, Myo18a, Cd101, Cngb1, 1700027J07Rik, Vmn2r91, Folr4, Satb1, Man2a2, Smim14, 3300005D01Rik, D130058E03, Angpt12, Ercc3, Tmem87a, Syne1, Ptrf, Gm2447, Zscan2, Bend4, Endod1, Tgfb3, Mir6962, Rragd, 4931403G20Rik, Ddr1, Map4k3, Fabp4, Stk17b, Gm5122, Rapgef4, Neurl1b, Pdgfrb, Cirh1a, Fnip1, E030002003Rik, Fam65b, H2-DMa, Btg1, Zc3h12b, Prkch, Sipa111, Tdrp, Adtrp, Fam129c, Runx3, Hvb1, Tbx19, Filipl1, A430107P09Rik, Ccdcl1, Lphn2, Spgl1, Mir6395, Foxp1, Dtnb, Mrp113, Egln3, Fpr1, Rapgef4, A130077B15Rik, Th7, Rbpms, Gm1966, Tmem150b, Rev31, Mad211, Gm1604b, Tasp1, Slc19a3, Trappc10, Ralgps2, Npas1, Ptprs, Slc36a1os, Maf, Wdr12, Polr3k, Gm20750, D14Ertd670e, Fam46c, Fam46c, Ptger1, Lclat1, Ptma, Actn2, Tspanl1, Zfp879, Spred2, Satb1, Nabp1, 4930486L24Rik, Ugcg, Txk, A430107P09Rik, Hadh, Abtb2, Rbm33, Fli1, Fyn, Mgat4a, Snd1, Glt8d2, H2bfm, 9130401M01Rik, Snd1, Mir3079, Pcdh7, Cnga1, Tldc1, Ugdh, Aven, Mir8104, Rgl1, Sox6, Map3k14, Akirin2, Mir684-2, Rfx2, Fyb, Ccdc711, Ece1, Gm8884, 4921507P07Rik, Mir6933, Slc6a7, Cox7b2, Rfx4, Gm5617, Sh3kbp1, Pds5a, 9030617003Rik, Gpr126, Ctnnbl1, Prpf40a, Gpr22, Cldn10, Cdk19, Sgk3, Rgs3, Mir6995, Cdon, Stk17b, Samhd1, Gm16793, Lag3, Olfm2, Cyb5a, Zfp438, Akap2, Dpf1, 3110052M02Rik, Lrp6, Haao, Camk2a, Tspan9, 5430434115Rik, Stk24, T1r12, A930005H10Rik, Slc4a4, U2af1, Fbx121, Opalin, Rybp, Igsf3, Aim1, Wasf2, Rgs3, Frs2, Smok4a, Pak4, Zscan22, A430107P09Rik, Slc35b3, Serpinb5, Med30, Cdc16, Agfg1, Tmem261, Plxna1, Myo5c, Gpr183, Suclg1, Cdk19, 4930556N09Rik, Lpp, Tmem260, Ubqln2, Mir378b, Btla, Gm19589, Ano6, Clint1, Ube4b, O1fr1507, Rab33a, 4930523C07Rik, St6gal1, 1600014K23Rik, Nnmt, Ift80, Htr3b, Rp134, Ipcef1, Psma6, Dnmt3a, Hpgds, Stxbp3a, Mir6907, 1700056E22Rik, Smad7, Mir7078, Mir181b-2, I127ra, Stat1, C030018K13Rik, Foxq1, Hpcal1, Msra, Zc3hav1, Tdrd6, Tnfrsf4, 4921517D22Rik, Rubie, Plekhg6, Brd4, Sort1, U90926, 4930519F09Rik, I14ra, Smyd2, Prkch, March9, Ghsr, Rps6ka2, Rpp21, Vps13c, 1600002D24Rik, Fam136a, 4921511117Rik, Spef1, Mam13, St8sia1, Ssbp2, Stk4, Tnfrsf19, Snord104, O1fr1507, Dysf, Cntn5, Cd2, Raver2, Gm10790, Pja1, Tmprss9, Klf5, Ubash3b, Tle3, Scm14, Snx4, Tert, Sptbn1, Mir326, Aff1, Gm8298, Ephb2, Tec, F3, Exoc6, Sema4f, Denndla, Gmcl1, Gm10532, St3ga11, Chd7, Gm6268, Tox, Pja2, K1h13, Dnajc10, Foxp1, Trp53inp1, Gtf3c3, Scd2, At12, Dach2, Lynx', Cand1, Cxcr4, Gm20098, Fscn3, I19r, Dph5, Sh3bp5, St6ga11, Fli1, Mir5127, Ubac1, Gm16793, Nsmaf, Sp6, Rnf145, Ccr7, Orai1, Serbp1, St6galnac5, Tox, Cacna1b, A430035B10Rik, Alp1, H2-DMb2, Etnk1, O1fr1507, Mtr, Rgmb, Pmp22, Dctn6, Fli1, Mir326, Slc17a7, Sepp1, Slc6a19, Cngb1, Mir7681, Ccr9, K1h14, Atp6v1g3, Clecl6a, Speer2, Gsn, Umps, Unc5c1, Aox2, Dcaf8, Igf2bp3, Car2, Rnf43, Kdm7a, Tgfbr3, Eldr, BC094916, Unc80, Zmyndl1, Nabp1, Adamts14, Gm20139, Fgfr1, Tmem141, C130026L21Rik, D630039A03Rik, Mtum, Herc3, Gm5468, Mir6398, Fam86, Nsg2, Cb1b, Erbb4, Mir?-2, Smurf1, Clecl6a, Lhx2, Tomm20, Ifngr2, Acacb, Gm10791, Bach1, Epb4.112, Tmem154, Tssc1, Vdac1, Itgae, Raph1, Klf3, Pnrc1, Sell, Tdrp, Ptk2, A630072M18Rik, Slc41a3, Rab11b, Tnfrsf10b, Lrp12, Ptger3, Aggf1, 1700029F12Rik, Dpf1, Gm14295, Ubqln2, Coq2, Txndc8, P2ry1, 4933430H16Rik, Tctexld1, Sfmbt2, Alg14, Tha1, Ets1, Cd101, Neu3, Mob3b, Kcna2, Irs2, Mbnl1, Fntb, Nipb1, Slc16a5, Ccdc174, Ncs1, BC037032, Fry1, Lipa, Hslbp3, Cd101, Chd1, Atad1, Ppplr3fos, Pde4b, Lamtor3, Klf2, Ttc27, Dntt, 5830454E08Rik, Panx1, Cyp2r1, Rhou, Mir701, Ccr7, Arhgap26, Ankrd36, Retn1b, Themis, Med131, Slc6a19os, Znrf2, Mett18, Mir3108, D030025E07Rik, Mir145b, Iqsec1, Cd8b1, Clic1, 1810026B05Rik, Ptprs, Med7, Mthfdl1, Dnali1, Bach1, Mgmt, Ppm1b, 4933430H16Rik, Cd401g, Txk, Cdcl4a, Il9r, Slc7a15, Prkch, Srpk2, Tmbim7, Rcor1, Vti1a, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511117Rik, Dlx1, Lhx2, and/or Chst15. In some embodiments, the transcriptional target is Irf8, Ctps, Chst15, Sipal11, 2610005L07Rik, Irf8, Etv5, Ctps, Grk5, Cd200r2, Cenpu, Atp2b2, Srfbp1, Fndc9, Tlr6, 3300005D01Rik, Vav3, Dusp5, Sipal11, Chst15, 2610005L07Rik, Cxxc5, Mrc2, Plod3, Bmpr2, Cd55, Ear2, Tmtc4, St6galnac3, Cenpa, Filip1, 6330407A03Rik, Gm10389, D8Ertd82e, Gm156, Mcf21, Enpp6, 2610005L07Rik, Cdyl2, 3300005D01Rik, Gm10389, Irf8, Mir3081, Grk5, Enpp6, Srfbp1, 3300005D01Rik, Vav3, Chst15, Sipal11, Filip1, 2610005L07Rik, Bmpr2, 4930415F15Rik, St6galnac3, Ralgapa2, Tmtc4, Abhd6, Gm10389, Zfp3611, Ctps, Atp2b2, Fndc9, Tlr6, 3300005D01Rik, Dusp5, Cxxc5, Irf8, Plod3, Bmpr2, Cd55, Ear2, St6galnac3, Cenpa, Grk5, Filip1, 6330407A03Rik, Srfbp1, Filip1, Snai1, Il7r, 111r2, Ly6i, Gm5, Snai1, Snai1, Klrg1, Tff1, Zfp3611, Pmepa1, Urb2, Snai1, Klrg1, Fchsd2, Il7r, Zfp3611, and Klrg1. In some embodiments, the cell is a T cell. In some embodiments, the cell is a CD8+ T cell. In some embodiments, the cell is an exhausted T cell.

Engineered T Cell

In some embodiments, the invention provides a cell (e.g., T cell) engineered to have an altered epigenome that contributes to increased immunological response in a patient having a disease such as cancer or an infectious disease. In some embodiments, the engineered T cell of the present disclosure comprises an alteration in a high priority epigenetic pathway. In some embodiments, the T cell is an exhausted T cell ($T_{EX}$). In some embodiments, the high priority epigenetic pathway is targeted. In some embodiments, the alterations in the high priority epigenetic pathway comprise genetic modifications introduced via genome engineering approaches or epigenetic modifications using inhibitors or activators of epigenetic regulators. In some embodiments, the high priority epigenetic pathway has been targeted by genome engineering, e.g. by knocking out/in transcription factors or other genes in the epigenetic pathway, or by modifying the function of protein encoding genes in epigenetic pathways. In some embodiments, the high priority epigenetic pathway is targeted by knocking out regulatory sequences in the OCR domains associated with T cell exhaustion. In some embodiments, the targeting of the high priority epigenetic pathway prevents or reverses exhaustion of the T cell. In further embodiments, the targeting of the high priority epigenetic pathway prevents or reverses exhaustion of the T cell. Targeting of the epigenetic pathway can result in a change/changes in at least one of Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. In some embodiments, the epigenetic pathway is targeted with a drug or with genome engineering via CRISPR/Cas9 targeting.

In some embodiments, an engineered mammalian T cell of the disclosure comprises a high priority epigenetic pathway, wherein the high priority epigenetic pathway is targeted, the high priority epigenetic pathway comprises an epigenetic change in or altered expression of at least one target (e.g. epigenetic target and/or transcriptional target), and the targeting of the high priority epigenetic pathway prevents or reverses exhaustion of the T cell. In further embodiments, the targeting of the high priority epigenetic pathway prevents or reverses exhaustion of the T cell. In some embodiments, the epigenetic change comprises a change in at least one of: DNA accessibility, histone methylation, acetylation, phosphorylation, ubiquitylation, sumoylation, ribosylation, citrullination, and DNA methylation. DNA accessibility at key loci is known through this disclosure to be important in changing the biology of exhausted T cells. This effect may be mediated by changes in histone methylation, acetylation, phosphorylation, ubiquitylation, sumoylation, ribosylation, citrullination, and DNA methylation.

Epigenomic Signature

Exhausted T cells have a unique epigenome as compared to naïve, effector, and/or memory T cells. This unique epigenome is referred to herein as an "epigenomic signature." The epigenomic signature comprises a signature of genes uniquely expressed in $T_{EX}$.

An approach that could not only identify and enumerate, but also interrogate changes in activation state and relation to disease status could be of considerable value in monitoring patients on immunotherapies and be used to guide choices of immunotherapeutic approaches and help track immunological treatment response.

A signature of genes uniquely expressed in $T_{EX}$ is identified herein. In some embodiments, the signature of genes uniquely expressed in $T_{EX}$ comprises SERTADI, XPA, HINT3, HIST1H1C, ZFP69, NR4A3, TNFAIP3, SAP30L, SPRY2, RYBP, TIPARP, YAf2, GCHI, GTF2B, PCGFS, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, TOX, HSPA1A, SP140, SPAG7, MYCBP, TRAPPC2, TCF4, RBL2, ALS2, IKZF3, IRF7, ELL2, MXD1, IRAK2, MXI1, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and/or SAP30. In some embodiments, the signature of genes uniquely expressed in $T_{EX}$ comprises A330093E20Rik, Rnf19a, 2010010A06Rik, Cdh23, Abtb2, Dync2li1, Lrrc1, Scn1b, Manla, Gimap3, Lef1, Co126a1, Gpr180, Fam126a, Wdyhv1, Mir6395, Gpr34, Fcgr1, Rpia, A430107P09Rik, Hbsl1, Slc35b3, Tmem248, Cox7a21, BB019430, Pde5a, Sept7, Lrrc3b, Cd101, Znrf3, Znrf1, Gm6260, Prpf40a, Ets1, Scn3a, Kremen1, Fam210a, Trpm1, Pip4k2a, Trnp1, Sell, Nfia, Lipa, Zc3hc1, Msgn1, Yeats4, Abcd2, Tbcld1, Kcnh8, Zfp407, Capg, Gm7538, Rgcc, Sh3bp5, Slpr1, Zfp957, Mcur1, D16Ertd472e, Trat1, Fam107b, Mbtps1, Egr3, Palm3, 9030624G23Rik, Ppp6r1, Ckap4, Rngtt, Crtc3, Peak1, Lhx2, Btg1, Serbp1, Cd2, Acox1, Hormad2, Gm10684, Smo, A630075F10Rik, Ndst1, E030018B13Rik, Skpla, Kcnh8, Nck2, Frmd7, Cldn10, Peli1, 2010300CO2Rik, Ins15, Supt20, Slc4a4, Rph3a1, Dip2c, Pm20d2, Nsg2, Rbm26, Tpk1, Stambpl1, AF357399, Car2, Mir145b, Zfp592, Galnt4, Gm5083, Thnsl1, Dhx40, Gm20098, Ly6i, Sugt1, Ywhaz, Rad23b, Bcor, Gm12159, Vegfa, Cacna1b, Arhgef11, 2210408F21Rik, Mett18, Wdr73, Usp12, Art4, Clvs1, Mir6388, Diap2, Gm10532, Msi2, 4930546C10Rik, Mbnl1, Tm6sf1, Ppp2r5a, Mageb16-ps1, Neurl1b, Sspn, Suv420h1, 2410088K16Rik, Rg12, Timm8a2, Aebp2, Mam12, Ldhal6b, Peak1, Parp2, Apbb2, Tctexld1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efcc1, Malat1, 4931403G20Rik, Tox, Arpc3, Atg10, Gpbp1, Gm5148, AI317395, Abhd2, Celsr1, Tsen2, Pfkfb3, Cyc1, Mir378c, Slamf6, Btg1, Phf2, Cxcr4, Gm10789, At12, 6030407003Rik, Ggnbp1, Angpt1, 9530077C05Rik, Basp1, Rapgef6, H2-Ea-ps, Fam214a, Ppfia4, Lta4h, Ets2, Slc29a1, Xpo4, Gramd3, Itfg3, Fli1, Frmd6, Rbp1, Olfm13, Peli1, Srpk1, Hmgcs1, Irf2bp2, Cxxc5, Ccdc171, Cntnap2, Fance, Cb11b, Cubn, Sfmbt2, Srsf3, Pepd, Dgkd, Osbp16, Trib2, Zfand3, Dchs1, 5430421F17Rik, Fpr3, Dap11, Trat1, 0610040J01Rik, Gm14005, BC051019, Tank, Tnfsf11, Rara, Pik3c2a, Elmo1, Nck2, Bc12111, Fam78a, Gm10638, Prkcq, Gpr126, Bach2, Ttc30b, Nlk, Ube2e2, Usp3, 4932441J04Rik, Larp4b, Serbp1, Dbn1, Vav3, Dern, H2-T23, C130021I20Rik, Fbx114, Ets1, Fgf8, Ab12, Acvr1b, Upk1b, Efcab10, Uch13, Cd302, Cdc40, Nsg2, Tmem222, P2ry10, Klrb1b, Mc1r, Car8, BC048403, Taf8, Atplb1, Mir30c-2, Luc712, Erbb4, Arhgdib, Ube2h, Itpr2, Vav3, Ptgfrn, D630010B17Rik, Eif2s3x, Vav3, Nfe213, Ccdc171, Fignl1, 4930519F09Rik, 1700123O012Rik, Acsf2, Ndufb9, Atp7a, Upp2, Ptp1a, Man1a, Rgs3, Zbtb2, Trib2, Npr1, Fez2, Tle4, Fuca1, Cmip, Bcap29, Syne1, Dmbt1, Ell, Blnk, Sepw1, Gltscr1, Erdr1, Med131, Moxd1, Btg1, Akap6, 1810053B23Rik, Rsu1, Gprasp2, Art4, Gpd2, Tmlhe, A430107P09Rik, Kcnj9, Atp8a1, Adam6b, 2010109I03Rik, Spred2, Raver2, Ap1m2, Dclre1a, Rbp7, Gcc1, Traf4, Satb1, Gm5538, I112a, Fam60a, Thrb, Elk3, Vps45, Tle4, Akap13, Gprin3, Sox21, Emp1, Wfdc2, Slc45a1, Lnpep, Rapgef6, Txn2, Frmd4b, Myoz3, Zfp870, Bc16, Mvb12b, Ntrk3, Spaca1, Mir701, Cdca7, Gm5083, Slpr1, Spry4, Cck, Il6st, Hebp2, Slc43a2, Tdrd5, Gm5833, Mir?-2, Mir1931, Pdgfb, 1700052N19Rik, Nfkbiz, Gm20753, Hapin1, Rras2, Diap2, Manba, Cers6, Rasgrp1, Lnpep, Ap1n, Ephb2, Arpp21, Mica13, Chic2, E130114P18Rik, Ipcef1, Dyrk2, Bach2, Mir122a, B230206H07Rik, Ceacam9, A730006G06Rik, 4930542C21Rik, A430107P09Rik, Trat1, Ccr2, H2-Ob, Adm, Yeats4, Ccne1, Gpc5, Spsb1, Jrk1, Orc4, Camkmt, Nf1a, Celf2, Gadd45a, Gtf2a1, Nrde2, Nipa2, Rmi2, Lcor, Btg1, Atg10, D6Ertd527e, Ccm2, Dpys12, Dirc2, Cpm, Arhgap15, A730043L09Rik, Raph1, Cst10, Slc7a13, Ramp1, Atplb1, Zfp120, Slc39a13, Zfp706, Agr2, Tagap, Mir3110, Ubash3b, Dnmt3aos, H2-B1, Agb11, Smc6, 1700060C20Rik, Trib2, A930005H10Rik, Btg1, Scm14, Mir196b, Efna5, Tmem14a, Kcnj15, Snrpd3, Nnmt, Ryr1, Ptk2, P2rx4, 5830428M24Rik, Commd3, Cd28, Hspb11, BCO21785, Tcf7, Cstb, Art4, Tet3, Map3k13, Camkv, Ralbp1, 9330175M20Rik, Tgtp1, Selt, Irgc1, Tcf7, Tet1, Bnip31, Nrbf2, Nimlk, Rfx8, Th6, Grik1, Tox, 1700061G19Rik, Dhrs3, 4930519G04Rik, Mid1, Aplar, Basp1, Aqp4, 4930415F15Rik, Aif1, Rnf125, Fam134b, Atp13a3, Dmbt1, Mbnl1, Nfam1, Lmo4, Znrf1, Ambp, 4930523C07Rik, Bfsp2, Zfp592, Gm2447, Gm16157, Gjd3, Tgtp1, Ston2, Lypd6b, Rnf7, Zbtb2, BC051537, 4930417013Rik, Amt1, Ttc9b, Foxp1, Mir7219, Mrgprb5, Tnik, Dhrsx, Foxp1, Tubb2a, Cyb5r2, Itga4, Snx9, Fam65b, C78339, Mir7212, Ldlrap1, H2-Oa, Snx12, Tdrp, Mndl-ps, Foxp1, Gucy2c, Creb1, Scn4b, Irf4, Rftn2, Gpr125, Dpf1, Fam134b, Akap13, Tmem108, Suclg1, Mn1, Sema4b, Gm6682, Slc46a2, Dennd3, Bach2, Syt12, Grh13, Smad3, 1600014C1ORik, 4930455C13Rik, 3200001D21Rik, Nup153, Grk6, Zfhx3, Fhit, Hmg20b, 4930564D02Rik, Bach2, Slc39a3, Urad, Smcla, Maml1, Zadh2, 8030462N17Rik, Fsbp, Tmem243, Srp14, Lix1, Tmc1, Tspanl1, Tns1, Serpinb5, 1810026B05Rik, Smad7, Mir3108, Phxr4, Tmem131, Olfr1507, Kidins220, Mir378c, Afap1, Rere, Sin3b, Efemp2, Neto2, Mir7669, Tgtp1, Gramd3, Map7d2, Chst2, Sp110, Ccdc162, Igf1r, Mir3110, Dcdc2b, Dse, Dlgap2, Armc9, E230029C05Rik, Gm11944, Tnik, Kat6b, Nkiras1, Tbce1, B4galt1, Cd2ap, Tnks, Icos, Tanc1, Sik1, Torlaip2, 4930453N24Rik, Bnip1, Gm6313, 4930415F15Rik, Inpp5a, Atoh7, 2210417A02Rik, Pdss2, Lamtor3, Ptbp2, Ostm1, Nrarp, Fry1, Mir1907, Gm10638, Sumo1, Zfp60, 1600014C10Rik, Haao, Syde2, Ep300, Ndrg3, Tex2, Cdx2, Eefsec, Tmem131, Mir6959, Fyn, Prkcq, Mica13, Snhg7, Ambra1, Rag2, Vdac1, Ptpla, Tram1, Aak1, Pebp4, Sgpp1, 2410007B07Rik, Itpr2, Tulp2, Mir6395, Elov16, Ppplr3b, Zc3h4, Sptbn4, Rap1b, Vg114, Kcna2, Cnot6, Tbcld1, Pde4d, Rapgef4, Fbxo47, Proca1, Aim, 2310001H17Rik, Tmem131, Sh2d3c, Gtpbp8, 1700030C10Rik, Polr3b, Fam69a, Bcan, 4930465M20Rik, Sbp1, Emg1, Aaed1, LOC102633315, 5930430L01Rik, Ads1, Foxp1, Gm20337, Trdmt1, Gm9920, Foxo1, Olfm13, Fyb, Pgpepl1, Nsg2, Tex26, Fancc, Cngb1, Rapgef2, 2010010A06Rik, 2410007B07Rik, Lbh, Pnrc1, Lad1, Mycn, Abhd15, Cd1d2, 4930428G15Rik, Hnmpl1, Dnaja2, Ccr7, Mmp15, Neto2, Bach2os, Efr3a, Rnf41, Mir7656, Znrf3, Rtkn2, Sesn1, Zp3r, Glrp1, Kdm7a, 3200001D21Rik, Pdss1, 5730403I07Rik, Mmp15, Thrb, Zbtb16, Vkorc1, E330009J07Rik, Dntt, 4933406J10Rik, Sim2, Lgals9, Gm12216, Grb10, Ednra, Fam3c, Birc6, Bace1, Sfrp2, 2010107G12Rik, Zfp184, Ctso, Zfp462, Abcb1a, Gm6639, Mir1258, Dyrk1b, Ra1b, Thrb, S100a6, Gm590, Dnajc1, Zfand3, Blm, Ikzf2, Lrrc32, Nsg2, Foxp1, Tnpo1, Zfat, Specc1, Snora75, Vps45, Acp6, Syde1, Ext13, Fbx114, Cdh26, Celf2, Cd2, Tshz2, Cntln, Fam65c, Dad1, Akap6, Gm15880, E330011O21Rik, Kdf1, Gstt1, 2700046G09Rik, Sort1, Nyap2, 1700063O14Rik, Cog6, Extl1, Vmn2r96, Il12b, Lclat1, A430107P09Rik, Zkscan16, Chl1, Nck2, Cdy1, St6gal1, Mir21c, 2810428115Rik, Cnr2, Rab44, 1700064J06Rik, Zfp191, Peli1, Als2c1, Gnas, 2300005B03Rik, BC033916, Cd226, 1700049E22Rik, Nipal1, Gimap6, Gm5086, 8430436N08Rik, Ift80, Zfp697, Svs1, 4930459C07Rik, Epcam, Zfp706, Pde11a, Slc43a1, Slc9a9, Tshz2, Fbxwl1, Mir7046, Zpbp, 1700123O12Rik, Slc16a1, Gm7457, Tcf4, Fbx112, I19r, Galnt6, Gm5868, Panx1, Hs3st5, Jarid2, Phxr4, Dock2, Nrip1, Lasp1, 1700066B19Rik, Marcks, Plekha7, Wdr41, Pdss2, Gpr83, Rapgef4, Gm15910, Colq, O1fr1507, Vg114, Fgfr1op, Fanc1, Capn1, Lonp2, Rnf38, Gpaa1, 1700016G22Rik, Vmn2r98, Gm7325, Gm826, Rp131, Klrc1, Ikzf1, Crlf3, Cd44, Gypc, AU019990, Fbx113, Tsc22d3, Tgm2, Ptpn14, Fancc, Arhgap26, Tgfbr2, Klf2, Sept7, Ptprc, Btn2a2, 4921511I17Rik, Ppp2r5a, C78339, Arhgap39, Ism1, Mpz12, 2810459M11Rik, Dyrk2, Tspan13, Fbx114, Plat, Celf5, Susd3, Rps6ka2, Gtf2ird1, Naif1, Rsph3a, Tssc1, Ext1, Snora7a, Bc12111, Pip4k2a, Np1, Tmem236, Cox7a21, A530013C23Rik, Rgl1, Pgk1, Ift80, Emid1, Inpp4b, Cldn10, Gls, Tnni1, Folr4, Gm5766, O1fr1507, Hpcal1, Cyth4, St8sia6, 5430434I15Rik, Ropnl1, Serinc1, Mad211, 4921525009Rik, A430107P09Rik, Gm11127, Tra2a, Urb2, Pgpepl1, Cacnald, 5730403I07Rik, Fam49a, 1700025F24Rik, Stat1, Calm1, Kcna7, Eif1, Mir669m-2, Kdr, 1700123O12Rik, Mir8099-2, Hspa8, 2010010A06Rik, Zfp53, 4930524005Rik, Abl1, Uvrag, Slc16a1, Dnah7b, Golph3, Ipcef1, Usp3, Jun, Snord89, Tcf7, Rbpms, Folr4, Papss2, Spred2, Stpg1, Mgat5, Lpin1, D8Ertd82e, Dhx40, Slit3, 4933405E24Rik, Nsun6, A430107P09Rik, Apo17e, Raly, Celf2, Ndufs7, Mir6921, Kbtbd11, Gc, Haao, Gm9054, Slc44a3, Tnfrsf19, Lef1, Ankrdl1, Plxdc1, A430107P09Rik, Zcchc2, Zmat4, Jun, Adamts14, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stk17b, Ceacam9, Ttc1, E130006D01Rik, Camkmt, Ankrd63, Agtr1b, Khdrbs1, Zfp706, Cux1, 4922502D21Rik, Btbd1, Timm8a2, Itga4, Reep2, Uvrag, Cyfip2, Elov16, Tfeb, Spag16, Tbce1, Lmo2, Rasgrp1, Fam86, Ktn1, Fbxo32, Gata3, Ly86, Ptgs2os2, Fam111a, Lac16a, B430306NO3Rik, Tff3, Kcnn4, Mtif3, Ldlrap1, Tmem260, Pla2r1, Basp1, Ncoa3, Ngly1, Ccdc162, Nhs12, Cdc123, Hnrnpu, Arhgap18, Gm6498, Bex6, B630005N14Rik, Dynit1b, Lypd6b, Clec2e, Rbm17, Pst-pip1, Lrp12, Akap2, Camk2d, Igflr, Atpla1, Gsn, Rragd, Actn1, Odf3b, Nudt4, Vmn2r99, Parpl1, Adipoq, Fam221a, I16ra, Kif23, Fabp5, Srpk2, Ikzf1, Fbxw7, Slamf9, St6gal1, Vav1, Serbp1, Reep1, Agr3, P1c12, Kcnj15, Aebp2, Gm20139, Mtx2, Sell', Mbn12, A430078G23Rik, Krr1, Lclat1, Zfp438, 4930487H11Rik, B4galt1, Ifngr2, Olfr221, Asb4, Gm6793, Aplm1, Pdlim5, Gltscr1, 1110032F04Rik, Ankrd13a, Abcd2, Iqsec1, Inpp5a, Pdzrn3, Akirin2, Pip4k2a, Dyrk2, Jun, 4930465M20Rik, Osbp19, Ttc30a1, Ctrmbl1, Tmem243, Olig3, Ubtd2, 4930540M03Rik, Dnajc5b, Denndla, Gadd45a, Rp18, Dapl1, Cd2ap, 6430710C18Rik, Slc16a5, Rcbtb2, Hmgxb3, A630075F10Rik, Ankrd2, St8sia1, Ptk2b, Paqr8, Tox, Wdr37, Stat4, Rplp1, Ccnj, Hspbp1, Mthfdl1, Zcchc9, Gm13293, Camk4, Htt, Usp10, Plekha6, Gm5617, Cnksr3, Mir7218, Lcp2, Cd28, Lbp, Ncoa3, Ski1, Hey1, Mir6368, Akap6, Spin1, Ccdc174, Stambpl1, Ggta1, Pifo, Stim2, Rras2, Tomm201, Gm5538, Skap2, H2-Ob, Zfp3612, Clec2d, Erdr1, Dapl1, Vasp, Cytip, B4galnt3, Hamp, Mex3b, Tcf712, Vps13d, Alox5ap, Mtss1, Gm7457, Fam46a, Taf3, 2810408I11Rik, Ms4a7, Mad211, Selt, Snrpf, Hcn2, Frmd4b, Hivep1, Tspan13, Nfia, Asap1, Nt5e, Misp, Mam12, Sh3pxd2a, Ccdc162, Setd7, Etohi1, Acvr11, Fntb, Shank3, Rhoh, Prok2, Marcks, A830010M20Rik, Ywhaz, Mtss1, Gm8369, Fam188b, Atp2a2, 4933405E24Rik, 4932443119Rik, Notch2, Zc3h12b, Numb, Neb, Ramp1, Zfp831, Impdh2, Grk1, 4930459C07Rik, Mir7035, Setd3, Cdc42se2, Spol1, Fam166b, Mir6419, Atp10d, C2cd5, 4933412E24Rik, Bol1, Calr4, I122ra2, Slc22a16, Syde2, Fyn, Slc27a6, Stx3, Gm6313, Rbm18, Gm13293, Tbc1d8, Fabp5, 4930546C10Rik, Slc16a1, Cnr2, Kcnip2, Trim69, Agbl1, Plvap, Ms4a6c, Usp38, At12, Sh3kbp1, Ppfibp2, Pim1, Pmis2, Sh3pxd2a, Ms4a4c, Klf3, Cb1b, Mir701, Dmwd, Mtss1, Cdk13, Cabp2, Chdh, Pde4b, Ston2, Cmah, Fbx114, Syk, Trio, Btg1, Ski, Cnot2, Stk38, Tm9sf3, 4930482G09Rik, Parpl1, Jarid2, Mam13, 6430710C18Rik, Commd9, Fhit, Scampi, Tcf7, Ncf1, Ric8b, Gm3716, Scm12, Nr2f2, Ssr1, Il6st, Ankrd50, Pnma12, Foxp1, Raver2, Ccdc64, 8430436N08Rik, Klf13, Itga5, Commd3, Mro, Ms4a7, Rock2, Enc1, Rab3gap1, Nav2, Tlr1, Gm7457, Elfn1, Rp134, Agfg1, 1700020N01Rik, Irf4, Gm8369, Olfr1507, Grik4, Akap6, Mir6387, Thrb, Gm20110, Mir7670, Bag4, Gm15441, LOC101055769, Pak1, Mbd2, Ralgps2, Lipg, Gpnmb, Ubash3b, Kntc1, Aqp9, Znrf2, Cmah, Peli1, Chd7, Tmsb4x, Copb1, Gimap1, Bcaslos2, Ppapdc1b, Cdcl4a, Ier5, Susd3, Birc2, Sun2, Itga5, Rlbp1, St8sia1, Hectd1, Chn2, Bcaslos2, Slc39a11, Cdc7, Me3, Stk17b, Ccr4, Peli1, Cd226, 2510009E07Rik, Sh2d1a, Zfp2, Mei4, Chst2, Nipal1, Tbce1, Itgb6, Tmed10, Gm4489, Tmcc1, A430107P09Rik, Abtb2, Tgfbr3, Zfp704, Reep5, Apcdd1, Pik3r1, Ms12, Gm20098, Eif4e3, 5430402O13Rik, Tssc1, Lphn2, Kcnh8, 4921525009Rik, Fam46c, Pum2, Itsn2, Slclla2, Usp6n1, Gimap6, A430107P09Rik, Nipb1, Nrxn3, 1700042O10Rik, Capn3, 4930526115Rik, Plat, Gm15850, Dock10, Shisa2, Wbscrl6, Egfl7, Zfp957, Gm20110, Slc4a8, Ago2, Pnp2, Tgfbr3, Hmga2, Pdlim7, Dip2c, Atplb1, Pxk, Snora26, Gm6498, Sema3d, 3300002I08Rik, 9330175E14Rik, BB123696, Fibcd1, Slc6a19, S100a6, Commd9, Lpar4, Cntn5, Nr1i2, Panx1, Dock2, Ptov1, 5330411J11Rik, Sec24d, Ms4a4b, Eif3g, Rsbnl1, Plxnc1, Jarid2, 1810041L15Rik, Diap2, A630075F10Rik, Klf13, Tlk1, Lef1, Slc4a4, 2610020H08Rik, Tbce, 9430014N10Rik, Slc16a10, 2310042E22Rik, Lrrc3b, St6gal1, Tnfrsfla, U90926, Fam134b, Grxcr2, Dok5, Aldh8a1, Cybrd1, Smarcb1, Jmy, Zfp608, Cdkn2aipn1, Aire, Prps2, Gm839, 4933412E24Rik, St6gal1, Ube2d2b, Mab21l1, Slc23a2, Keap1, Brdt, Piwil2, A930005H10Rik, Fyb, Ncald, Lgals9, Zfp704, Dguok, Gm15706, Nr3c1, Med13, Rictor, Paxbp1, Mir1903, Sv2a, Slx1b, Tbc1d24, Wnt5b, Ccr7, Ptk2, Mir21c, Aox4, Slc35b4, Mgat5, Zfp281, Mycn, 1700016G22Rik, Odc1, Prkcb, Ate1, Ncbp1, 3300002108Rik, Ly6d, Spag16, Clk1, Atg10, 1700030L20Rik, Nsg2, Agps, Golt1a, Cntn5, Cadm4, Malsu1, Frmd4b, Gm6607, Cdh23, Gramd4, Slc44a2, Limd2, Lphn2, 1700010K23Rik, Lrrc66, Akap7, Peal5b, D030024E09Rik, Zscan10, Lsm2, Kcnj13, Cdhr3, Fbx117, Lhx2, Olfm2, Cyp2r1, Wisp3, BB123696, Nlrc4, 2010010A06Rik, Elov16, Eea1, Mir1907, Gls, B4galnt3, Epb4.1, Tshz1, Gpr126, Rgmb, Ncs1, Tet1, Hoxa1, 4930515G16Rik, Usp33, Stk10, K1h16, Ccdc109b, Manba, Gm5111, Chst15, Runx1, Rgs3, Gm4759, Ldlrad4, 4933400F21Rik, 4933406C10Rik, Diap2, Mir6403, Plin2, Zmiz1, Mam13, Fam86, Hbsl1, Inpp4b, Gm14405, Mgat5, Cntn5, Ramp3, Ifnk, Pgm1, Mfsd6, Armcx1, Mir5127, Gimap6, Mir6387, Slc38a2, Gsdmcl-ps, Cd24a, Kmt2e, Csrp1, 9530052E02Rik, Stk17b, Fyb, Lhfp15, Atp8a2, Amn1, Sertad2, Epb4.112, Stk24, Cdk17, Camk4, Rpa1, Zmyndl1, Efcab11, Mir491, Zc3hc1, Vps45, Rgs3, Ube2m, Tspan5, Insr, Snapc1, Btg1, Cox10, Znrf1, Camk4, Ddr1, Gm11981, Sesn1, Commd8, Nrip1, Polr3k, Eya3, Ppplr1b, Pcdh7, A430107P09Rik, Efcc1, Mtss1, Hpn, Armcx1, Gm20139, Alg14, Sec11a, Cyb5d1, Trpm1, Fam65b, 5730508B09Rik, Frmd4b, Gm10584, Gm5069, Pmepa1, Sell, Mir6413, Klf12, Rhoq, Plc12, Prrc1, Emp1, D030024E09Rik, Rnf145, Bach2, Prkcq, Hic1, Msmo1, Map3k7c1, AI854517, 4922502D21Rik, Vti1a, Zcchc9, Spats2, Mir7681, Wdr89, Bc16, Cytip, Gm13293, Creb314, Peli1, Pak1, Efcab11, Usp7, 4931403G20Rik, 1700030A11Rik, Mvb12b, Ampd3, Cubn, Baiap3, Med30, Actb12, Kat6b, Peli1, Tmevpg1, Nsf, Hpcal1, Ube4b, Fam110b, C330011F03Rik, Inad1, Sesn3, Tmem30c, Itgb6, Dlg1, Srp14, 3300005D01Rik, Ggact, Mir21c, Cyp2s1, Mir7061, Bach1, Insr, 2410114N07Rik, H2-Eb1, Tasp1, Tusc3, Irf2bp2, 1700056E22Rik, Ppp6c, Slain2, Cnn3, 6030407003Rik, Acbd6, Hmgb1, P2rx4, Cdk19, 1700061G19Rik, Tesk2, Plxnc1, Ercc3, 2010010A06Rik, Stk17b, Tspan9, Kcnj16, Ddx10, Wnt16, Sp4, Hilpda, Slc38a6, Tgfbr2, Fggy, Sugct, Begain, Mnd1-ps, Ksr2, Eif2d, Ms4a4d, Stim1, Cst10, Nfatc1, Ppifos, Gng7, Mir211, Txk, 4930415F15Rik, Tmem64, Stim1, Pip5k1b, Kcnj15, Commd8, Mir3108, Atpl 1b, Stk17b, Emc3, Cldn10, Akap13, Abcb1a, Mthfdl1, Foxk1, Rgs3, Gdnf, Micu1, I17r, Arhgap35, O1fr1364, Ms4a4b, Rgs10, Flt3, Sfrp2, I19r, Sf1, Gm1604b, Galnt4, Dtnb, Supt20, Fntb, Zmyndl1, Tulp3, 2410007B07Rik, Tsen15, Abhd2, Dgcr6, Filipl1, Ift81, 4933401D09Rik, Gtdc1, Ano6, Mir1928, Peli1, Jak1, Cdk19, Syne1, I123r, Tpm2, Fam65b, Kidins220, Vav1, 9030617003Rik, C1q13, Ceacam9, Ehd2, Vtcn1, Dusp7, Pik3ip1, Ostm1, Ppard, O1fr372, Mir7032, Npy, Phxr4, Grap2, Thrb, Wipi1, Dock4, Mfsd6, Zmynd8, Mylip, Setx, Ccdc146, 1112a, Sa113, Mir7048, Hapin1, Casp3, Bbs9, Syne1, Tdrd3, 4930565D16Rik, Gm20098, Tcf4, Haao, Snd1, Zfp706, Agfg1, Gm8709, Syne1, 4933406J10Rik, Pik3c2b, Manba, Olfr1033, Aurkb, 9330175E14Rik, Foxo1, Sfmbt2, Bach2, Pogz, 4930459C07Rik, Phxr4, Map7d2, Gm20750, Il12b, Sesn3, Psen2, Suco, Mad211, E030030106Rik, Gadd45a, Abca1, Boll, 4930430F21Rik, Cstad, Lyst, Rasgrp4, 4833427F10Rik, Ehd2, 4930445N18Rik, Ppm1h, Gltscr1, Irf8, Lgi1, Gm10432, H2-M10.1, Crtc3, 4930453N24Rik, Irs2, 1700042O10Rik, Rabgapl1, Rnf144a, Csk, Rpia, A430090L17Rik, Mir8097, Serbp1, Mir684-1, Tcf4, Commd8, Tet3, Nr1i2, Gm10190, Prkcq, Orai2, Dpy30, Sbk2, Tssc1, Cd5, Sipa112, Dcpla, 1810006J02Rik, Itgae, D030025E07Rik, Wibg, Bach2, Irf4, Ctnnd1, Usp7, Rftn1, Themis, 4930440119Rik, Thrb, Nr1d2, Tgtp1, Ccdc162, Atp8b2, Speer4f, Stra8, Gm4906, Fam46c, Pag1, Etv3, Erdr1, Dhrsx, Fam65b, Gosr1, Trem2, Fbln1, Sp3, Mef2a, Bcor, Map4k4, Magi2, Pak2, Rph3a1, Lgi4, Pja2, Tceal3, Efcab11, Arhgap5, Ext1, Smyd3, Prim2, Satb1, Stag2, Themis2, Pim1, Apol8, Lrrc6, Shb, Magi2, Commd8, Zfp879, Trp53i11, Rgl1, Abcd3, Diap2, Zbtb2, C030016D13Rik, Arhgdib, A630075F10Rik, C730036E19Rik, Phc2, Adamts10, Inpp4b, Cd200, Itpr2, Fgfr1, Gm5434, Scn2b, D8Ertd82e, Gm2a, Ube2v1, Bend4, Lpp, Mir181a-2, Gm13293, P2ry1, Klf7, E030018B13Rik, Rhobtb2, Ddr1, Ggnbp1, Gimap7, Mamstr, Cmip, Setbp1, Fcgr4, Slc1a3, Zfp608, 2810403A07Rik, Gm7538, Mir378a, Hoxa13, 2610301B20Rik, Ngly1, Sergef, Tpp2, Slc35b3, Mam13, Nav1, Txk, Fam195a, Scm14, Tlr12, Gpr125, Zfp3612, Suclg2, Tec, Akap2, Rab38, C030018K13Rik, 4933433H22Rik, Osbp111, Capn13, Ankrd50, Mir1928, Mir3108, Slc39a10, Dock2, Dip2c, Aebp2, A530046M15Rik, Gm6251, Mtx2, Exoc4, Olig3, Dph6, Emb, Xpc, Gm7538, Tnfsf8, Afap112, Cenpv, Gsn, Rbms2, E2f3, Smarce1, Foxp1, Slc37a3, Apbblip, Tex10, Bend4, Pcgf5, Trio, Klf5, Gja8, E130006D01Rik, Ncor2, Acbd6, A1g14, Scmh1, D830013O020Rik, Galnt4, Ndufa6, Timm8a2, 2210010C04Rik, 4931403E22Rik, Gys2, G630090E17Rik, Dap11, Nup160, Fxyd7, Zscan18, Bid, Serh1, Cdk17, Lrtm2, 3930402G23Rik, Tm2d1, Snora7a, C8g, Nkap, 2410007B07Rik, I1f3, Mir7017, Gpr83, Thada, Ambra1, Fancc, B3galt4, Thnsl1, Etv5, Aox2, Tgm2, Manla, Edem1, Hnrnph1, Atp6v0e2, Clec4f, Hey1, Fam3c, Stat4, Slc46a1, Rps15a-ps6, Kdm4c, Upb1, Sik1, Nceh1, Prkcq, Btg1, Galnt2, 2010010A06Rik, Neu3, Cubn, Mir1928, Rapgef2, Nedd41, Egfl7, B3gnt2, Tgtp2, Gm13546, Ext1, Pold4, Ggact, B3gnt7, Gm5868, T1r7, Lefty2, Npff, Tcf712, D130058E03, Pag1, 4930578N18Rik, 6430710C18Rik, Fam43a, Snora81, Cyp20a1, 4922502D21Rik, Lsm1, Gm10791, Kcnh2, 1700109K24Rik, No16, 4922502D21Rik, Trib2, Nrf1, Rgag4, 4930426L09Rik, Ppi13, Vmn2r96, Ngly1, 1810046K07Rik, Hid1, Olfr1510, Nrip1, Dhtkd1, Ms4a6b, 4930583K01Rik, Atplb3, Mir7046, St8sia1, Pcdh7, Micalc1, D030024E09Rik, Pold4, Coro2b, Adamtsl4, Auh, Fus, Hcls1, Prkcq, Nimlk, Zdhhc14, Kcnh2, Cd37, Ttc27, Olfm2, Ubac2, Mir6387, Zfp619, Zbtb9, Gpr125, Ppp2r5a, Adgb, Pard3, Ctr1, Ddr1, Ckmt2, Lpar6, Sspn, Gm4792, 9430008CO3Rik, Ngly1, Tbx19, Heatr1, Cdc14a, Nabp1, 8430436N08Rik, Cd247, Llph, Pex10, Eea1, Lef1, Ly75, Dockl1, Haao, Rgs3, Mndl-ps, Maml1, Stxbp1, Parpl1, G530011O006Rik, Mgrn1, Ift57, Mef2a, AI427809, Ldhb, Cdk19, Lrrc3b, Osm, Dnajc15, Mirlet7i, Stk38, Cep170, Rcn3, Gramd1a, Mfng, Vg114, 1700017N19Rik, Atp1a3, Ptpla, Mir6962, Jun, Cdk19, Gm10638, Zfp3612, Slc39a10, Tpd52, Mthfdl1, Agbl1, 4922502D21Rik, Ceacam2, Drosha, Fut8, Cox10, Dnajb12, Thns12, Eefsec, Pgpepl1, 4932441J04Rik, Fndc7, Clip1, 2700046G09Rik, Itpkb, Kremen1, Mpp6, Ccr9, Tbcb, Rictor, Gm3716, Icos1, Cpeb4, Mir7681, Kmt2c, Mak16, Gli1, Act19, Gpatch2, Sept14, Aebp2, Phlpp1, Zfp957, Ap3m2, Zcchc2, C030018K13Rik, Cdk17, Tmem217, Cog6, Dock2, Il7r, Crybb2, Slc16a10, Ppplr1b, E430016F16Rik, Fbxo17, Akrld1, D10Jhu81e, Irgc1, Klf7, Pcdh7, Nipb1, Rrn3, Mir7681, Arhgef33, Rhoq, Dusp5, Itga4, Palm2, Map10, Tigd2, Mfge8, Zfp580, Peli1, Trim59, F730035M05Rik, Gpr110, Lyst, Slc10a4, C230029M16, Gpnmb, Rgs3, Rab3ip, Vps54, Cox7a21, Slc7a15, Serbp1, Slc22a16, Prkch, 4933433H22Rik, Arap2, Mk11, Slc22a16, Fli1, Stk24, Stard8, Arhgap29, Pcca, Trem12, Tssc1, Pgpepl1, Syde2, A430107P09Rik, Foxo1, 8430436N08Rik, D030024E09Rik, Tcf7, Ifitm6, Ctso, Capzb, Lypd3, Lix1, Ccdc170, Tasp1, Dnah7a, Sugt1, Pde7a, Pcnp, K1f5, Olfr1357, Ldhal6b, Kctd12b, Cxxc5, Pkn2, Mboat2, Angpt1, N6amt2, Gm839, Bach1, I12ra, Ankrd12, Ccdc64, Pptc7, Ikzf2, Svil, Tlr1, Rell1, Tma16, Mbnl1, Cyfip2, Rps6ka2, Elov16, Dap11, Zfand3, Unc5c1, Zfp619, Syt13, BC031361, Fam26e, Gm2799, Chst15, LOC101055769, Sepp1, a, Ccdc171, Hemgn, Pik3c3, Lrp12, Capnl1, Pvr, Prkcq, 4932702P03Rik, 2300002M23Rik, Tef, Foxp1, Lypd6b, 4933412E24Rik, Wnt4, Marco, Elfn2, Smim9, Dip2b, March2, Frs2, O1fr1507, Mir7219, Fbx122, Vim, 4933432G23Rik, L3mbtl1, Madil1, Calr4, Lrrc3b, Strada, Mir363, Tspan9, Esrp1, Panx1, Tgfbr2, Emb, Spata3, Ext1, Calm2, AY512915, C530008M17Rik, Mitf, Wdr11, Mir5127, Selt, Gm6623, Gm684, Gm3716, Tgtp2, Sptb, Hamp2, Itgb6, Cd2ap, Pmp, Ift80, Slamf6, Pou2af1, Snx29, G530011O006Rik, Wipf2, Fam134b, 4930428G15Rik, Ig111, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, Tecta, Mir7687, Mir6367, Itga4, Tns4, Ccm2, Wipf1, Cerk, Znrf1, Elov15, Phtf2, 1300002E11Rik, 2210417A02Rik, Mir7061, Grhpr, Mark4, 4930564CO3Rik, Svop1, Pja2, Tfdp2, Rbml1, Usp6n1, Mir6368, A430107P09Rik, Bc12, Cdc42se2, 4933433H22Rik, Apo18, Xpnpep2, Dach2, Mir205, Stard5, Fsbp, Rph3a1, Vav3, Gm10125, Lpcat1, Cd2ap, Bank1, Smurf1, Aox2, C230029M16, Sgms1, Eci3, Xpnpep2, Pfkfb2, Utrn, Ldlrad3, Gabrr1, Kcna2, Ywhaz, Stard13, Atp1Oa, S1c39a10, Whsc111, Gm12522, Trio, Manlc1, Hmha1, Gm10791, Kidins220, Lad1, Mir1928, Gm13710, Mir1963, Lama4, Pard3, Susd3, Taok3, Skor2, Matn2, Tet2, Mir7674, Ccdc64b, Fam49b, 4933412E24Rik, Thsd1, Sa113, Papss2, Tcea13, Rreb1, Klrd1, Rgs3, Cst10, Itga4, Gm20098, Smarca4, Cyp2d22, Kdm6b, Cntn5, Dyrk2, Dusp10, Srpk2, Etv5, Slc25a25, Cfl2, Micu1, Ets1, Gm6559, Zfr, Mrp152, Cerk, D630010B17Rik, Ext1, Cb1b, Gnai2, Apol7e, Manba, Dusp10, Smim8, Mir6907, Pard3, Tmem35, Ric8b, Gm14124, Pik3r1, Gm11981, Dip2c, Plin2, Fam228a, Tlr1, Lypd6b, Zc3h12b, Abcg1, Ext1, Camk2g, Ptgr2, Mndl-ps, Rftn1, Sox8, Sdc3, Mab2113, Arid1b, Tdrp, 4921525009Rik, Arid4b, Micu2, Ly86, Afp, Grap2, Ist1, Sh2d4b, Rad52, Mir1668, Rpgripl1, Gramdla, Sgk1, Fos, Smad4, Hdac4, B3gnt3, Nr4a3, St8sia1, Psg-ps1, Act19, Pdk1, I12ra, Irf2, Fas1, Hsdl1, Galnt5, Itk, Mam12, Erdr1, Ndufa6, Tbc1d23, Slc43a2, Iqgap1, Klf7, Bend5, Klf4, Lif, Calr4, Cnst, Ifnk, G3bp2, Tbc1d2, C030034L19Rik, Zfhx3, Bc111a, Rein1b, Ap3m1, Hlcs, Serpinf1, Gm16390, Wdr37, St8sia1, Cenpu, Gm10638, Tfpi, Fabp7, Wisp3, Psma1, Tet2, AI854703, Lmo4, Ppplr1b, Mgat5, Foxp1, Gm3716, Mir6349, Tle4, Itgb8, Rabl 1fip4, Tbce1, Npepps, 1300002E11Rik, Celf2, 4933412E24Rik, 4930415F15Rik, Olfr1507, Itgb3, Bace1, 2010015L04Rik, Mir7656, Esrp1, Spred2, Myo10, A930001A20Rik, BC048403, Lincpint, Mturn, Shisa2, Mef2d, Rac2, Dusp6, Lef1, Tmem64, Lrig1, Atp6v1g1, 1700017N19Rik, Dfna5, Zfp286, Gimap9, Gbe1, Cdc37, Pard6g, Serp2, Pid1, 4930465M20Rik, P2rx4, Opalin, Mir684-1, Ngly1, Ndufa4, Mir16-2, Trib2, Slc17a9, Itpripl1, Uri1, Rnf32, Pr1r, Lyrm7, Fbln1, Nenf, At12, Slfn1, Supt20, Ski, Pno1, Foxo1, Olig3, 5330411J11Rik, Eci3, Clic4, Naa30, Abca1, Mpp1, Adcy6, Ptprc, Fbxo27, Ahcyl2, 1700016K19Rik, Gm14405, Drosha, Lrrc1, Mir7014, Cdk19, Ldlrap1, Pgpepl1, Fg12, Nck2, Acvr2a, Myo10, Cb1b, Gm590, Kcnq5, Co16a1, 4930480M12Rik, Rad23b, Tram2, Pygo1, Mir6368, A430107P09Rik, Afap1, Pip4k2a, Slc46a2, Mgat5, Slc27a6, Ntper, Cuedc1, Ramp1, Enthd1, Mir6374, Stmnl-rs1, Gm684, Fbin1, Lef1, Chd7, Ppplr3fos, Abi1, Plau, Aifl1, Tesc, Edem3, Tbce1, Prdm5, Lnpep, Dyrk2, Gm6260, 4930428G15Rik, Carns1, 8430436N08Rik, Plekha5, Hexim2, Ccr7, Foxp1, Satb1, Rpgrip1, Dnm3os, Retn1b, Tram1, Tmppe, Car12, Snordl4c, Ets1, Crtc3, Kcnh8, Hey1, Slc44a2, Dip2c, Ankrd44, C230029M16, Nwd1, Mrpsl1, Cpb1, 4930567H12Rik, Mir378c, Dnaja2, Fnbpl1, Tab3, Zap70, Cenpk, Bcar3, Usp6n1, Ppp4r2, Has1, Tbc1d22a, Dync21i1, BC055111, Sepw1, Ap1s3, Ass1, Metrn1, Rsph3a, Dpys12, Rapgef6, Cxcr4, Mir8095, Sgsm3, Actn1, Grb10, Slpr1, Rasgrp1, Dnajc6, Agfg1, Map3k15, 4930465M20Rik, Csnk1g3, Trpv5, Klf3, Zfp3612, Mir181a-1, S1c30a9, Taf3, Em12, Tssc1, 1190002N15Rik, Cdh26, Sav1, Ghsr, Msra, Fam134b, Tusc3, Itpkb, Dtwd2, Frmd7, Gm20750, 4933440M02Rik, St8sia1, Mir8105, Mir7681, Sntg1, Hipk2, Cd8b1, Stk24, Zmat4, Pnoc, Creb1, Trps1, Gls, Gm15706, Ubtd2, Kif1b, Pex3, Ect21, 4732490B19Rik, Calm2, Syne1, Aplb1, Ldha, Mmp15, Tnks, Gm20098, Spred2, Igf2bp3, Atp1a3, Pdzrn3, Qser1, Ppm11, D930032P07Rik, Vmn2r98, G530011O06Rik, Ikzf1, D630010B17Rik, Mett18, Gm590, Enthd1, Ccdc152, Ywhaq, Atp8a2, Thra, Ildr1, Rpap3, Ltb, Rev31, Med131, Dner, Ralgps2, 4930428G15Rik, Dnajc1, Arhgap6, Fam101b, Nfam1, Ccr7, Psma6, Gm1631, Hadh, 3425401B19Rik, Irf4, Zak, Brdt, Fam71f2, Slc25a12, Ippk, Fnbpl1, Rps16, 4930540M03Rik, Cd5, Ube2e1, A430107P09Rik, Rapgef4, Olfr1507, Rmdn2, Lhfp, Mir1893, Lgals3, Gn131, Whsc111, Sh2d1a, BC061194, Mbn12, Zbtb38, Golph3, 4930430F21Rik, H2-Q1, Ntrk3, Ninj2, Cd3e, Stat5b, Lbx1, 4933412E24Rik, Pten, Gm2447, Mtx2, Tmcc3, Lin28a, Cyb5a, Znrf1, Fancc, 1500015O10Rik, Plekho1, Prss32, Gjd2, Gphb5, Ccr7, 4931403G20Rik, Mboat1, Dyrk2, I19r, Sos1, Etv2, Txnip, Fam110b, Rph3a1, Mboat4, Plekhh2, Irf6, Thoc7, Yeats4, A430107P09Rik, Ms4a7, 4930567H12Rik, Zfp930, Zap70, Uaca, Nsg2, Myo10, Ctf1, AU015836, Mir7681, 9830132P13Rik, 1700021F07Rik, Ipo4, Icos1, Smad5, Cyp26b1, Mgarp, A430078G23Rik, Kdm6a, I730028E13Rik, Hs2st1, Tox, Akrld1, 1810010D01Rik, Rp134, Ramp1, Hcls1, Rab3ip, 4930445N18Rik, Ext13, Sox4, Gjd3, Gm14305, 1700061F12Rik, Lnpep, Wnt5b, Mark4, Stmnd1, Olfr1507, A430107P09Rik, Commd8, AI427809, Mir6979, Cdc42se2, Gpr125, Tcf25, Taf8, Lclat1, Wdr89, Ptk2b, Pitpnb, Ttf2, St6gal1, Mam12, Lrch3, 5430427M07Rik, Bach1, Exoc4, Mef2d, Vps37b, Wdr37, Ccr7, Fam221a, Mif, Vmn1r157, Mpp6, Chd2, Sept6, She, Prg4, Snord83b, Gm7616, 2410114N07Rik, Wdr37, Gdpd4, Vdac1, Mir5104, Rsrc1, 4930523C07Rik, Akap2, Lyst, G6pc2, K1h14, Slc35b4, Setbp1, Akap2, 1700072005Rik, Gm1604b, Kcna10, Stambpl1, Npas2, Dnajc1, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrod1, Tm2d1, 4930572O13Rik, A130077B15Rik, Lck, Kdm2a, Rbbp8, Cd47, Gm6578, Klf2, Zfp536, Ube2e3, Aff3, Man1a, 4930413G21Rik, Crtam, Rpa1, Kcnh3, 2900008C10Rik, Tbc1d31, Snn, Malat1, Bambi-ps1, Wisp3, Mrgprb5, Gch1, Nabp1, Mett19, Zfp3612, Mir7669, 4933401H06Rik, Prkrir, Erdr1, Olfr630, Tmem168, Gbpl1, Mbnl1, Plin2, Scn2b, Car8, Ngly1, Kcna2, Dpp6, BCO27231, Gosr1, 1700016L21Rik, Ccdc170, Manba, Osbp19, Purb, Rftn2, Klf3, Cdca71, Supt71, Rgs3, Rbpms, Mir6349, 5830418P13Rik, Pkn2, Basp1, Btg2, Ifnk, 5730403I07Rik, Srsf1, Kif3a, Fbxo27, Gipr, Colq, 4930540M03Rik, Pard6g, Bc111a, Ezh1, Cd2, Foxq1, Rybp, Pgap1, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhc18, Mroh2b, Gpr3, Tgfbr2, Reck, Atxn713b, Ngly1, I112rb1, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4i1, Slc7a1, C9, Mir6374, Mdm1, 2310043L19Rik, Fbx117, Gm5468, Panx1, Sct, Racgap1, Ppm1b, Samd12, E330009J07Rik, Cd101, Zcchc2, Gad11, Rapgef6, Steap3, Fgfr1op, Setd7, 3110056K07Rik, Gm5538, Ino80e, St6gal1, Nsmce1, Ccdc64, Cxcr4, Gata3, Cerk, Chst15, Mir3089, Map4k4, Akap13, Slc30a9, Gm10790, Npffr1, Tdrp, Gm20098, Ddhd2, St8sia6, Lhx2, Syt6, Dt1, Themis, Mam12, Sh3bgr12, Sptbn1, Fam207a, Lmna, Nfatc2, Gm12185, Arhgap6, Atg14, Macrod2, Mir3110, Fam46c, Wdr63, Ppp2r1b, Prdm9, Lphn2, Mir574, 119, Elov16, Chd7, Pitpna, Atoh7, Mc2r, Celf2, Tdrd3, Rassf2, Gm10640, Ncoa3, Lyst, Fyb, Gm2447, Aplar, Stag2, Foxp1, Rock2, Pdlim1, Bin1, Gm10125, Bach2, Fbx122, 2900005J15Rik, Rgs2, Cldn10, Lrrc8d, Rad23b, Supt20, Dgkd, Atn1, Agtrla, Pias2, Gm10791, Tmem60, Prkag2, P4ha2, Trat1, March5, Tcf7, Wbscr27, Gm6498, Hist1h2bn, Zfp120, Trub1, Mir1936, Ms4a7, Nfatc4, Lrm3, Trat1, Sox4, Nhsl1, Lincenc1, Tmem243, St6gal1, Dpys12, Cntln, I17r, Olfr9, Erbb2ip, Rp1101, Mir211, Srbd1, Lphn2, Fam3c, Sorcs2, Thrb, Katnal1, Mir199a-1, Fbxo32, Rpap3, Arfip1, Rp119, Itm2a, Trim56, Ier51, Btg1, Plekhb1, Rp134, Pik3r1, Mir6349, Ikbkb, Cntn5, Sh3kbp1, Btg1, Cd101, 4930523C07Rik, Qsox2, Serh1, Rfc1, Cga, Bmyc, Sla, Rev31, Fam134b, Ggact, Mir466o, 28-Feb, Akrld1, Tnfsf11, 2310040G24Rik, Gcic, Pde4b, Dgkz, Hsbp1, Eif3k, Gipc3, Mthfdl1, P2ry1, Ets1, Cxcr4, Pja1, Trem12, Ccr7, C230024C17Rik, Rps6ka5, Klf4, Cx3cr1, Echdc3, Hspa8, Lama4, Mg11, Ophn1, Thnsl1, Disci, Pdzrn3, Sms, Zfp704, Zfp3612, Fam105a, Mad211, Dazap2, Fbx114, Vapb, Ifnab, Zgrf1, Rtkn2, Ppp2r3c, Vmn2r96, Bbs9, Ifn1r1, 1700064J06Rik, Ppp1r37, Tgfbr2, Slc2a2, Lef1, Ccr7, Foxq1, Gan, D6Ertd527e, Snx9, Hes7, Fbxo47, Cox10, Bend3, Sgms1, Slc30a9, Gm3716, Foxo1, Rsbn11, Tmc1, Fam120a, Gpr18, Efhc1, Ramp3, She, Akap7, Vezf1, Dnajc3, Tnpo1, Nudt1611, Gm19589, Ankrd60, Txk, Lix1, Dnajc6, Serinc5, Lef1, Tars, Gm3336, Bace1, Nedd41, Trib2, Gm6994, Bc111a, Mir5127, Klrb1b, Nfix, Tigd2, Map4k2, Uxs1, Bach2, 4930583K01Rik, Klhdc9, Eepd1, Als2c1, Pard3, Wdr27, Ikzf1, Btg1, Ly6e, Prm1, Taco1, Itpr2, Limk2, Bend4, Gtf3c3, Kcnh8, Cd96, Fam229b, Adamts14, Lyrm7, Fhit, Sqrd1, Fpr-rs4, Tmem260, Cd55, Mir214, Mir3093, Amigo2, Dapp1, C030018K13Rik, A230028O005Rik, Shf, Lef1, Nrp1, Efr3a, Tmem30b, Mynn, Tgfbr2, Nfia, Ipcef1, At12, Thpo, Fam49a, Mir6387, Rtkn2, Gucy1a3, Chrna9, Rassf2, Clip4, Wnt10a, Opalin, Llph, Mir6995, Sorcs2, Slc2a2, Gm20110, Syne1, 2810001G20Rik, 5430434115Rik, Ppp1r37, Itgb6, Hspa8, I19r, Glrp1, 5430421F17Rik, Tstd2, Zswim2, Ext1, Slc16a10, Zfp957, Slfn5, Lrch1, Scin, Cardl1, Ext1, Tet1, Scm14, Diap2, 4933433H22Rik, Zfp629, Tspan13, Prkcq, Zcchc13, Cd74, E330017L17Rik, Tm2d1, Gpr126, Nm1, Fam124b, Tubb2a, Tdrp, Tnfrsfla, Foxp1, Fam107b, Epb4.115, Fam78a, Rasa12, Mapk9, Creb312, 4930539M17Rik, Kcmf1, Ctage5, Ankrd12, Manba, Tmc1, Lmanl1, Nacad, Agr3, 4933433H22Rik, Matk, H2bfm, Kcnh2, Pgr151, Inpp4b, Kcmf1, 4933430N04Rik, Vmn2r92, Stk17b, Foxp1, Cep5711, Lix1, Kcnal0, Vang12, Treh, Enthd1, Gm6559, Brf2, 4921525O009Rik, Prkcq, Igsf3, Fut8, Limk2, 5730508B09Rik, Clasp2, Twsg1, Tmem126b, Hoxa7, Cd28, Sh3bp5, Furin, 1700001P01Rik, Diap2, Tecta, Icos1, Fl1r, Mir7023, Fes, Map3k5, Spry4, Cd44, Ralgps1, Gm16793, Alox5ap, Mir5098, Arid1b, Ugcg, Ctla4, Snx9, Mir8095, Is12, Osbp16, Dyrk1a, Cd300a, A930011G23Rik, Fam26e, Ikzf2, Enpp6, Mir181a-1, Lyst, Grh12, Aldhla7, Hmgbl-rs17, 2410004B18Rik, Dnm2, Nabp1, Foxp1, Tnfrsfl0b, Prkcq, Sgsm3, Agr3, 1700017N19Rik, Tle3, 4933406K04Rik, Insr, Whrn, Ets1, Lef1, Mir5618, Soat1, Ccr7, Cmss1, Ahcyl2, Mgat1, Hspa13, Znrf2, Kcnh8, Tdrp, Gm1604b, Vmn2r95, Akap6, Tbc1d22a, Lbp, Mk11, Rsu1, Sstr2, Slc37a3, Ube2d2a, Itpka, Rnf220, Hnrnph2, Gm2933, Akap2, Pdzklip1, Wwp1, Vapb, Dyrk1a, Dynit1b, Zfp365, Ssh2, R3hdm1, Nek10, Zswim2, Ccdc90b, Znrf1, Ms4a5, 4933406K04Rik, Actr2, Rgmb, Ston2, Gnas, Stk17b, Pim1, Mtr, K1h12, Cdk15, H2-Ob, I123r, Slain2, Tssc1, Sbk1, Ube4a, H2-T3, Gtf2ird1, Tyw5, Hbsl1, Efhc1, Rpe, March6, Itga4, Fam13a, Lst1, Ankrd55, Nif311, Fam69b, Mir7674, 2810001G20Rik, Gpr19, 4930567H12Rik, Foxp1, Dgkz, Cenpf, Amigo2, Panx1, B4galt3, Pag1, Ub13, 1110059E24Rik, Hs1bp3, Slc6a19os, Mdm1, Limd2, Slc6a19, Bank1, A1g13, Wisp3, Suit5a1, Fam86, Dennd2d, Cacnb2, Tesc, Mdm1, Adipoq, 1810026B05Rik, Mir325, 1700096J18Rik, D030024E09Rik, G0s2, Mir7219, Slpr1, Cxcr1, Ext1, Chd1, Ly86, Dhx40, 4930564D02Rik, Dctn6, I17r, E230025N22Rik, Sgk3, Bach2, Ramp1, Syt6, Gsap, Ccdc152, Jakmip1, Atp8a1, Grap2, Dynitlf, 4921513I03Rik, Gpc6, Kcnal0, Ipcef1, Mir7061, Btg1, Stoml1, Zfand3, Aqp4, Zfp281, Ccr2, Nrip3, C230029M16, Tcf4, Hadh, Mthfdl1, Lhfp, Gpr114, Plbd1, 1110034G24Rik, Cd79a, Gse1, Churc1, Map3k7c1, Filipl1, Galnt7, App12, March5, Zswim6, Skap1, Tgfbr3, Slc16a2, Pa11d, Atg10, Cap2, Dfna5, T1r7, Slc24a1, Hivep2, Dock4, Cd300a, Igf2bp2, A430107P09Rik, Lrrn3, March2, Gm21057, Apbblip, Piga, Zbp1, A430107P09Rik, Trappc8, Zdhhc14, Stk17b, Sh3pxd2a, Ppifos, Chd1, Socs1, Kdr, Gramd3, Urad, Sipa111, Gm20098, P2ry2, Gas8, Sox5os3, Ccdc117, A130077B15Rik, Basp1, Zfp365, Syde2, Laptm4b, Sik1, 4933433H22Rik, Npff, Arnt1, A1b, Zmyndl1, Gm20098, 119, Hadh, Sstr2, Emp1, Lef1, Galnt10, 5430434I15Rik, Cmah, 4631405J19Rik, Hesx1, Gm16793, Rp1p0, Sa113, Xdh, St8sia1, Folr4, Sp3, Rassf3, Aox2, Emp1, Rragc, Proser2, Gm8817, D030028A08Rik, Btg1, Mad211, Upb1, 1810006J02Rik, 4932702P03Rik, Rhoh, Gm10790, Dock10, Fam166b, Pcdh1, Zbtb24, Camklg, 4933407L21Rik, Pde7a, A430093F15Rik, Pmepa1, Ropnl1, Grap2, Rims3, Rps6ka1, Eps15, 4930445N18Rik, 6430710C18Rik, Ppplrl3b, 1121r, Mtmr2, Prex2, Atp6v0d2, Ablim1, Hnrnpd, Syde1, Slc16a1, Mbnl1, Sgms1, H2-DMb1, Ly6a, Tlr1, Gm20098, Galnt5, Edem1, Fam173b, Gpr126, Nbeal1, Prlr, Tmc1, Csrnp1, Atp1Oa, Dusp4, Lpar6, Pitpnb, Actr2, Ago2, Lphn2, Gm2447, Myo18a, Cd101, Cngb1, 1700027J07Rik, Vmn2r91, Folr4, Satb1, Man2a2, Smim14, 3300005D01Rik, D130058E03, Angpt12, Ercc3, Tmem87a, Syne1, Ptrf, Gm2447, Zscan2, Bend4, Endod1, Tgfb3, Mir6962, Rragd, 4931403G20Rik, Ddr1, Map4k3, Fabp4, Stk17b, Gm5122, Rapgef4, Neurl1b, Pdgfrb, Cirh1a, Fnip1, E030002O003Rik, Fam65b, H2-DMa, Btg1, Zc3h12b, Prkch, Sipa111, Tdrp, Adtrp, Fam129c, Runx3, Hvb1, Tbx19, Filipl1, A430107P09Rik, Ccdcl1, Lphn2, Spgl1, Mir6395, Foxp1, Dtnb, Mrp113, Egln3, Fpr1, Rapgef4, A130077B15Rik, Th7, Rbpms, Gm1966, Tmem150b, Rev31, Mad211, Gm1604b, Tasp1, Slc19a3, Trappc10, Ralgps2, Npas1, Ptprs, Slc36alos, Maf, Wdr12, Polr3k, Gm20750, D14Ertd670e, Fam46c, Fam46c, Ptger1, Lclat1, Ptma, Actn2, Tspanl1, Zfp879, Spred2, Satb1, Nabp1, 4930486L24Rik, Ugcg, Txk, A430107P09Rik, Hadh, Abtb2, Rbm33, Fli1, Fyn, Mgat4a, Snd1, Glt8d2, H2bfm, 9130401M01Rik, Snd1, Mir3079, Pcdh7, Cnga1, Tldc1, Ugdh, Aven, Mir8104, Rgl1, Sox6, Map3k14, Akirin2, Mir684-2, Rfx2, Fyb, Ccdc711, Ece1, Gm8884, 4921507P07Rik, Mir6933, Slc6a7, Cox7b2, Rfx4, Gm5617, Sh3kbp1, Pds5a, 9030617003Rik, Gpr126, Ctnnbl1, Prpf40a, Gpr22, Cldn10, Cdk19, Sgk3, Rgs3, Mir6995, Cdon, Stk17b, Samhd1, Gm16793, Lag3, Olfm2, Cyb5a, Zfp438, Akap2, Dpf1, 3110052M02Rik, Lrp6, Haao, Camk2a, Tspan9, 543043415Rik, Stk24, T1r12, A930005H10Rik, Slc4a4, U2af1, Fbx121, Opalin, Rybp, Igsf3, Aim1, Wasf2, Rgs3, Frs2, Smok4a, Pak4, Zscan22, A430107P09Rik, Slc35b3, Serpinb5, Med30, Cdc16, Agfg1, Tmem261, Plxna1, Myo5c, Gpr183, Suclg1, Cdk19, 4930556N09Rik, Lpp, Tmem260, Ubqln2, Mir378b, Btla, Gm19589, Ano6, Clint1, Ube4b, Olfr1507, Rab33a, 4930523C07Rik, St6gal1, 1600014K23Rik, Nnmt, Ift80, Htr3b, Rp134, Ipcef1, Psma6, Dnmt3a, Hpgds, Stxbp3a, Mir6907, 1700056E22Rik, Smad7, Mir7078, Mir181b-2, I127ra, Stat1, C030018K13Rik, Foxq1, Hpcal1, Msra, Zc3hav1, Tdrd6, Tnfrsf4, 4921517D22Rik, Rubie, Plekhg6, Brd4, Sort1, U90926, 4930519F09Rik, I14ra, Smyd2, Prkch, March9, Ghsr, Rps6ka2, Rpp21, Vps13c, 1600002D24Rik, Fam136a, 4921511I17Rik, Spef1, Mam13, St8sia1, Ssbp2, Stk4, Tnfrsf19, Snord104, O1fr1507, Dysf, Cntn5, Cd2, Raver2, Gm10790, Pja1, Tmprss9, Klf5, Ubash3b, Tle3, Scm14, Snx4, Tert, Sptbn1, Mir326, Aff1, Gm8298, Ephb2, Tec, F3, Exoc6, Sema4f, Denndla, Gmcl1, Gm10532, St3gal1, Chd7, Gm6268, Tox, Pja2, K1h13, Dnajc10, Foxp1, Trp53inp1, Gtf3c3, Scd2, At12, Dach2, Lynx1, Cand1, Cxcr4, Gm20098, Fscn3, Il9r, Dph5, Sh3bp5, St6gal1, Fli1, Mir5127, Ubac1, Gm16793, Nsmaf, Sp6, Rnf145, Ccr7, Orai1, Serbp1, St6galnac5, Tox, Cacna1b, A430035B10Rik, Alp1, H2-DMb2, Etnk1, O1fr1507, Mtr, Rgmb, Pmp22, Dctn6, Fli1, Mir326, Slc17a7, Sepp1, Slc6a19, Cngb1, Mir7681, Ccr9, Klh14, Atp6v1g3, Clecl6a, Speer2, Gsn, Umps, Unc5c1, Aox2, Dcaf8, Igf2bp3, Car2, Rnf43, Kdm7a, Tgfbr3, Eldr, BC094916, Unc80, Zmyndl1, Nabp1, Adamts14, Gm20139, Fgfr1, Tmem141, C130026L21Rik, D630039A03Rik, Mtum, Herc3, Gm5468, Mir6398, Fam86, Nsg2, Cb1b, Erbb4, Mir?-2, Smurf1, Clecl6a, Lhx2, Tomm20, Ifngr2, Acacb, Gm10791, Bach1, Epb4.112, Tmem154, Tssc1, Vdac1, Itgae, Raph1, Klf3, Pnrc1, Sell, Tdrp, Ptk2, A630072M18Rik, Slc41a3, Rab11b, Tnfrsf10b, Lrp12, Ptger3, Aggf1, 1700029F12Rik, Dpf1, Gm14295, Ubqln2, Coq2, Txndc8, P2ry1, 4933430H16Rik, Tctex1d1, Sfmbt2, Alg14, Tha1, Ets1, Cd101, Neu3, Mob3b, Kcna2, Irs2, Mbnl1, Fntb, Nipb1, Slc16a5, Ccdc174, Ncs1, BC037032, Fry1, Lipa, Hslbp3, Cd101, Chd1, Atad1, Ppplr3fos, Pde4b, Lamtor3, Klf2, Ttc27, Dntt, 5830454E08Rik, Panx1, Cyp2r1, Rhou, Mir701, Ccr7, Arhgap26, Ankrd36, Retn1b, Themis, Med131, Slc6a19os, Znrf2, Mett18, Mir3108, D030025E07Rik, Mir145b, Iqsec1, Cd8b1, Clic1, 1810026B05Rik, Ptprs, Med7, Mthfd1l, Dnali1, Bach1, Mgmt, Ppm1b, 4933430H16Rik, Cd401g, Txk, Cdc14a, Il9r, Slc7a15, Prkch, Srpk2, Tmbim7, Rcor1, Vti1a, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511I17Rik, Dlx1, Lhx2, and/or Chst15. A novel approach was used that combined cross-species identification of $T_{EX}$ specific transcriptional and epigenetic changes. Genes were identified that are specifically up-regulated in $T_{EX}$ compared to canonical T cell populations (naïve, effector, memory T cells) in the lymphocytic choriomeningitis virus (LCMV) model in mice. Among this set of genes the subset that had unique $T_{EX}$ specific epigenetic changes in open chromatin regions was further selected based on ATAC-seq analyses (Pauken et al. Science 2016, 354(6316): 1160-1165). This signature outperforms previous exhaustion signatures because the epigenetically selected genes drive the enrichment with other datasets typically accumulating at the leading edge of signature enrichment.

Disease

T cell exhaustion, usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, these immune responses are rarely durable in patients. In some embodiments, the patient has a disease and is treated with an engineered T cell of the disclosure. In some embodiments, the disease is cancer. In some embodiments, the disease is an infectious disease.

In some embodiments, the disease is selected from the group consisting of cancer, viral infection, bacterial infection, and parasite infection. In further embodiments, the viral infection is with a virus selected from the group consisting of hepatitis viruses, herpesviruses, polyoma viruses, anelloviruses, adenoviruses, retroviruses, and influenza viruses. In some embodiments, the disease is a bacterial infection selected from the group consisting of *Mycobacterium tuberculosis* (MIB), *Staphylococcus aureus, Streptococcus pyogenes, Clostridium botulinum, Campylobacter jejuni, Escherichia coli, Listeria monocytogenes, Salmonella enterica, Salmonella bongori*, and *Vibrio cholera*. In some embodiments, the cancer is responsive to treatment with an immune checkpoint inhibitor. In further embodiments, the cancer responsive to treatment with immune checkpoint inhibitors is selected from the group consisting of unresectable melanoma, metastatic melanoma, Stage III melanoma, metastatic non-small cell lung cancer (NSCLC), NSCLC, recurrent squamous cell cancer of the head and neck (SCCHN), metastatic renal cell carcinoma (RCC), urothelial carcinoma, hepatocellular carcinoma (HCC), bladder cancer, colorectal cancer, ovarian cancer, and endothelial cancer. In some embodiments, any disease where a genomic signature of exhaustion is detected may be treated.

Treatments

Provided is an improved cell therapy composition comprising engineered T cells made by any one of the processes described herein. Also provided is a method of treating a disease characterized by increased numbers of exhausted CD8+ effector T cells ($T_{EX}$), comprising administering the improved cell therapy composition.

In some embodiments, the patient is administered an engineered T cell of the disclosure wherein the T cell has been engineered to prevent or reverse exhaustion of the T cell. In some embodiments, the T cell has been engineered by targeting a high priority epigenetic pathway in the T cell, as described herein. In some embodiments, administering the engineered T cell increases an immunological response in the patient. In some embodiments, the patient having a disease is treated for the disease with one or more immune checkpoint inhibitors before being administered the engineered T cell. In some embodiments, the patient is treated with one or more immune checkpoint inhibitors before administering the engineered T cell. In some embodiments, the engineered T cell is administered simultaneously or concurrently with an immune checkpoint inhibitor.

T Cells

During acute infections or vaccinations, naive T cells are activated and differentiate into effector T cells over the course of 1-2 weeks. This differentiation is accompanied by robust proliferation, transcriptional, epigenetic and metabolic reprogramming, and the acquisition of cardinal features of effector T cells such as effector function, altered tissue homing and dramatic numerical expansion. Following the peak of effector expansion, the resolution of inflammation and the clearance of antigen, most activated T cells die, but a subset persists and transitions into the memory T cell pool. These memory T cells downregulate much of the activation program of effector T cells, yet they maintain the ability to rapidly reactivate effector functions upon restimulation. In addition, memory T cells develop a key memory property of antigen-independent self-renewal, which is a type of stem cell-like, slow division that is driven by interleukin-7 (IL-7) and IL-15. There is considerable diversity and complexity of memory T cell subsets and differentiation following acute infections or vaccinations (for example, effector memory T cells versus central memory T cells). However, a key aspect of the development of functional, persisting memory T cells is that after the effector phase, memory development occurs in the absence of ongoing antigen stimulation and high levels of persisting inflammation (Wherry and Kurachi. Nat Rev Immunol. 2015, 15(8):486-499).

By contrast, during chronic infections and cancer—which involve persistent antigen exposure and/or inflammation—this program of memory T cell differentiation is markedly altered. An altered differentiation state, termed T cell exhaustion, usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, a durable clinical response often does not occur because of failure to fully reinvigorate $T_{EX}$.

Exhausted T Cells

Exhausted T cells are not inert. They retain suboptimal but crucial functions that limit ongoing pathogen replication or tumor progression. Despite this host-pathogen stalemate mediated by exhausted T cells, these cells are not effective in eradicating pathogens or tumors, and there has been considerable interest in avoiding or reversing exhaustion. The demonstration that T cell exhaustion is reversible (at least at the population level) rather than a terminal or irreversible fate provides a substantial clinical opportunity to use immunotherapy to improve immunity. Although the immunological effects of these human treatments remain to be fully defined, emerging results support the notion that reversal of T cell exhaustion in humans is a causative mechanism for the marked antitumour effect that is seen in many patients receiving agents that block the PD1 pathway.

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8 T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) *Immunol.* 129:474-481; Wherry and Ahmed (2004) *J Virol.* 78:5535-5545). In the first stage, functional T cells enter a "partial exhaustion I" phase characterized by the loss of a subset of effector functions, including loss of IL-2 production, reduced TNFa production, and reduced capacity for proliferation and/or ex vivo lysis ability. In the second stage, partially exhausted T cells enter a "partial exhaustion II" phase when both IL-2 and TNFα production ceases following antigenic stimulation and IFNγ production is reduced. "Full exhaustion" or "terminal exhaustion" occurs when CD8+ T cells lose all effector functions, including the lack of production of IL-2, TNFα, and IFNγ and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFα, or IFNγ, in response to normal input signals. Such lack of effector functions can occur when the antigen load is high and/or CD4 help is low. This hierarchical loss of function is also associated with the expression of co-inhibitor immune receptors, such as PD-1, TIM-3, LAG-3, and the like (Day et al. (2006) *Nature* 443:350-4; Trautmann et al. (2006) *Nat. Med.* 12:1198-202; and Urbani et al. (2006) *J Virol.* 80:1398-1403). Other molecular markers distinguish the hierarchical stages of immune cell exhaustion, such as high eomesodermin (EOMES) and low TBET expression as a marker of terminally exhausted T cells (Paley et al. (2012) *Science* 338:1220-1225). Additional markers of exhausted T cells, such as the reduction of Bcl-b and the increased production of BLIMP-1 (Pdrm1).

The protective capacity of the adaptive immune system relies on efficient and coordinated transitions between cellular fates. Following initial activation by specific antigen, naive $CD8^+$ T cells proliferate extensively and undergo a highly orchestrated program of molecular rewiring and differentiation into effector $CD8^+$ T cells ($T_{EFF}$) that can mediate protection through cytotoxicity and production of inflammatory cytokines (Kaech, S. M. & Wherry, E. J. Heterogeneity and cell-fate decisions in effector and memory CD8+ T cell differentiation during viral infection. *Immunity* 27, 393-405 (2007); Chang, J. T., Wherry, E. J. & Goldrath, A. W. Molecular regulation of effector and memory T cell differentiation. *Nat Immunol* 15, 1104-1115 (2014); Kaech, S. M. & Cui, W. Transcriptional control of effector and memory CD8+ T cell differentiation. 12, 749-761 (2012); Cui, W. & Kaech, S. M. Generation of effector CD8+ T cells and their conversion to memory T cells. *Immunol Rev* 236, 151-166 (2010)). If the infection or antigen is cleared, most of this $T_{EFF}$ pool dies, but a subset persists, undergoing additional differentiation to form a pool of long-lived, self-renewing memory T cells ($T_{MEM}$) capable of mounting rapid recall responses. In contrast, during chronic infections or cancer, when T cell stimulation persists, this program of functional T cell differentiation is diverted and T cells fail to sustain robust effector functions, instead becoming exhausted (Wherry, E. J. & Kurachi, M. Molecular and cellular insights into T cell exhaustion. *Nature Publishing Group* 15, 486-499 (2015); Wherry, E. J. T cell exhaustion. *Nat Immunol* 12, 492-499 (2011)). Exhausted CD8+ T cells ($T_{EX}$) may balance limited pathogen or tumor control while restraining damaging immunopathology, but the consequence of restrained functionality is disease persistence and possible progression (Barber, D. L. et al. Restoring function in exhausted CD8 T cells during chronic 1155 viral infection. *Nature* 439, 682-687 (2005); Frebel, H. et al. Programmed death 1 protects from fatal circulatory failure during systemic virus infection of mice. *J Exp Med* 209, 2485-2499 (2012)). Though first described in mice infected with lymphocytic choriomeningitis virus (LCMV), it is now clear that T cell exhaustion is a common feature of many chronic infections as well as a variety of cancers in both mice and humans (Zajac, A. J. et al. Viral Immune Evasion Due to Persistence of Activated T Cells Without Effector Function. *J Exp Med* 188, 2205-2213 (1998); Gallimore, A. et al. Induction and Exhaustion of Lymphocytic Choriomeningitis Virus-specific Cytotoxic T Lymphocytes Visualized Using Soluble Tetrameric Major Histocompatibility Complex Class I—Peptide Complexes. *J Exp Med* 187, 1383-1393 (1998); Lechner, F. et al. Analysis of Successful Immune Responses in Persons Infected with Hepatitis C Virus. *J Exp Med* 191, 1499-1512 (2000). 1166 12. Shankar, P. et al. Impaired function of circulating HIV-specific CD8(+) T cells in chronic human immunodeficiency virus infection. *Blood* 96, 3094-3101 (2000)). Indeed, $T_{EX}$ are highly therapeutically relevant since these cells are a major target of checkpoint blockade mediated immune re-invigoration in human cancer patients (Pauken, K. E. & Wherry, E. J. Overcoming T cell exhaustion in infection and cancer. *Trends in Immunology* 36, 265-276 (2015); Page, D. B., Postow, M. A., Callahan, M. K., Allison, J. P. & Wolchok, J. D.; Immune Modulation in Cancer with Antibodies. Annu. Rev. Med. 65, 185-202 (2014); Hamid, O. et al. Safety and Tumor Responses with Lambrolizumab (Anti-PD-1) in Melanoma. *N Engl J Med* 369, 134-144 (2013); Hirano, F. et al. Blockade of B7-H1 and PD-1 by monoclonal antibodies potentiates cancer therapeutic immunity. *Cancer Res.* 65, 1089-1096 (2005); Barber, D. L. et al. Restoring function in exhausted CD8 T cells during chronic viral infection. *Nature* 439, 682-687 (2005)).

T cell exhaustion is characterized by the progressive decline in effector function including the hierarchical loss of inflammatory cytokine production (IL-2, TNFα, IFNγ) (Wherry, E. J., Blattman, J. N., Murali-Krishna, K., van der Most, R. & Ahmed, R. Viral Persistence Alters CD8 T-Cell Immunodominance and Tissue Distribution and Results in Distinct Stages of Functional Impairment. *J Virol* 77, 4911-4927 (2003); Fuller, M. J. & Zajac, A. J. Ablation of CD8 and CD4 T Cell Responses by High Viral Loads. *J Immunol* 170, 477-486 (2003)). $T_{EX}$ also sustain high co-expression of multiple inhibitory receptors (PD-1, LAG3, TIGIT, CD160, TIM-3, 2B4) (Blackburn, S. D. et al. Coregulation of CD8+ T cell exhaustion by multiple inhibitory receptors during chronic viral infection. *Nat* 1186 *Immunol* 10, 29-37 (2008)), have reduced glycolytic and oxidative phosphorylation capacity (Bengsch, B. et al. Bioenergetic Insufficiencies Due to Metabolic Alterations Regulated by the Inhibitory Receptor PD-1 Are an Early Driver of CD8+ T Cell Exhaustion. *Immunity* 45, 358-373 (2016); Staron, M. M. et al. The Transcription Factor FoxO1 Sustains Expression of the Inhibitory Receptor PD-1 and Survival of Antiviral CD8+ T Cells during Chronic Infection. *Immunity* 41, 802-814 (2014)), and impaired proliferation and survival (Wherry, E. J., Blattman, J. N. & Ahmed, R. Low CD8 T-Cell Proliferative Potential and High Viral Load Limit the Effectiveness of Therapeutic Vaccination. *J Virol* 79, 8960-8968 (2005); Wherry, E. J., Barber, D. L., Kaech, S. M., Blattman, J. N. & Ahmed, R. Antigen independent memory CD8 T cells do not develop during chronic viral infection. *Proc Natl Acad Sci USA* 101, 16004-16009 (2004); Shin, H., Blackburn, S. D., Blattman, J. N. & Wherry, E. J. Viral antigen and extensive division maintain virus-specific CD8 T cells during chronic infection. *J* 1201 Exp Med 204, 941-949 (2007)). Underlying these major differences in $T_{EX}$ compared to $T_{EFF}$ and $T_{MEM}$, is a distinct transcriptional program highlighted by altered use of key transcription factors and altered transcriptional circuits (Wherry, E. J. et al. Molecular signature of CD8+ T cell exhaustion during chronic viral infection. *Immunity* 27, 670-684 (2007); Doering, T. A. et al. Network Analysis Reveals Centrally Connected Genes and Pathways Involved in CD8+ T Cell Exhaustion versus Memory. *Immunity* 37, 1130-1144 (2012); Crawford, A. et al. Molecular and Transcriptional Basis of CD4+ T Cell Dysfunction during Chronic Infection. *Immunity* 40, 289-302 (2014)). Indeed, unique networks of transcription factors (TFs) regulate different functional modules of exhaustion. T cell receptor signaling integrators including the NFAT proteins, BATF, and IRF4 have been shown to be involved in the induction of exhaustion (Grusdat, M. et al. IRF4 and BATF are critical for CD8+ T-cell function following infection with LCMV. *Cell Death and Differentiation* 21, 1050-1060 (2014); Man, K. et al. Transcription Factor IRF4 Promotes CD8+ T Cell Exhaustion and Limits the Development of Memory-like T Cells during Chronic Infection. *Immunity* 47, 1129-1141.e5 (2017); Martinez, G. J. et al. The Transcription Factor NFAT Promotes Exhaustion of Activated CD8+ T Cells. *Immunity* 42, 265-278 (2015)) whereas T-bet, Eomesodermin (Eomes), and Tcfl are involved in coordinating a proliferative hierarchy to maintain the $T_{EX}$ population once established (Im, S. J. et al. Defining CD8+ T cells that provide the proliferative burst after PD-1 therapy. *Nature* 537, 417-421 (2016); Wu, T. et al. The TCF1-Bc16 axis counteracts type I interferon to repress exhaustion and maintain T cell stemness. *Sci Immunol* 1, eaai8593-eaai8593 (2016); Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012)). In addition, Blimp-1, Bc16, and Foxol regulate the locomotive and metabolic capabilities of $T_{EX}$ cells as well as the overall severity of dysfunction. In some cases, these TFs are also employed by $T_{EFF}$ or $T_{MEM}$, but with different functions and altered transcriptional connections, implying an epigenetic environment allowing the same TF to perform divergent activities. Despite this work, it has been unclear whether $T_{EX}$ are simply dysregulated $T_{EFF}$, arrested $T_{MEM}$, or whether $T_{EX}$ are a distinct cell fate. Recent epigenetic analysis, however, revealed that $T_{EX}$ differ from $T_{EFF}$ and $T_{MEM}$ by 6000 open chromatin regions, similar to differences between other major hematopoietic lineages suggesting that $T_{EX}$ are not simply a state of activation of $T_{EFF}$ or $T_{MEM}$, but rather are a distinct immune lineage (Im, S. J. et al. Defining CD8+ T cells that provide the proliferative burst after PD-1 therapy. *Nature* 537, 417-421 (2016); Wu, T. et al. The TCF1-Bc16 axis counteracts type I interferon to repress exhaustion and maintain T cell stemness. *Sci Immunol* 1, eaai8593-eaai8593 (2016); Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012)). The mechanisms that initiate this $T_{EX}$ fate commitment and epigenetic and transcriptional programming have thus far remained poorly understood, and exhaustion-specific TFs or transcriptional programming activities have remained elusive.

Here, a requisite role for the HMG-box TF TOX in programming the early epigenetic events that drive fate commitment to the $T_{EX}$ lineage is defined. Without wishing to be bound by theory, TOX integrates early, sustained NFAT2 activity into a subsequent NFATindependent TOX-driven molecular and epigenetic $T_{EX}$ program. TOX is necessary and sufficient to induce major cellular features of $T_{EX}$ including inhibitory receptor expression, decreased function and the pattern of downstream TF expression necessary for $T_{EX}$ population maintenance. TOX is transiently and lowly expressed during many acute infections and $T_{EFF}$ and $T_{MEM}$ can form without TOX. In contrast, TOX expression is robust and sustained in $T_{EX}$ and the development of $T_{EX}$ is completely dependent on this TF. TOX interacts with major histone modifying enzyme complexes and is capable of initiating key $T_{EX}$-specific epigenetic changes to function as the $T_{EX}$ lineage initiator. Thus, these data identify TOX as a critical $T_{EX}$ lineage programming transcriptional and epigenetic coordinator. These results have implications for the ontogeny of $T_{EX}$ and suggest potential therapeutics based on targeting TOX and TOX regulated epigenetic events.

Inhibitory Receptors and Treatment with Immune Checkpoint Blockade

Inhibitory receptors are crucial negative regulatory pathways that control autoreactivity and immunopathology. Although inhibitory receptors are transiently expressed in functional effector T cells during activation, higher and sustained expression of inhibitory receptors is a hallmark of exhausted T cells. The inhibitory signaling pathway mediated by PD1 in response to binding of PD1 ligand 1 (PDL1) and/or PDL2 offers an illustrative example. Whereas our understanding of the molecular mechanisms by which the inhibitory receptor PD1 controls T cell exhaustion remains incomplete, and without wishing to be bound by any theory, there are several mechanisms by which inhibitory receptors such as PD1 might regulate T cell function: first, by ectodomain competition, which refers to inhibitory receptors sequestering target receptors or ligands and/or preventing the optimal formation of microclusters and lipid rafts (for example, CTLA4); second, through modulation of intracellular mediators, which can cause local and transient intracellular attenuation of positive signals from activating receptors such as the TCR and co-stimulatory receptors; and third, through the induction of inhibitory genes.

Whereas there is some knowledge about PD1, understanding of the intracellular mechanisms of action of inhibitory receptors—including those of PD1—is incomplete. The intracellular domain of PD1 contains an immunoreceptor tyrosine-based inhibitory motif (ITIM) and an immunoreceptor tyrosine-based switch motif (ITSM). In vitro studies suggest a role for the ITSM in recruiting the tyrosine-protein phosphatase SHP1 (also known as PTPN6) and/or SHP2 (also known as PTPN11). The role of the ITIM in PD1 function remains poorly understood. Other evidence implicates a role for PD1 signaling in modulating the phosphoinositide 3-kinase (PI3K), AKT and RAS pathways, and also links PD1 to cell cycle control. Notably, much of our information about how PD1 controls T cell signaling is derived from in vitro studies of acutely activated T cells. In vivo studies of the role of PD1 during acute T cell activation and expansion suggest a possible role for PD1 signaling in either increasing mobility paralysis or decreasing migratory arrest, depending on the context. Finally, signaling downstream of PD1 may in fact induce the expression of genes that could negatively regulate the expression of effector genes, such as BATF, which encodes the activator protein 1 (AP-1) family member basic leucine zipper transcription factor ATF-like. Despite this elegant work, it is unclear how these observations relate to exhausted T cells exposed to chronic infection in vivo.

PD1 expression is rapidly upregulated upon T cell activation, and it may persist at moderate levels in healthy humans, indicating that PD1 expression alone is not a unique feature of exhausted T cells. However, during chronic infections PD1 expression can be substantially higher than observed on functional effector or memory CD8+ T cells. During chronic infection, sustained upregulation of PD1 is usually dependent on continued epitope recognition, although examples exist of residual PD1 expression even after removal of persisting antigen signaling.

In addition to PD1, exhausted T cells express a range of other cell surface inhibitory molecules. Exhausted T cells can co-express PD1 together with lymphocyte activation gene 3 protein (LAG3), 2B4 (also known as CD244), CD160, T cell immunoglobulin domain and mucin domain-containing protein 3 (TIM3; also known as HAVCR2), CTLA4 and many other inhibitory receptors. Typically, the higher the number of inhibitory receptors co-expressed by exhausted T cells, the more severe the exhaustion. Indeed, although individual expression of PD1 or other inhibitory receptors is not indicative of exhaustion, co-expression of multiple inhibitory receptors is a cardinal feature. These co-expression patterns are mechanistically relevant, as simultaneous blockade of multiple inhibitory receptors results in synergistic reversal of T cell exhaustion. This concept was demonstrated for PD1 and LAG3 in chronic LCMV infection, and for PD1 and CTLA4 in HIV infection, other infections and cancer. Many other combinations of inhibitory receptors such as PD1 and TIM3 can also co-regulate exhausted T cells. PD1 and CTLA4 blockade in patients with melanoma demonstrated impressive tumor control, and clinical trials of other combinations of agents blocking inhibitory receptors are underway (for example, ClinicalTrials.gov identifiers NCT01968109, NCT02210117 and NCT02408861, which are among >120 other trials involving the PD1 pathway). Overall, these data on the role of inhibitory receptors in co-regulation of T cell exhaustion suggest that these pathways are non-redundant. These molecules come from diverse structural families, bind ligands with distinct expression patterns and have distinct intracellular signaling domains. Thus, there is the potential to tailor or tune the type and magnitude of exhausted T cell reinvigoration.

In addition to inhibitory receptors, it has become clear that co-stimulatory receptors are involved in T cell exhaustion. For example, desensitization of co-stimulatory pathway signaling through the loss of adaptor molecules can serve as a mechanism of T cell dysfunction during chronic infection. The signaling adaptor tumor necrosis factor receptor (TNFR)-associated factor 1 (TRAF1) is downregulated in dysfunctional T cells in HIV progressors, as well as in chronic LCMV infection. Adoptive transfer of CD8+ T cells expressing TRAF1 enhanced control of chronic LCMV infection compared with transfer of TRAF1-deficient CD8+ T cells, which indicates a crucial role for TRAF1-dependent co-stimulatory pathways in this setting. It has also been possible to exploit the potential beneficial role of co-stimulation to reverse exhaustion by combining agonistic antibodies to positive co-stimulatory pathways with blockade of inhibitory pathways. 4-1BB (also known as CD137 and TNFRSF9) is a TNFR family member and positive co-stimulatory molecule that is expressed on activated T cells. Combining PD1 blockade and treatment with an agonistic antibody to 4-1BB dramatically improved exhausted T cell function and viral control. Although a simple model of positive versus negative co-stimulation during T cell exhaustion probably has mechanistic validity, the diversity of pathways and much of the experimental data suggest that specific qualitative signals may be imparted by distinct co-stimulatory and co-inhibitory pathways (Wherry and Kurachi. Nat Rev Immunol. 2015, 15(8):486-499).

In some embodiments, an inhibitory receptor is targeted in the patient. In some embodiments, the inhibitory receptor is targeted with an immune checkpoint inhibitor. The immune checkpoint inhibitor, without limitation, can be PD-1, PD-L1, CTLA-4, TIM3, B7-H3, BTLA, VISTA, CD40, CEACAM1/CD66a, CD80/B7-1, CD86/B7-2, OX40/CD134, CD40 Ligand, ICOS Ligand/B7-H2, 4-1BBL/CD137L, or B7-DC/PD-L2/CD273. In some embodiments, the immune checkpoint inhibitor is targeted with an anti-immune checkpoint inhibitor antibody. In some embodiments, the patient is simultaneously or concurrently treated with an anti-immune checkpoint inhibitor and an engineered T cell of the disclosure. In some embodiments, the patient is treated with an engineered T cell of the disclosure after the patient has been treated with an anti-immune checkpoint inhibitor, e.g., 1 minute, 5 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days after treatment with an immune checkpoint inhibitor.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out some embodiments of the present invention, and are not to be construed as limiting in any way the remainder of the disclosure.

Naïve Lymphocyte Isolation and Adoptive T Cell Transfer

T cell receptor transgenic GP specific $CD8^+$ T cells (P14) were isolated from the peripheral blood of donor mice using gradient centrifugation with the density gradient cell separation medium Histopaque™-1083 (Sigma Aldrich). For experiments using LCMV infection, WT P14 cells were mixed 1:1 with congenically disparate P14 cells of the desired genotype ($TOX^{+/-}$ P14) and a total of 500 naive cells were adoptively transferred by tail-vein injection into 6-8-week-old recipient mice 1-5 days prior to infection. Recipients were of a third congenic background to allow distinguishing of both donor populations from the host T cells. For experiments monitoring only WT P14 responses, 500 cells were transferred. Previous reports have shown that adoptive transfer of 500 P14 T cells prior to LCMV C1-13 or Arm infection does not impact viral load or pathogenesis (Frebel, H. et al. Programmed death 1 protects from fatal circulatory failure during systemic virus infection of mice. *J Exp Med* 209, 2485-2499 (2012); Odorizzi, P. M., Pauken, K. E., Paley, M. A., Sharpe, A. & Wherry, E. J. Genetic absence of PD-1 promotes accumulation of terminally differentiated exhausted CD8+ T cells. *J Exp Med* 212, 1125-1137 (2015); Blattman, J. N., Wherry, E. J., Ha, S. J., van der Most, R. G. & Ahmed, R. Impact of Epitope Escape on PD-1 Expression and CD8 T-Cell Exhaustion during Chronic Infection. *J Virol* 83, 4386-4394 (2009)).

Ectopic Tumor Model

B16-F10-GP33 melanoma cell line was cultured at 37° C. in DMEM medium supplemented with 10% FBS, 100U/ml penicillin, 100 U/ml streptomycin, and 2mM L-glutamine. $2\times10^5$ tumor cells were injected subcutaneously (s.c.) in flank of mice. Serial tumor area measurements following inoculation in flank with B16-F10-GP33 and transfer of pre-activated WT or $TOX^{+/-}$ P14 T cells.

ZC3H12C Gene and Enhancer Element Deletion and In Vivo Testing

Zc3h12c knockout)(Zc3h12c$^{KO}$ lacking exon 2 or Zc3h12c enhancer knockout (lacking a 372bp enhancer element located ~15 kp upstream of the transcriptional start site; Zc3h12c Enhancer$^{KO}$) mice were generated by CRISPR gene manipulation. These mice were crossed to LCMV-specific TCR transgenic P14 mice. Zc3h12c$^{KO}$ or Zc3h12c Enhancer$^{KO}$ P14 were mixed 50:50 with congenically different WT P14 cells and adoptively transferred into WT mice of a third congenic background. These mice were infected with LCMV Armstrong or clone 13 and responses of P14 cells of each genotype were analyzed in the blood at different time points.

Results of the experiments are now described.

Example 1. Partial Loss of TOX

Because complete TOX deficiency resulted in an inability to sustain $T_{EX}$ responses in chronic infection, the effect of partial loss of TOX was investigated.

To test whether partial loss of TOX had a therapeutic benefit, the B16 tumor system was used with tumor cells expressing the GP33-41 CD8 T cell epitope from lymphocytic choriomeningitis virus (LCMV). LCMV specific TCR transgenic CD8 T cells specific for GP33-41 presented by H-2Db ("P14" cells) were used on a WT or $TOX^{+/-}$ background. Thus, whether partial loss of TOX using conditional deletion of one allele would enhance tumor immunity was studied.

The results indicate that partially TOX-deficient tumor-specific T cells controlled tumor growth significantly better than WT cells after adoptive transfer into mice harboring B16 tumors expressing the GP33 epitope (FIG. 1). These data demonstrated that partial reduction in TOX through elimination of one copy of the gene had a therapeutic benefit and resulted in improved tumor control.

Example 2. Targeting of ZC3H12C and Enhancer Element

Figure 3A:
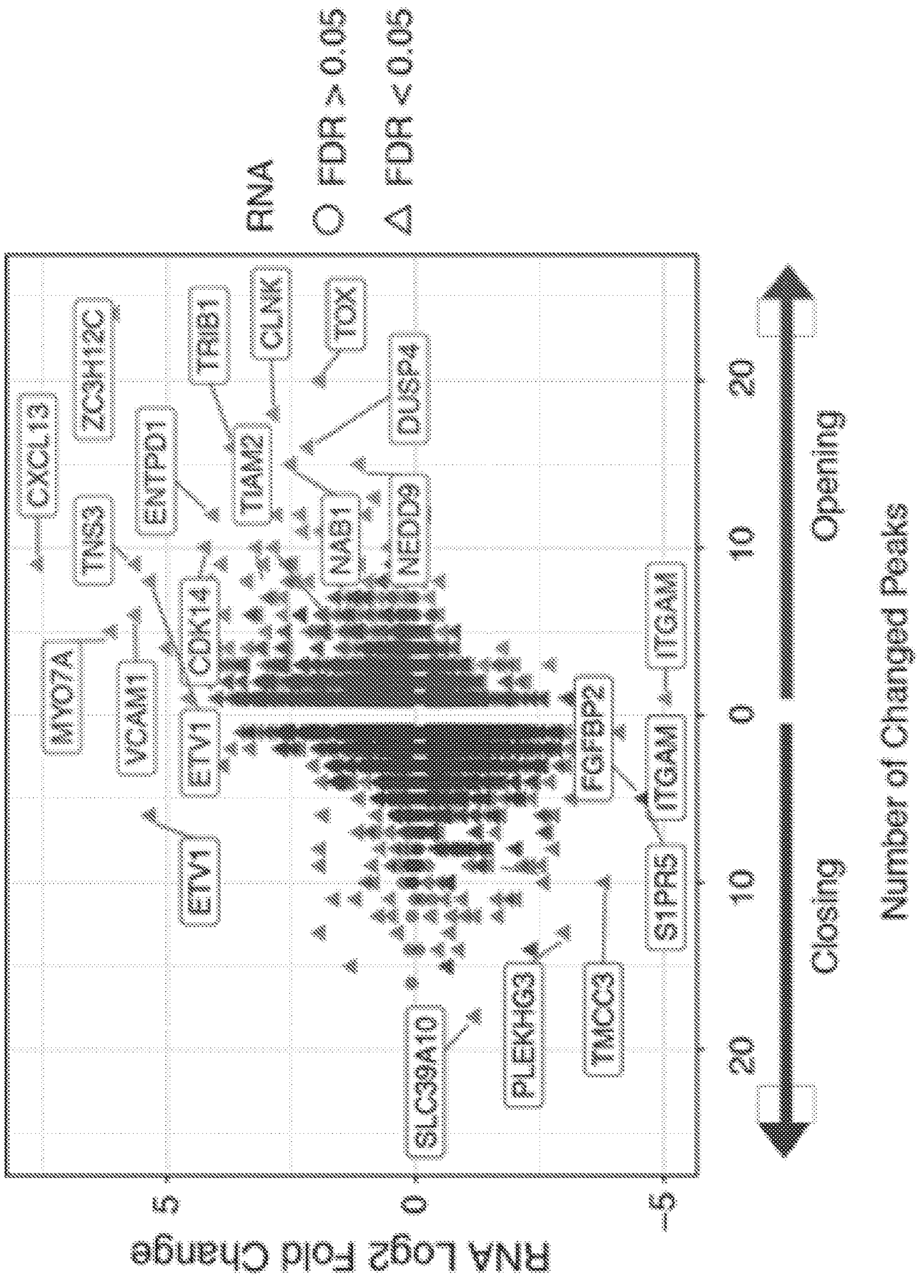
FIGS. 3A-3B illustrate the identification of ZC3H12C in an assessment of transcriptional and epigenetic data from human melanoma patients treated with anti-PD-1.
Figure 3B:
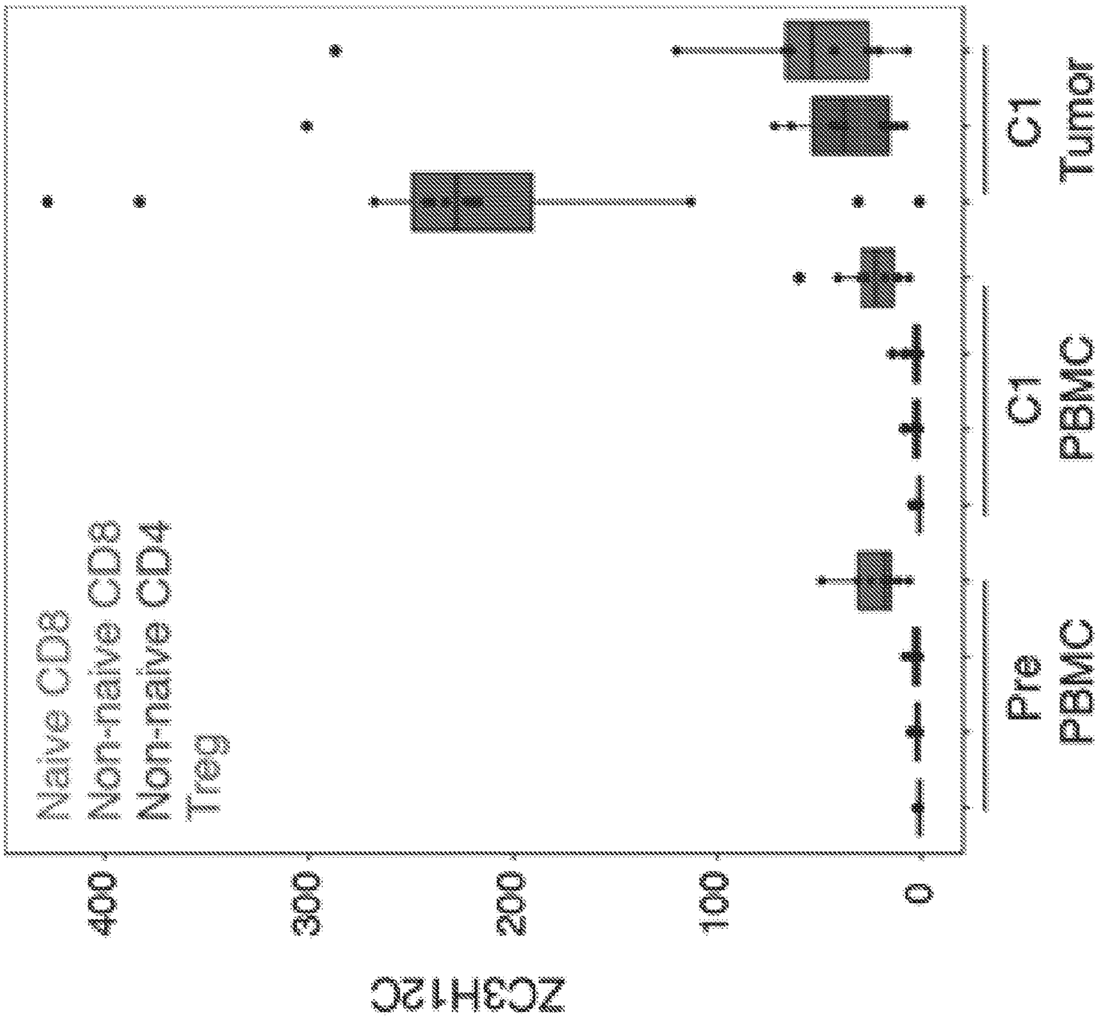

ZC3H12C was identified as a candidate exhaustion relevant gene in an assessment of transcriptional and epigenetic data from human melanoma patients treated with anti-PD-1 (FIG. 3B). ZC3H12C was highly upregulated in TIL compared to PBMC and the locus displayed substantially more OCR in CD8 T cells from TIL at 3 weeks of anti-PD-1 treatment (cycle 1; C1; FIG. 3B).

Figure 2A:
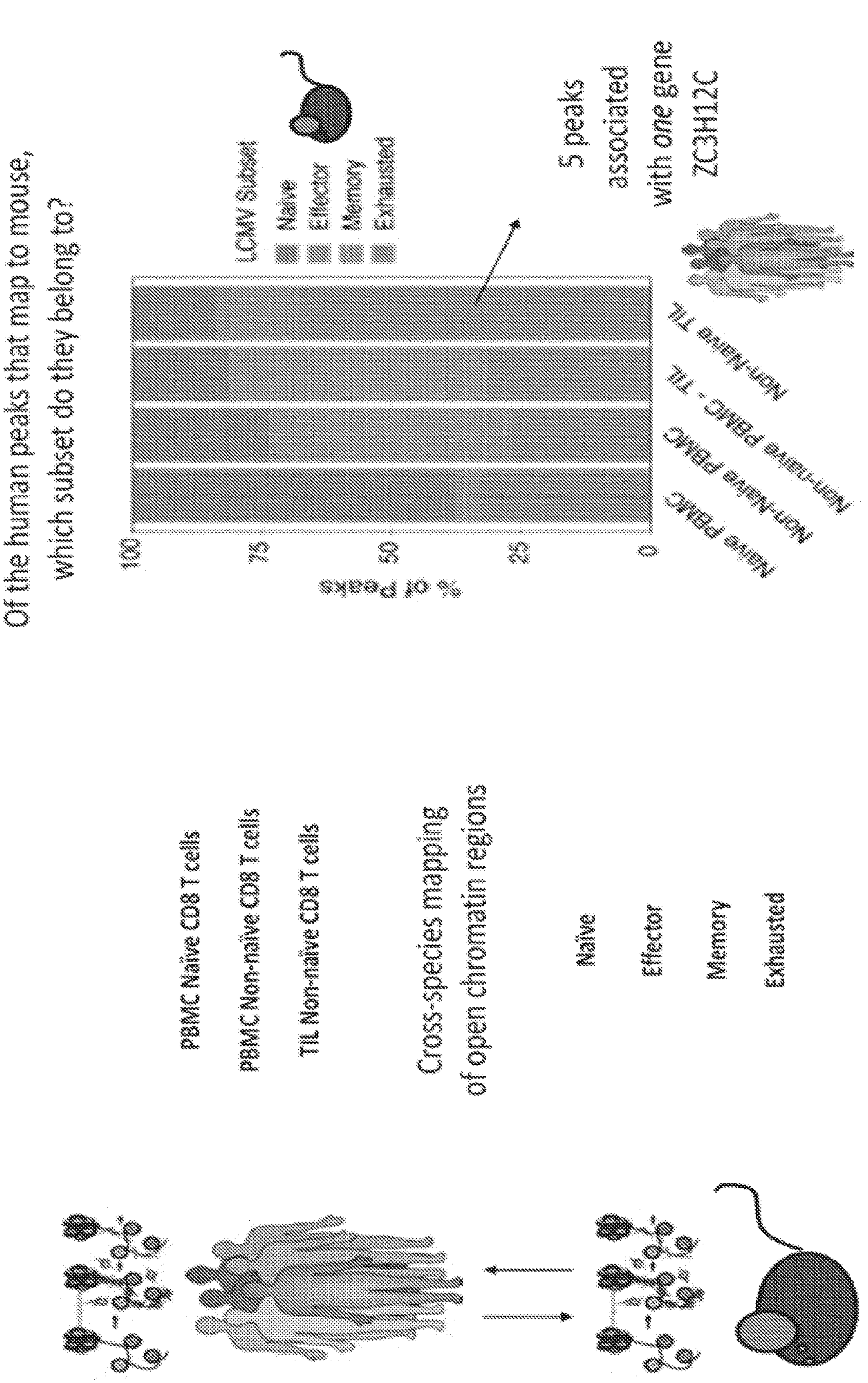
FIGS. 2A-2B illustrate the identification of open chromatin regions.
Figure 2B:
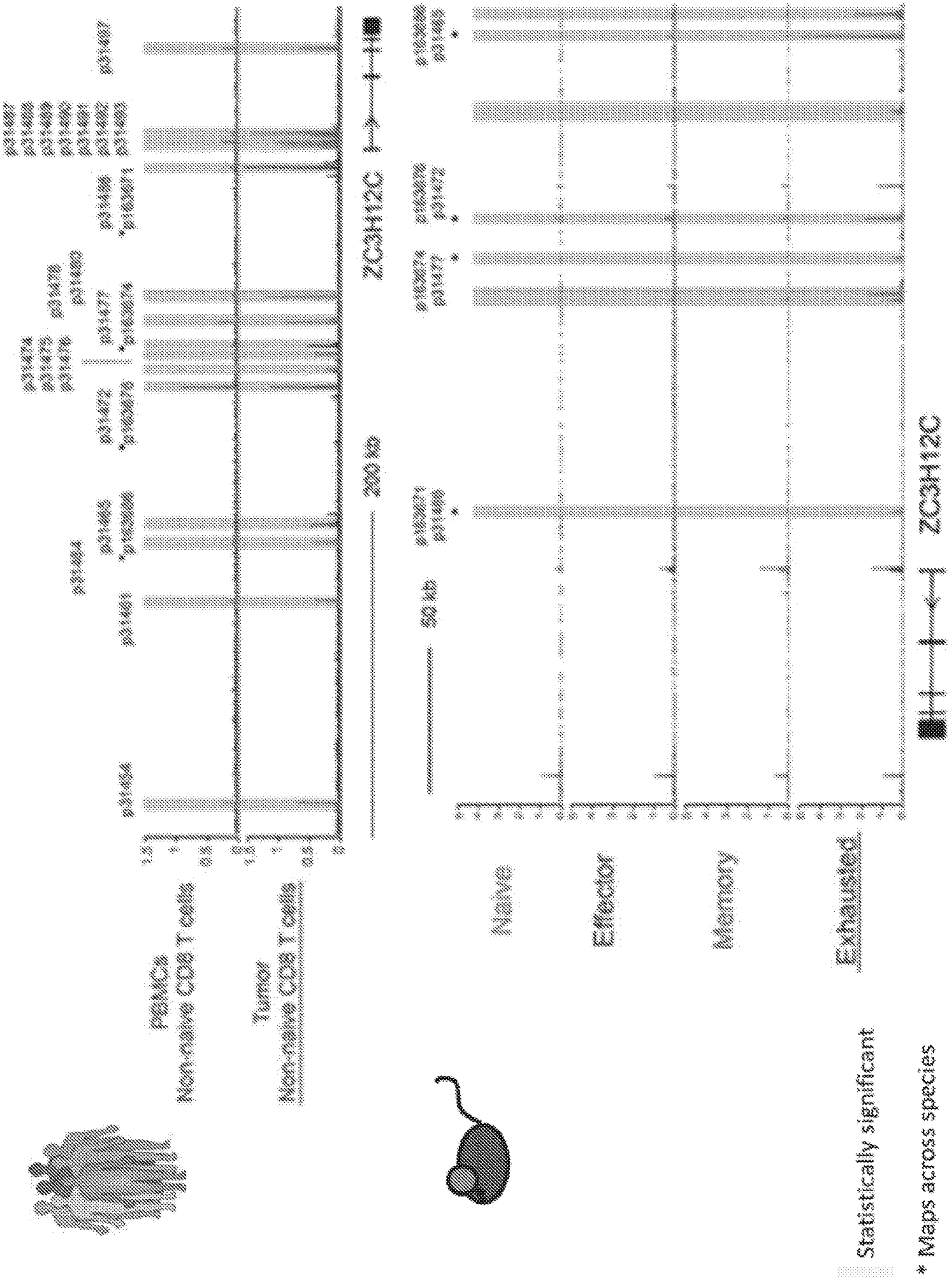
Figure 4:
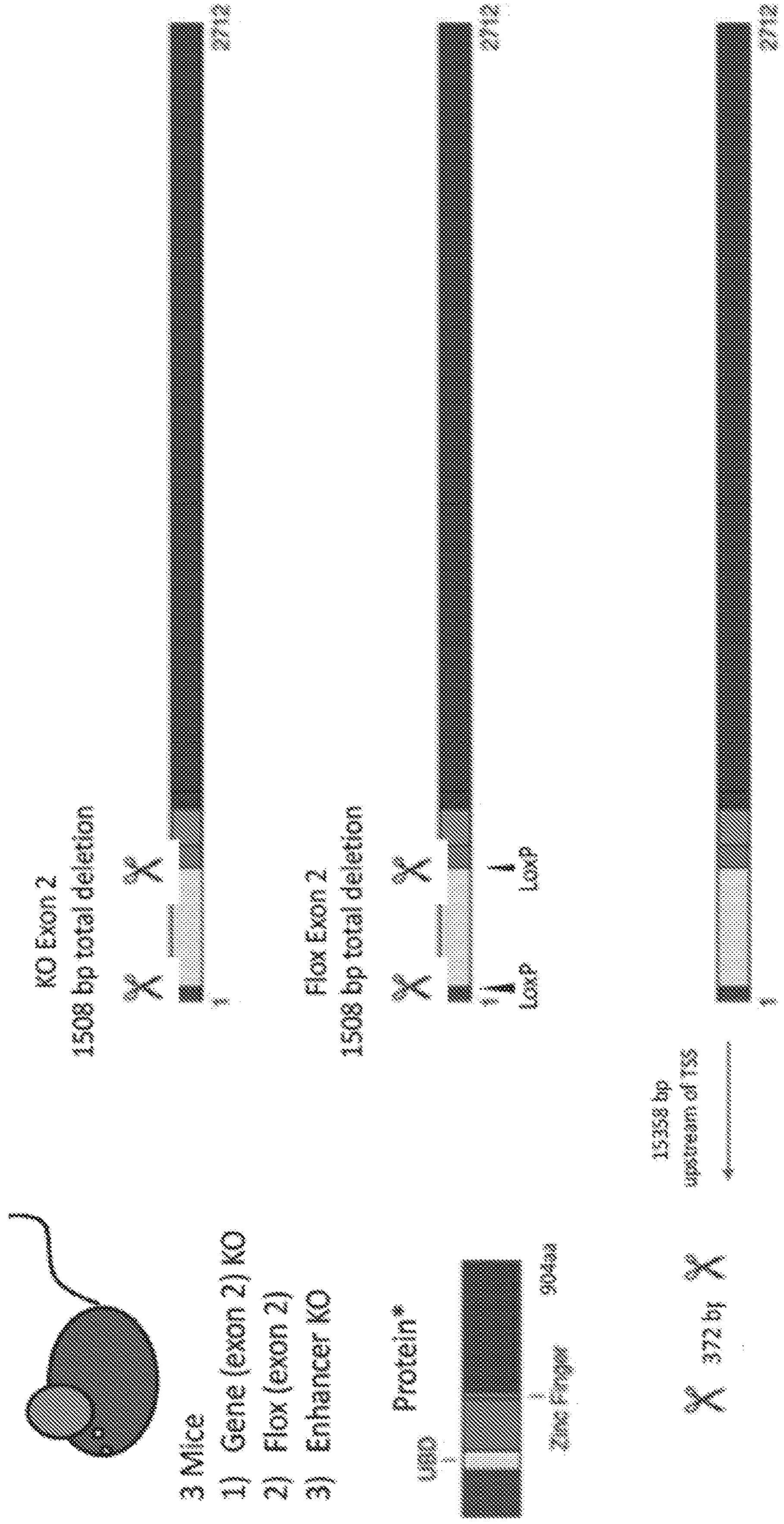
FIG. 4 is a schematic of Zc3h12c genetic mouse models generated including a strain in which exon 2 of Zc3h12c has been knocked out by CRISPR gene manipulation, a strain in which exon 2 of Zc3h12c has been knocked out using Cre/loxP recombination, and a strain in which a 372 base pair (bp) exhaustion-specific enhancer conserved between mice and humans located 15.3 kilobase pairs (kb) upstream of the Zc3h12c transcription start site (TSS) has been knocked out by CRISPR gene manipulation.

Non-coding cis regulatory enhancer locations or OCR were mapped across species. Several species conserved (and likely biologically important) OCR elements were identified (FIG. 2). Mice deleted in the coding sequence of Zc3h12c and a non-coding enhancer element ~15 kb upstream of the transcriptional start site were generated (FIG. 4).

Figure 5:
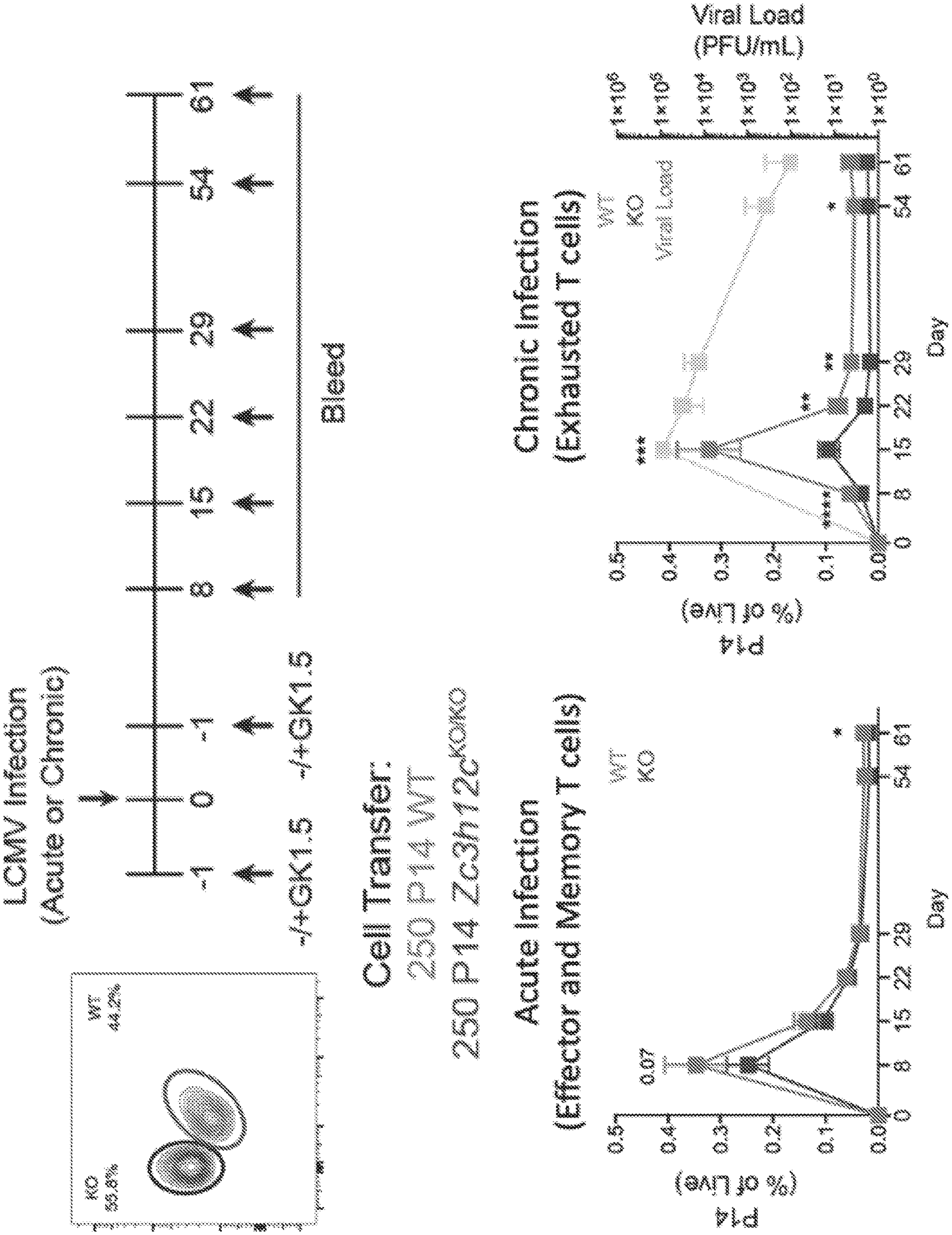
FIG. 5 illustrates in vivo testing of Zc3h12c exon 2 KO mice in the LCMV mouse model of T cell exhaustion. Top: 50:50 mixture of WT and KO cells injected into WT mice followed by either acute infection (to generate $T_{EFF}$ and $T_{MEM}$) or chronic infection (to generate $T_{EX}$). Bottom Left: no difference in $T_{EFF}$ or $T_{MEM}$ numbers in KO. Bottom Right: significant decrease in $T_{EX}$ numbers in the absence of Zc3h12c expression.

Zc3h12c exon 2 KO mice were generated (FIG. 5). A 50:50 mixture of WT and KO cells was injected into WT mice followed by either acute infection (to generate $T_{EFF}$ and $T_{MEM}$) or chronic infection (to generate $T_{EX}$). The results show that there was no difference in $T_{EFF}$ or $T_{MEM}$ in KO mice. However, there was a major defect in the generation of $T_{EX}$ in Zc3h12c exon 2 KO mice (FIG. 5).

Figure 6A:
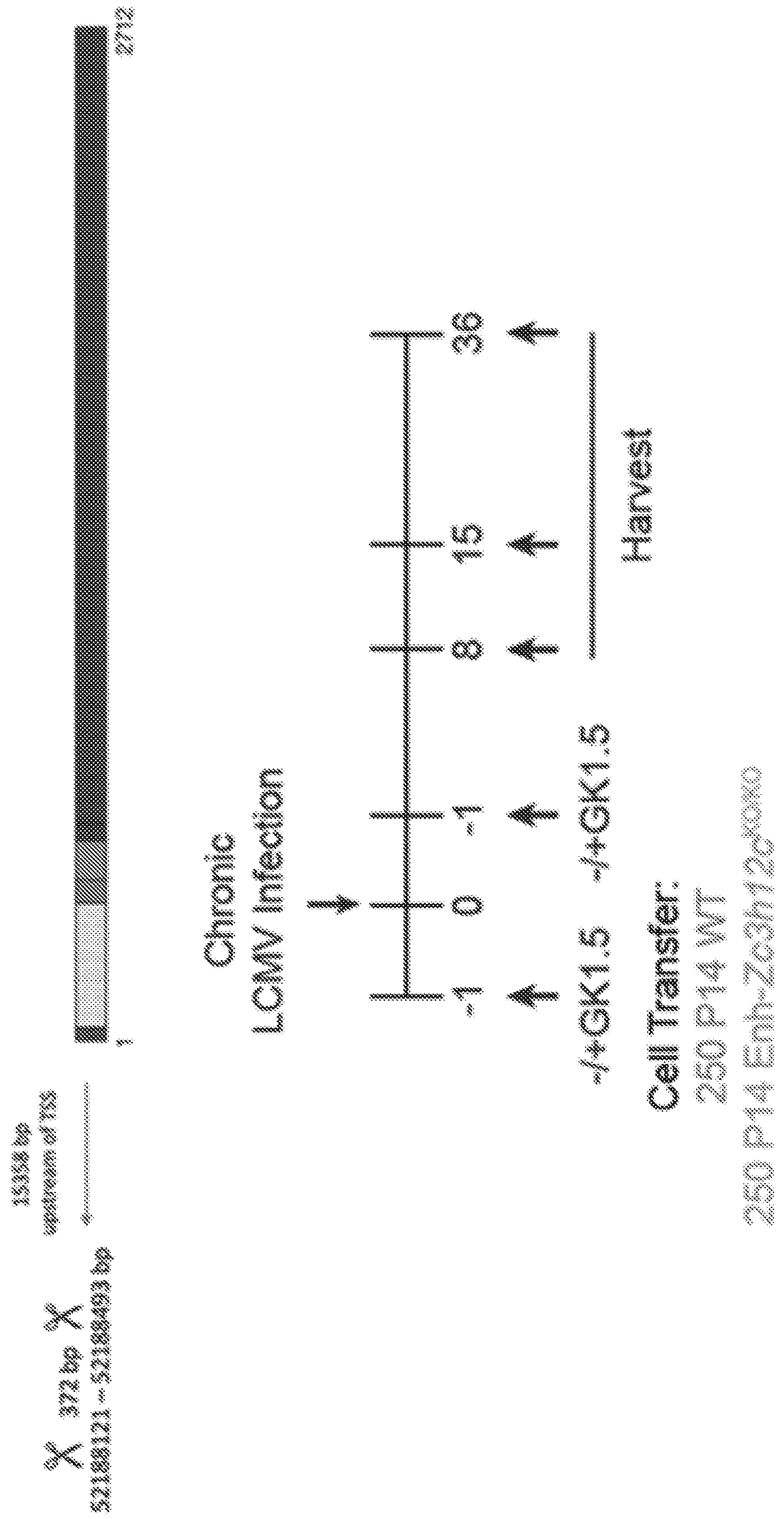
FIGS. 6A-6B illustrate in vivo testing of KO mice only missing the ~15 kb enhancer upstream of the Zc3h12c TSS.
Figure 6B:
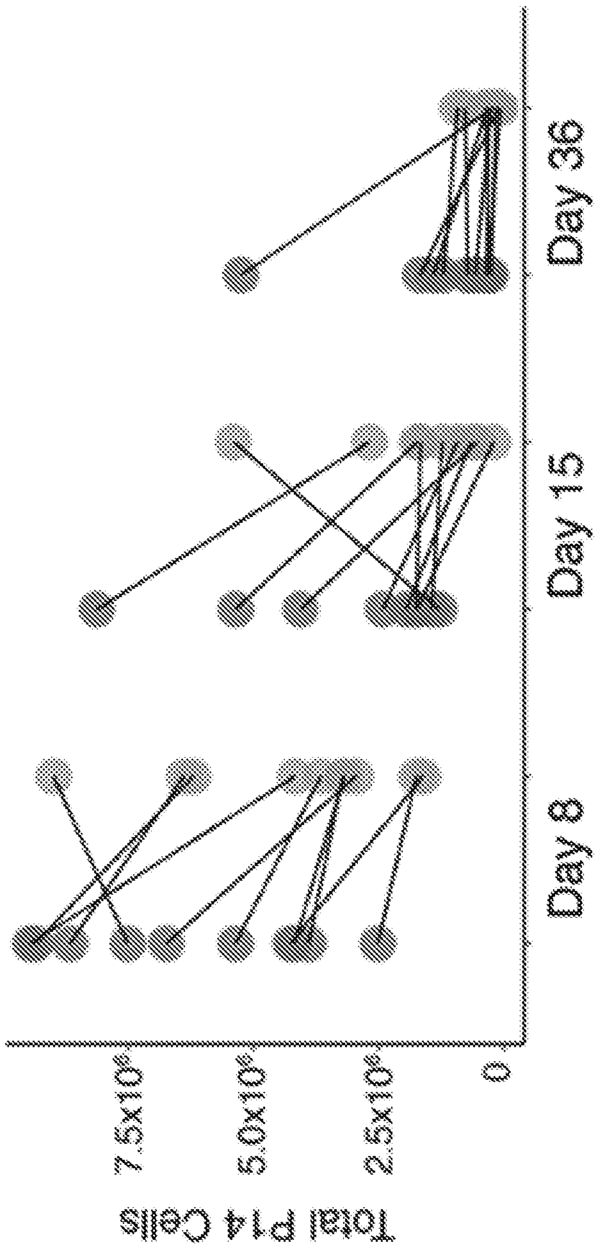

A total gene knockout (KO; i.e. germline deletion of exon 2) resulted in a decreased CD8 T cell response during chronic viral infection suggesting a role for Zc3h12c in fostering survival of $T_{EX}$, but relatively little impact on effector ($T_{EFF}$) or memory ($T_{MEM}$) CD8 T cells during acute infection (FIG. 5). These Zc3h12c KO cells also had reduced markers of T cell exhaustion, but decreased function suggesting that modulation of ZC3H12C might be of interest to improve T cell responses therapeutically in humans. Importantly, deleting only one enhancer element ~15 kb upstream of the TSS showed reduced CD8 T cell responses during chronic viral infection (FIG. 6B). CD8 T cells deficient in this enhancer also had reduced markers of exhaustion. Thus, removal of only a single exhaustion-specific non-coding cis regulatory enhancer element demonstrated a functional impact on T cell biology in vivo, indicating that a non-coding regulatory OCR may be targeted to regulate T cell biology without targeting the coding sequence of the gene.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A cell therapy composition comprising engineered T cells made by the process comprising the steps of:

(a) altering a non-coding DNA sequence comprising a regulatory domain present in an open chromatin region (OCR) associated with expression of one or more exhaustion-specific genes in a sample of T cells obtained from a subject; and (b) engineering the T cells to target an antigen;

wherein the altered non-coding DNA sequence reduces or reverses exhaustion of the T cells;

wherein the one or more exhaustion-specific genes is Zinc-finger CCCH-type containing 12C protein (ZC3H12C); and wherein the altering of the non-coding DNA sequence decreases expression of ZC3H12C.

2. The composition of claim 1, wherein the sample comprising T cells from the subject comprises CD8+ T cells.

3. The composition of claim 1, wherein the altering comprises knocking-out a regulatory domain present in an OCR associated with expression of one or more exhaustion-specific genes.

4. The composition of claim 3, wherein the knocking-out is conducted by a method selected from the group consisting of a clustered interspersed short palindromic repeat (CRISPR)/CRISPR-associated protein (Cas) system, a meganuclease, transcription activator-like effector nucleases (TALEN) and a Zinc-finger nuclease (ZFN).

5. The composition of claim 1, wherein the altered non-coding DNA sequence comprising a regulatory domain is an enhancer element located 15,358 bp upstream of ZC3H12C's transcription start site and the subject is human.

6. The composition of claim 1, wherein the altered non-coding DNA sequence comprising a regulatory domain is an enhancer element located on chromosome 11: 109948191-109949139, and the subject is human.

7. The composition of claim 1, wherein the method further comprises knocking out part of the coding sequence for ZC3H12C.

8. The composition of claim 7, wherein the knocking out part of the coding sequence for ZC3H12C comprises knocking out a single exon of the ZC3H12C gene.

9. The composition of claim 8, wherein the single exon of the ZC3H12C gene is exon 2.

10. A method of treating a disease characterized by increased numbers of exhausted CD8+ effector T cells ($T_{EX}$), comprising administering the improved cell therapy composition of claim 1.

11. The method of claim 10, wherein the disease is selected from the group consisting of cancer and infection.

12. The method of claim 11, wherein the disease is a viral infection.

13. The method of claim 12, wherein the viral infection is an acute viral infection or a chronic viral infection.

14. The method of claim 13, wherein the disease is an acute viral infection.

15. The method of claim 14, wherein the acute viral infection comprises infection with a virus selected from the group consisting of hepatitis viruses, herpesviruses, polyoma viruses, anelloviruses, adenoviruses, retroviruses, and influenza viruses.

16. The method of claim 15, wherein the virus is a hepatitis virus selected from the group consisting of Hepatitis A Virus (HAV), Hepatitis B Virus (HBV), Hepatitis C Virus (HCV), Hepatitis D Virus (HDV), Hepatitis E Virus (HEV), GB Hepatitis Virus A (GBV-A), GB Hepatitis Virus B (GBV-B), and GB Hepatitis Virus C (GBV-C).

17. The method of claim 15, wherein the virus is a herpesvirus selected from the group consisting of alpha-herpesviruses, herpes simplex virus type 1 (HSV1), herpes simplex virus type 2 (HSV2), varicella zoster virus (VZV), beta-herpesviruses, cytomegalovirus (CMV), human herpes virus 6, human herpes virus 7, gamma-herpesviruses, Epstein-Barr virus (EBV), and human herpes virus 8.

18. The method of claim 15, wherein the virus is a polyoma virus selected from the group consisting of BK virus (BKV), JC virus (JCV), KI polyoma virus (KIPyV), WU virus (WUPyV), Merkel cell polyomavirus (MCPyV), human polyoma virus 6 (HPyV6), human polyoma virus 7 (HPyV7), trichodysplasia spinulosa virus (TSPyV), human polyoma virus 9 (HPyV9), and MW virus (MWPyV).

19. The method of claim 15, wherein the virus is an adenovirus selected from the group consisting of adenovirus serotype A, adenovirus serotype B, adenovirus serotype C, adenovirus serotype D, adenovirus serotype E, adenovirus serotype F, and adenovirus serotype G.

20. The method of claim 15, wherein the virus is an influenza virus selected from group consisting of influenza virus A, influenza virus B, influenza virus C, and influenza virus D.

21. The method of claim 11, wherein the disease is a chronic viral infection.

22. The method of claim 21, wherein the chronic viral infection comprises infection with human immunodeficiency virus (HIV), HCV or HBV.

23. The method of claim 22, wherein the chronic viral infection is an HIV infection, and the subject is being treated with antiretroviral therapy (ART).

24. The method of claim 21, wherein the chronic viral infection is a retrovirus infection wherein the retrovirus is selected from the group consisting of alpha-retroviruses, beta-retroviruses, gamma-retroviruses, delta-retroviruses, epsilon-retroviruses, lentiviruses, and spumaviruses.

25. The method of claim 24, wherein the retrovirus is a lentivirus selected from the group consisting of HIV and equine infectious anemia virus (EIAV).

26. The method of claim 11, wherein the infection is a bacterial infection or a parasite infection.

27. The method of claim 11, wherein the disease is cancer.

28. The method of claim 1, wherein the engineering the T cells to target an antigen comprises introduction of a recombinant T cell receptor capable of binding the antigen when the antigen is presented by MHC or introduction of a chimeric antigen receptor capable of binding a desired antigen.

29. The method of claim 1, wherein the antigen is selected from the group consisting of CD19, PSMA, CAIX, HER2, CD30zeta, Folate receptor alpha, Mucinl (MUC1), Hepatitis C virus E2 glycoprotein, HIV envelope glycoprotein gp120, CMV pp65, GPC3, CEA, Mesothelin, GD2, EGFR, PSMA, EpCAM, BCMA, IL-13R, FAP and CD20.

* * * * *